United States Patent
Kadereit et al.

(10) Patent No.: US 10,792,367 B2
(45) Date of Patent: Oct. 6, 2020

(54) CONJUGATES COMPRISING AN GLP-1/GLUCAGON DUAL AGONIST, A LINKER AND HYALURONIC ACID

(71) Applicant: SANOFI, Paris (FR)

(72) Inventors: Dieter Kadereit, Frankfurt am Main (DE); Michael Wagner, Frankfurt am Main (DE); Thomas Olpp, Frankfurt am Main (DE); Nino Meyer, Frankfurt am Main (DE); Martin Bossart, Frankfurt am Main (DE); Andreas Evers, Frankfurt am Main (DE); Peyman Sakhaii, Frankfurt am Main (DE); Pradeep K. Dhal, Cambridge, MA (US); Paul Konowicz, Cambridge, MA (US); James E. Stefano, Cambridge, MA (US); Nils Poth, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/829,596

(22) Filed: Dec. 1, 2017

(65) Prior Publication Data

US 2018/0154005 A1 Jun. 7, 2018

(30) Foreign Application Priority Data

Dec. 2, 2016 (EP) .................................... 16306613

(51) Int. Cl.
| | |
|---|---|
| *A61K 38/17* | (2006.01) |
| *A61K 47/61* | (2017.01) |
| *A61K 47/54* | (2017.01) |
| *A61K 47/69* | (2017.01) |
| *A61P 3/04* | (2006.01) |
| *A61P 3/10* | (2006.01) |
| *A61K 9/00* | (2006.01) |
| *A61K 31/728* | (2006.01) |
| *A61K 38/26* | (2006.01) |
| *A61K 47/36* | (2006.01) |

(52) U.S. Cl.
CPC .......... *A61K 47/549* (2017.08); *A61K 9/0019* (2013.01); *A61K 31/728* (2013.01); *A61K 38/1703* (2013.01); *A61K 38/26* (2013.01); *A61K 47/36* (2013.01); *A61K 47/61* (2017.08); *A61K 47/6903* (2017.08); *A61P 3/04* (2018.01); *A61P 3/10* (2018.01)

(58) Field of Classification Search
CPC .... A61K 38/1703; A61K 38/22; A61K 38/26; A61K 47/61; C07K 14/46; C07K 14/575; C07K 14/605
See application file for complete search history.

(56) References Cited

U.S. PATENT DOCUMENTS

| | | | |
|---|---|---|---|
| 9,365,632 B2 * | 6/2016 | Haack | ............... A61K 38/2264 |
| 2005/0142152 A1 * | 6/2005 | Leshchiner | .......... A61K 9/0014 |
| | | | 424/400 |
| 2011/0152181 A1 | 6/2011 | Alsina-Fernandez | |
| 2011/0152182 A1 | 6/2011 | Alsina-Fernandez | |
| 2013/0189328 A1 | 7/2013 | Cleemann et al. | |
| 2014/0100156 A1 * | 4/2014 | Haack | ................. C07K 14/605 |
| | | | 514/1.9 |
| 2015/0166625 A1 | 6/2015 | Haack et al. | |
| 2015/0258207 A1 | 9/2015 | Rau et al. | |

FOREIGN PATENT DOCUMENTS

| | | |
|---|---|---|
| EP | 1790665 A1 | 5/2007 |
| EP | 2 387 989 A2 | 11/2011 |
| WO | WO 2006/134340 A2 | 12/2006 |
| WO | WO 2008/071972 A1 | 6/2008 |
| WO | WO 2008/101017 A2 | 8/2008 |
| WO | WO 2008/148839 A2 | 12/2008 |

(Continued)

OTHER PUBLICATIONS

Kong et al. (2010) "Long acting hyaluronate—exendin 4 conjugate for the treatment of type 2 diabetes," Biomaterials, 31:4121-4128.
Shendi et al. (2016) "Tunable, bioactive protein conjugated hyaluronic acid hydrogel for neural engineering applications," Journals of Materials Chemistry B, 4:2803-2818.
International Search Report for International Application No. PCT/EP2017/081217, dated Mar. 20, 2018.
Buse at al. (2009) Liraglutide once a day versus exenatide twice a day for type 2 diabetes: a 26-week randomised, parallel-group, multinational, open-label trial (LEAD-6), Lancet, vol. 374, pp. 39-47.

(Continued)

Primary Examiner — Jeffrey E. Russel
(74) Attorney, Agent, or Firm — Lathrop GPM LLP; James H. Velema, Esq.

(57) ABSTRACT

The present invention relates to a conjugate or a pharmaceutically acceptable salt thereof comprising an GLP-1/Glucagon receptor agonist, a linker and a hyaluronic acid hydrogel bearing -L1-L2-L—Y—R20 groups, wherein Y represents an GLP-1/Glucagon receptor agonist moiety; and -L is a linker moiety—by formula (Ia), (Ia)

Figure 1A:
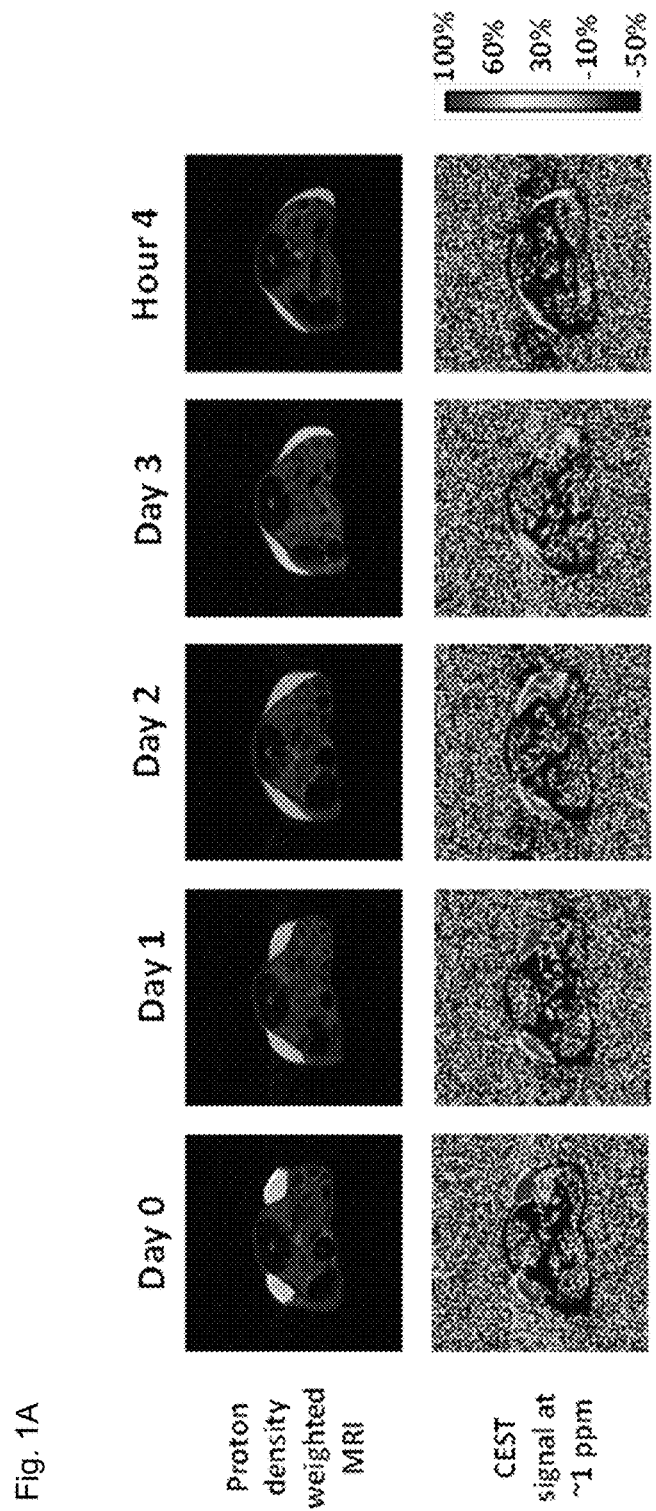

wherein the dashed line indicates the attachment to one of the amino groups of the GLP-1/Glucagon receptor agonist moiety by forming an amide bond. The invention further relates to pharmaceutical compositions comprising the conjugates as well as their use as a medicament for treating or preventing diseases or disorders which can be treated by GLP-1/Glucagon receptor agonist.

36 Claims, 11 Drawing Sheets

Specification includes a Sequence Listing.

(56) References Cited

FOREIGN PATENT DOCUMENTS

| WO | WO 2008/152403 A1 | 12/2008 |
| --- | --- | --- |
| WO | WO 2009/095479 A2 | 8/2009 |
| WO | WO 2009/133137 A2 | 11/2009 |
| WO | WO 2011/058053 A1 | 11/2009 |
| WO | WO 2009/155258 A2 | 12/2009 |
| WO | WO 2010/043566 A2 | 4/2010 |
| WO | WO 2010/070251 A1 | 6/2010 |
| WO | WO 2010/070252 A1 | 6/2010 |
| WO | WO 2010/070253 A1 | 6/2010 |
| WO | WO 2010/070255 A1 | 6/2010 |
| WO | WO 2010/096052 A1 | 8/2010 |
| WO | WO 2010/096142 A1 | 8/2010 |
| WO | WO 2011/006497 A1 | 1/2011 |
| WO | WO 2011/12718 A1 | 2/2011 |
| WO | WO 2011/058082 A1 | 5/2011 |
| WO | WO 2011/075393 A2 | 6/2011 |
| WO | WO 2011/117415 A1 | 9/2011 |
| WO | WO 2011/117416 A1 | 9/2011 |
| WO | WO 2011/160630 A2 | 12/2011 |
| WO | WO 2012/035139 A1 | 3/2012 |
| WO | WO 2012/173422 A1 | 12/2012 |
| WO | WO 2014/000056 A1 | 1/2014 |
| WO | 2014056872 A1 | 4/2014 |
| WO | WO2014/096145 A1 | 6/2014 |
| WO | WO2014/096150 A1 | 6/2014 |
| WO | WO2014096148 A1 | 6/2014 |
| WO | WO2014096149 A1 | 6/2014 |
| WO | WO2015/067716 A1 | 5/2015 |
| WO | WO2015/086731 A1 | 6/2015 |
| WO | WO2015/086732 A1 | 6/2015 |
| WO | WO2015/086733 A1 | 6/2015 |
| WO | WO2015/155141 A1 | 10/2015 |
| WO | 2016193371 A1 | 12/2016 |

OTHER PUBLICATIONS

Chhabra et al. (1998) "An appraisal of new variants of Dde amine protecting group for solid phase peptide synthesis", Tetrahedron Letters, vol. 39, pp. 1603-1606.

Chen et al. (2013) "Hyaluronic acid-based drug conjugates: State-of-the-art and perspectives", Journal of Biomedical Nanotechnology, vol. 9, pp. 1-13.

Day et al. (2009) "A new glucagon and GLP-1 co-agonist eliminates obesity in rodents", Nature Chemical Biology, 2009, vol. 5, No. 10, pp. 749-757.

Drucker et al. (2010) "Liraglutide", Nature Reviews Drug Discovery, vol. 9, pp. 267-268.

Hjorth et al. (1994) "Glucagon and glucagon-like peptide 1: Selective receptor recognition via distinct peptide epitopes", The Journal of Biological Chemistry, vol. 269, No. 48, pp. 30121-30124.

King et al. (1990) "A cleavage method which minimizes side reactions following Fmoc solid phase peptide synthesis", Int. J. Peptide Protein Res., vol. 36, pp. 255-266.

Oh et al. (2014) "Target specific and long-acting delivery of protein, peptide, and nucleotide therapeutics using hyaluronic acid derivatives", Journal of Controlled Release, 141, pp. 2-12.

Otzen et al. (2006) "N- and C- terminal hydrophobic patches are involved in fibrillation of glucagon", Biochemistry, vol. 45, pp. 14503-14512.

Pocai et al. (2012) "The glucagon receptor is involved in mediating the body-weight-lowering effects of oxyntomodulin", Obesity, vol. 20, No. 8, pp. 1566-1571.

Pocai et al. (2009) "Glucagon-like peptide 1/glucagon receptor dual agonism reverses obesity in mice", Diabetes, vol. 58, pp. 2258-2266.

Zihl et al. (2011) "Chemical Exchange Saturation Transfer (CEST): What is in a Name and What Isn't?," Magnetic Resonance in Medicine, 65(4), pp. 927-948.

European Patent Application No. 16306613.7, Extended Search and Opinion dated May 19, 2017, 12 pages.

Office Action dated Mar. 8, 2019 in U.S. Appl. No. 15/829,596, 9 pages.

Chen et al. (Jan. 2014) "Hyaluronic acid-based drug conjugates: state-of-the-art and perspectives," J. Biomed. Nanotechnol. 10(1):4-16.

\* cited by examiner

SEQUENCE LISTING

```
<160> NUMBER OF SEQ ID NOS: 6

<210> SEQ ID NO 1
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: Ser is modified with an NH2 group

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 29
<212> TYPE: PRT
<213> ORGANISM: Homo sapiens
<220> FEATURE:
<221> NAME/KEY: MOD_RES
<222> LOCATION: (29)..(29)
<223> OTHER INFORMATION: Arg is modified with an NH2 group

<400> SEQUENCE: 2

His Ala Glu Gly Thr Phe Thr Ser Asp Val Ser Ser Tyr Leu Glu Gly
1               5                   10                  15

Gln Ala Ala Lys Glu Ile Ala Trp Leu Val Lys Gly Arg
            20                  25

<210> SEQ ID NO 3
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Thr is modified with an OH group

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Val Gln Trp Leu Met Asn Thr
            20                  25

<210> SEQ ID NO 4
<211> LENGTH: 31
<212> TYPE: PRT
<213> ORGANISM: Artificial sequence
<220> FEATURE:
<223> OTHER INFORMATION: liraglutide
<220> FEATURE:
```

```
<221> NAME/KEY: MOD_RES
<222> LOCATION: (20)..(20)
<223> OTHER INFORMATION: Lys derivatized at N6 with
      (S)-4-carboxy-4-hexadecanoylamino-butyryl

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 5
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: X is a D-Ser
<220> FEATURE:
<221> NAME/KEY: MOD_RES
<222> LOCATION: (2)..(2)
<223> OTHER INFORMATION: Xaa is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 5

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: X is a D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: Ser is modified with an NH2 group

<400> SEQUENCE: 6
```

```
His Xaa Gln Gly Thr Phe Thr Ser Asp Leu Ser Lys Gln Lys Asp Glu
1               5                   10                  15

Gln Leu Ala Lys Asp Phe Ile Glu Trp Leu Lys Ala Gly Gly Pro Ser
            20                  25              30

Ser Gly Ala Pro Pro Pro Ser
        35
```

CONJUGATES COMPRISING AN GLP-1/GLUCAGON DUAL AGONIST, A LINKER AND HYALURONIC ACID

RELATED APPLICATION

This application claims priority to European Patent Application No. 16306613, filed Dec. 2, 2016, the entire disclosure of which is hereby incorporated herein by reference.

SEQUENCE LISTING

The instant application contain Sequence Listing which has been submitted electronically in ASCII format and is incorporated by reference in its entirety. Said ASCII copy, created on Dec. 1, 1017, is named 597422_SA9-224_Sequence_Listing.TXT and is 3,579 bytes in size.

FIELD OF THE INVENTION

The present invention relates to conjugates comprising an GLP-1/Glucagon dual agonist, a linker and hyaluronic acid, pharmaceutical compositions comprising said conjugates, as well as their use as a medicament for treating or preventing diseases or disorders which can be treated by a GLP-1/Glucagon dual agonist, for example in the treatment of disorders of the metabolic syndrome, including diabetes and obesity, as well as for reduction of excess food intake.

BACKGROUND OF THE INVENTION

GLP-1 Agonists

Exendin-4 is a 39-amino acid peptide, isolated from the salivary secretions of the venomous Gila monster (*Heloderma suspectum*). It has some sequence similarity to several members of the glucagon-like peptide family, with the highest homology of 53% being to glucagon-like peptide-1 [7-36]-amide (GLP-1). Exendin-4 acts as a agonist on the GLP-1 receptor and bears GLP-1-like insulin sectretagogue action in isolated rat islets. Exendin-4 is a high potency agonist and truncated GLP-1 agonist-(9-39)-amide is an antagonist at the glucagon-like peptide 1-(7-36)-amide receptor of insulin-secreting beta-cells. Exendin-4 ("exenatide") was approved recently in the US and EU for improving glycemic control in patients with type 2 diabetes taking metformin and/or a sulfonylurea but have not achieved adequate glycemic control.

The amino acid sequence of exendin-4 is shown as SEQ ID NO: 1

HGEGTFTSDLSKQMEEEAVRLFIEWLKNGGPSSGAPPPS-NH$_2$

The amino acid sequence of GLP-1(7-36)-amide is shown as SEQ ID NO: 2

HAEGTFTSDVSSYLEGQAAKEFIAWLVKGR-NH$_2$

Glucagon is a 29-amino acid peptide which is released into the bloodstream when circulating glucose is low. Glucagon's amino acid sequence is shown in SEQ ID NO: 3.

HSQGTFTSDYSKYLDSRRAQDFVQWLMNT-OH

Liraglutide is a marketed chemically modified GLP-1 analog in which, among other modifications, a fatty acid is linked to a lysine in position 20 leading to a prolonged duration of action (Drucker D J et al., Nature Drug Disc. Rev. 9, 267-268, 2010; Buse, J. B. et al., Lancet, 374:39-47, 2009).

The amino acid sequence of Liraglutide is shown as SEQ ID NO: 4.

HAEGTFTSDVSSYLEGQAAK((S)-4-Carboxy-4-hexadecanoylamino-butyryl-)EFIAWLVRGRG-OH

During hypoglycemia, when blood glucose levels drop below normal, glucagon signals the liver to break down glycogen and release glucose, causing an increase of blood glucose levels to reach a normal level. Hypoglycemia is a common side effect of insulin treated patients with hyperglycemia (elevated blood glucose levels) due to diabetes. Thus, glucagon's most predominant role in glucose regulation is to counteract insulin action and maintain blood glucose levels.

GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

GLP-1/Glucagon (Glc) Agonists

Pocai et al (Obesity. 2012; 20:1566-1571; Diabetes 2009, 58, 2258) and Day et al. (Nat Chem Biol 2009; 5:749) describe that dual activation of the GLP-1 and glucagon receptors, e.g., by combining the actions of GLP-1 and glucagon in one molecule leads to a therapeutic principle with anti-diabetic action and a pronounced weight lowering effect.

Peptides which bind and activate both the glucagon and the GLP-1 receptor (Hjort et al. Journal of Biological Chemistry, 269, 30121-30124,1994; Day J W et al, Nature Chem Biol, 5: 749-757, 2009) and suppress body weight gain and reduce food intake are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO2011/117415, WO2011/117416, and WO 2006/134340.

Bloom et al. (WO 2006/134340) disclose that peptides which bind and activate both the glucagon and the GLP-1 receptor can be constructed as hybrid molecules from glucagon and exendin-4, where the N-terminal part (e.g. residues 1-14 or 1-24) originate from glucagon and the C-terminal part (e.g. residues 15-39 or 25-39) originate from exendin-4.

Otzen et al (Biochemistry, 45, 14503-14512, 2006) disclose that N- and C-terminal hydrophobic patches are involved in fibrillation of glucagon, due to the hydrophobicity and/or high β-sheet propensity of the underlying residues.

WO2014/056872 discloses peptides which bind and activate both the glucagon and the GLP-1 receptor that are derived from exendin-4 wherein at least the aminoacid position 14 bear a side chain for a prolonged halflife which makes them appropriate as active ingredient in the present invention.

Long Acting GLP-1/Glucagon Agonists

Ideally, the peptide is formulated in a fashion that provides for a sustained plasma level in human for at least one week after application to a human body resulting in a once-weekly or longer injection frequency.

Current therapy with a long acting GLP-1 agonists is Bydureon® which is exendin-4 in a depot suspension for a once weekly injection based on poly(glycol-co lactic acid) using a 23 gauge needle.

WO2012/173422 describes a GLP-1/Glucagon agonist conjugated to the Fc region of an immunoglobulin for weekly administration wherein the peptide is derived from oxyntomodulin.

Carrier Linked Prodrugs

To enhance physicochemical or pharmacokinetic properties of a drug in vivo, such as its half-life, such drug can be conjugated with a carrier. If the drug is transiently bound to a carrier and/or a linker, such systems are commonly assigned as carrier-linked prodrugs. According to the definitions provided by IUPAC, a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers used in such carrier-linked prodrugs may be transient, meaning that they are non-enzymatically hydrolytically degradable (cleavable) under physiological conditions (aqueous buffer at pH 7.4, 37° C.) with half-lives ranging from, for example, one hour to three months. Suitable carriers are polymers and can either be directly conjugated to the linker or via a non-cleavable spacer.

Transient polymer conjugation through traceless prodrug linkers combines the advantages of prolonged residence time due to polymer attachment, a controlled drug release via linker optimization and the recovery of the original pharmacology of the native peptide after release from the polymer conjugate.

Using polymer-linker peptide conjugates, native unchanged peptide is slowly released after application to a patient, governed only by release kinetics of the linker and pharmacokinetics of the polymer carrier. Ideally, release kinetics would be independent from the presence of enzymes like proteases or esterases in body fluids to guarantee a consistent and homogenous release pattern.

Many acute side effects of drugs may be related to the drug peak levels which thereby may limit the dose for a given drug formulation. Reducing the drug peak levels (maximal drug concentration, Cmax) for a given dose may allow those drugs to be administered in higher doses without raising the risk of acute side effects. Administration of higher doses in turn may allow to reduce the dosing frequency eventually leading to a once-weekly or even once-monthly dosing interval.

The administration of carrier-linked prodrugs may allow to control the drug release in a manner that the drug concentration remains relatively flat for a certain time period. The drug release itself will be mainly controlled by the linker which needs to be optimized for the intended dosing interval.

A suitable polymer needs to have a clearance half-life significantly longer than the drug release half-life of the linker as otherwise a part of the polymer will be cleared while the drug is still attached to it. A short carrier half-life would therefore lead to a loss of drug for a given dose and to a steeper drug concentration curve.

WO2008/148839, WO2009/095479 and WO2012/035139 refer to prodrugs comprising drug linker conjugates, where the linker is covalently attached via a cleavable bond to a biologically active moiety, such as the GLP 1-agonist exendin-4. The biologically active moiety is released from the prodrug upon cyclization-activation by cyclic imide formation. The release kinetic is dependent on the pH value and is minimum for storage of the prodrug at pH values from 4.5 to 5 and reach its intended release rate at physiological pH of around 7.4 to 7.5. An GLP-1 agonist-prodrug is described in which the linker is based on L-alanine and the polymeric carrier is a PEG-lysine based hydrogel. Not described are dual GLP-1/Glucagon agonist-prodrugs.

Hyaluronic Acid (HA)

Dhal et al (Journal of Biomedical Nanotechnology, vol 9, 2013, 1-13) report hyaluronic acid as a suitable carrier for drug conjugates. Kong et al. (Biomaterials 31 (2010), 4121-4128) report an exendin-4-hyaluronic acid conjugate which showed an glucose lowering effect over 3 days in mice. The used HA was a linear polymer with a drug load ranging from about 2.4 to 12.%.

Shendi et al (J. Mater. Chem B, 2016, 4, 2803-2818) discloses a hyaluronic acid which was modified with divinylsulfone wherein a part of the viylsulfone groups are used to conjugate bioactive molecules and the remaining vinylsulfone groups are used as crosslinkers to form the hyaluronic acid hydrogel.

EP1790665 A1 discloses a process for producing a water soluble modified hyaluronic acid using a condensing agent for the conjugation of a drug to the hyaluronic acid. These conjugates enhances the residence time of the drug in the blood by i.v. administration. Also disclosed was the crosslinking of these conjugates to form a gel.

DESCRIPTION OF THE INVENTION

GLP-1/Glucagon dual agonist peptides suitable for the conjugates of the invention have a high solubility at acidic and/or physiological pH values e.g. at pH 4.5 and/or pH 7.4 at 25° C. Also the chemical stability at pH values of 4.5 to 5 is an important criterion for the long acting prodrug product. The prodrug is preferably formulated in this pH range in order to obtain a shelf-life from at least 6 month at 4° C.

In the present invention hydrogels of crosslinked hyaluronic acid were chosen due to their longer residence time as a local depot at the application site than soluble HA. Important criteria for the use of hyaluronic acid (HA) as a carrier polymer is the achievable drug load in the final drug product which is determined by the drug load on the polymer itself and the concentration of the final solution/suspension. Giving the fact that the injection volume for subcutaneous drug depots is practically limited to equal/less than 1 mL, preferably equal/less than 0.6 mL.

The more concentrated the polymer solutions/suspensions of HA is, the more viscous is the formulation which has a negative impact on the syringability of the conjugate formulation. Viscous solutions need injection needles of a larger diameter to limit the force on the plunger of which the syringe is pressed. Also the time for injection is longer.

It was an object of the present invention to provide a conjugate for administering as a subcutaneous depot which releases a GLP-1/Glucagon agonist in an active form over the time period of at least 6 days after administrations and which can be injected through 26 gauge needles or even needles of smaller inner diameter for good patient compliance.

An object of the invention is a conjugate or a pharmaceutically acceptable salt thereof, comprising a
crosslinked hyaluronic acid hydrogel, in which
0.001 to 20 mol % of the monomeric disaccharide units are crosslinked by a crosslinker; and
0.2 to 20 mol % of the monomeric disaccharide units bear -L$^1$-L$^2$-L-Y—R$^{20}$ groups;

L$^1$ is a C$_{1-20}$ alkyl chain, in which optionally one or more carbon atoms are replaced by a group selected from —O—, NH(R$^{5aa}$) and C(O)N(R$^{5aa}$), and is optionally substituted with one or more groups independently selected from OH and C(O)N(R$^{5aa}$R$^{5aaa}$), wherein R$^{5aa}$ and R$^{5aaa}$ are independently selected from the group consisting of H and C$_{1-4}$ alkyl; and L$^1$ is attached to the hydrogel via a terminal amino group forming an amide bond with the carboxy group of the beta-1,3-D-glucuronic acid of the hyaluronic acid L$^2$ is a single chemical bond or is a C$_{1-20}$ alkyl chain, in which optionally one or more carbon atoms are replaced by a group selected from —O— and C(O)N(R$^{3aa}$), and is optionally substituted with one or more groups independently selected from OH and C(O)N(R$^{3aa}$R$^{3aaa}$), wherein R$^{3aa}$ and R$^{3aaa}$ are independently selected from the group consisting of H and C$_{1-4}$ alkyl; and L$^2$ is attached to L$^1$ via a terminal group selected from the group consisting of

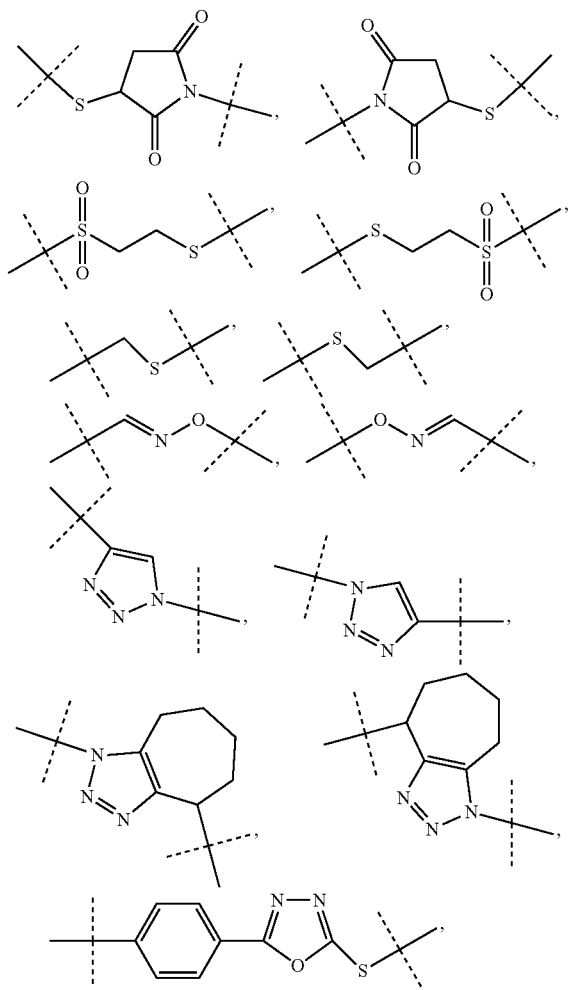

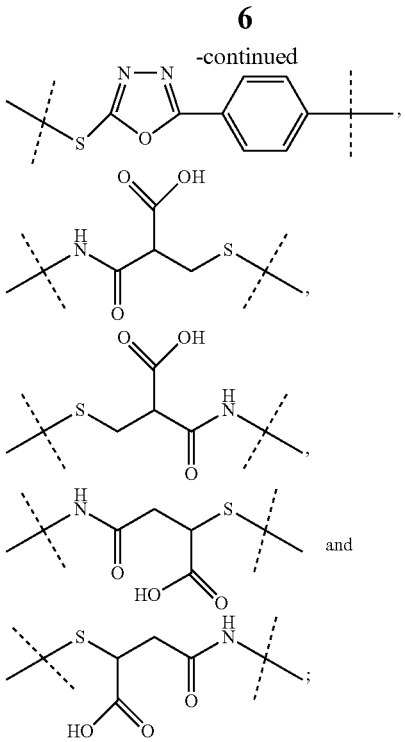

wherein L$^2$ is attached to the one position indicated with the dashed line and L$^1$ is attached to the position indicated with the other dashed line;

L is a linker of formula (Ia),

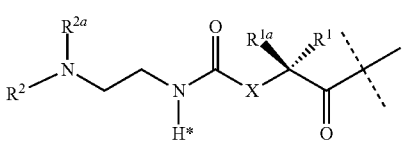

(Ia)

wherein the dashed line indicates the attachment to the N-Terminus of Y by forming an amide bond;

X is C(R$^4$R$^{4a}$) or N(R$^4$);

R$^1$, R$^{1a}$, are independently selected from the group consisting of H; and C$_{1-4}$ alkyl;

R$^2$, R$^{2a}$, are independently selected from the group consisting of H; and C$_{1-4}$ alkyl;

R$^4$, R$^{4a}$, are independently selected from the group consisting of H; and C$_{1-4}$ alkyl;

wherein one of R$^2$, R$^{2a}$, R$^4$ or R$^{4a}$ is attached to L$^2$;

Y is a peptide moiety having the formula (Ib)

```
His-D-Ser-Gln-Gly-Thr-Phe-Thr-Ser-Asp-Leu-Ser-Lys-
Gln-X14-Glu-Ser-Lys-Ala-Ala-Gln-Asp-Phe-Ile-Glu-
Trp-Leu-Lys-Ala-Gly-Gly-Pro-Ser-Ser-Gly-Ala-Pro-
Pro-Pro-Ser  (Ib)
``` wherein X14 represents Lys, wherein the —NH$_2$ side chain group is functionalized by (S)-4-carboxy-4-hexadecanoylamino-butyryl;

or Y is a peptide moiety having the formula (Ic)

His-dSer-Gln-Gly-Thr-Phe-Thr-Ser-Asp-Leu-Ser-Lys-

Gln-X14-Asp-Glu-Gln-Leu-Ala-Lys-Asp-Phe-Ile-Glu-

Trp-Leu-Lys-Ala-Gly-Gly-Pro-Ser-Ser-Gly-Ala-Pro-

Pro- Pro-Ser (Ic)

wherein X14 represents Lys, wherein the —NH$_2$ side chain group is functionalized by (S)-4-carboxy-4-octa-decanoylamino-butyryl;

R$^{20}$ is OH or NH$_2$.

The present invention relates to a conjugate which provides a GLP-1/Glucagon agonist release from a subcutaneous depot in an active form over the time period of at least 6 days after administration.

This helps patients to reduce the frequency of injections, while being able to maintain optimal control the plasma levels of GLP-1/Glucagon agonist and consequently blood glucose.

Additionally, the conjugate according to this invention may release the dual GLP-1/Glucagon agonist in a release profile resulting in a very flat pharmacokinetic profile of the agonist leading to a lower risk of Cmax-related side effects.

Further advantages of the conjugate of the invention are the good injectability through a 26 gauge needle or even a needle of a smaller inner diameter.

LEGENDS TO THE FIGURES

FIG. 1A: In Vivo Degradation Profile and Kinetics of Degradation of High Molecular Wight (2.5 Million Da) Hyaluronan (HA).

The implanted HA was monitored by MRI technique. Representative MRI images obtained by both Standard (top) and CEST (bottom) imaging techniques.

Figure 1B:
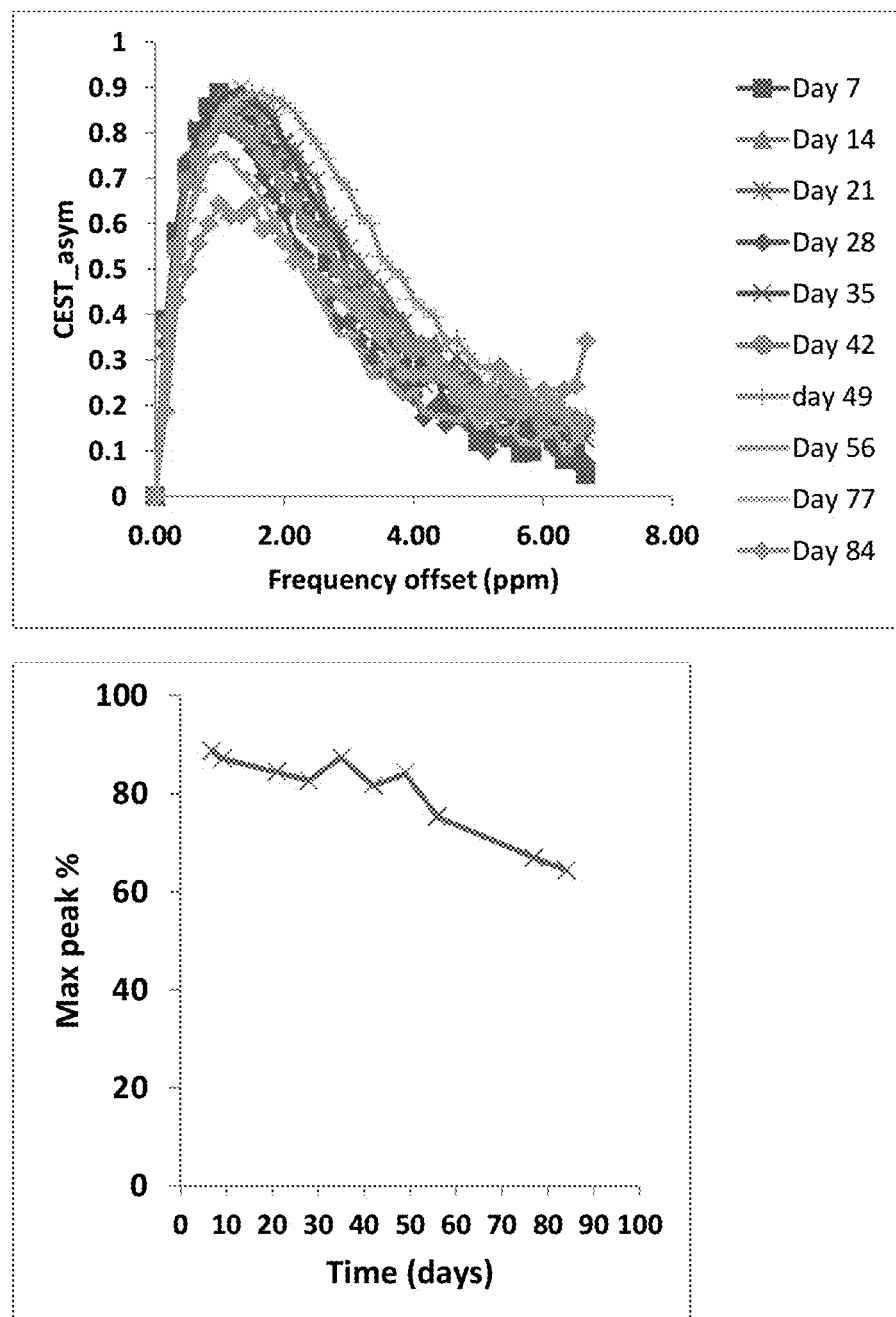

FIG. 1B: In Vivo Degradation Profile and Kinetics of Degradation of Divinyl Sulfone Crosslinked Hyaluronan. Kinetics of degradation was determined by plotting peak magnitude at 1 ppm.

Figure 1C:
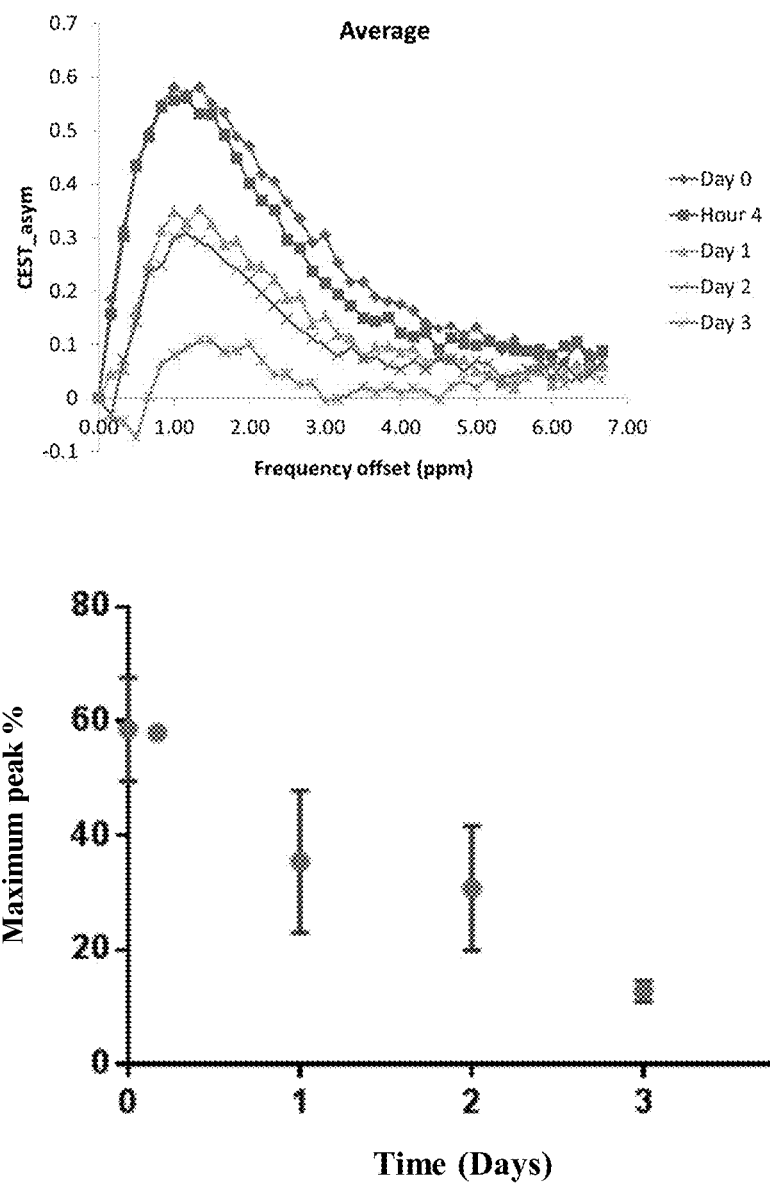

FIG. 1C: In Vivo Degradation Profile and Kinetics of Degradation of High Molecular Wight (2.5 Million Da) Hyaluronan (HA).

Kinetics of degradation was determined by plotting peak magnitude at 1 ppm.

Figure 2:
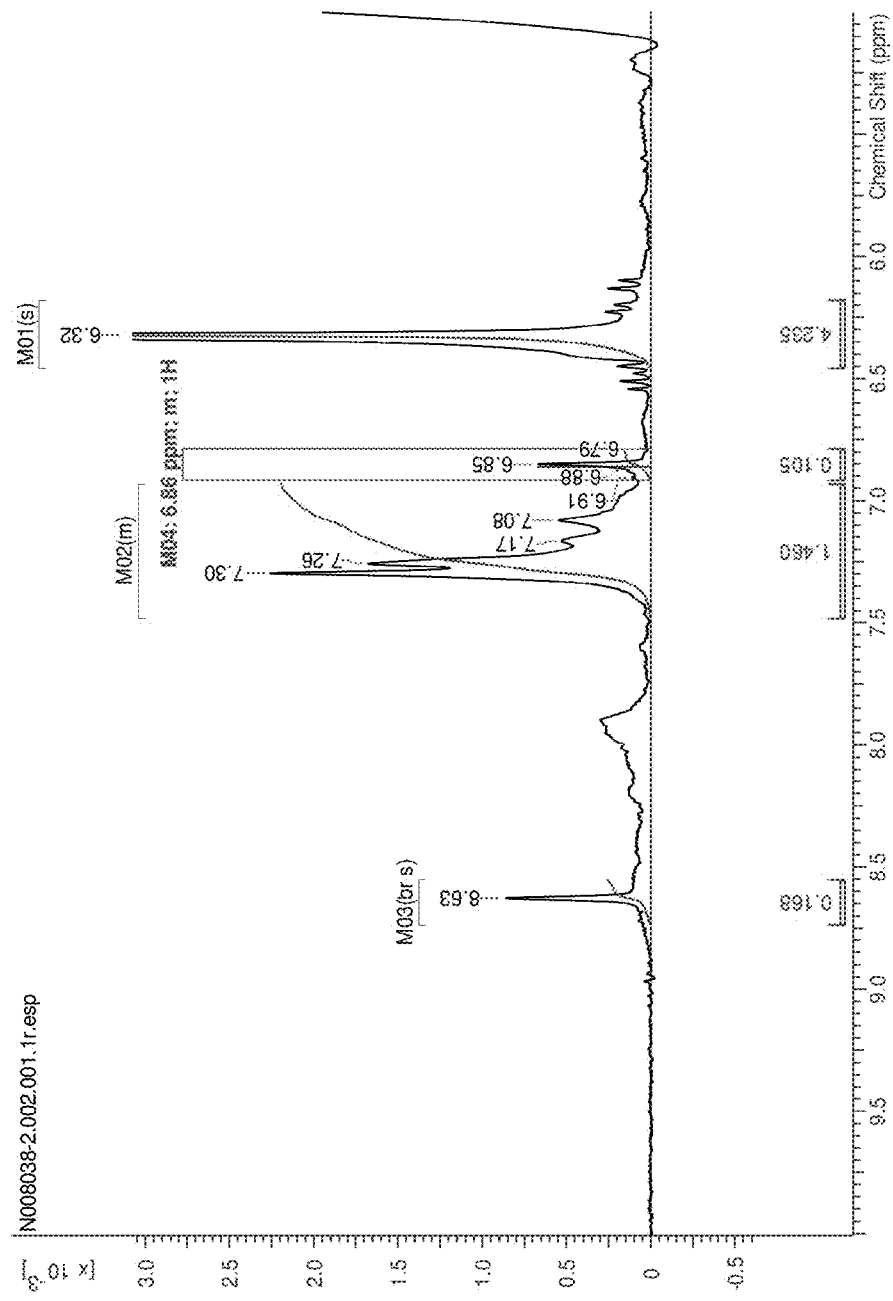

FIG. 2: Solid state 1H-NMR spectra of HA-hydrogel-Aib-linker conjugate of peptide of Seq. ID No. 5.

Figure 3:
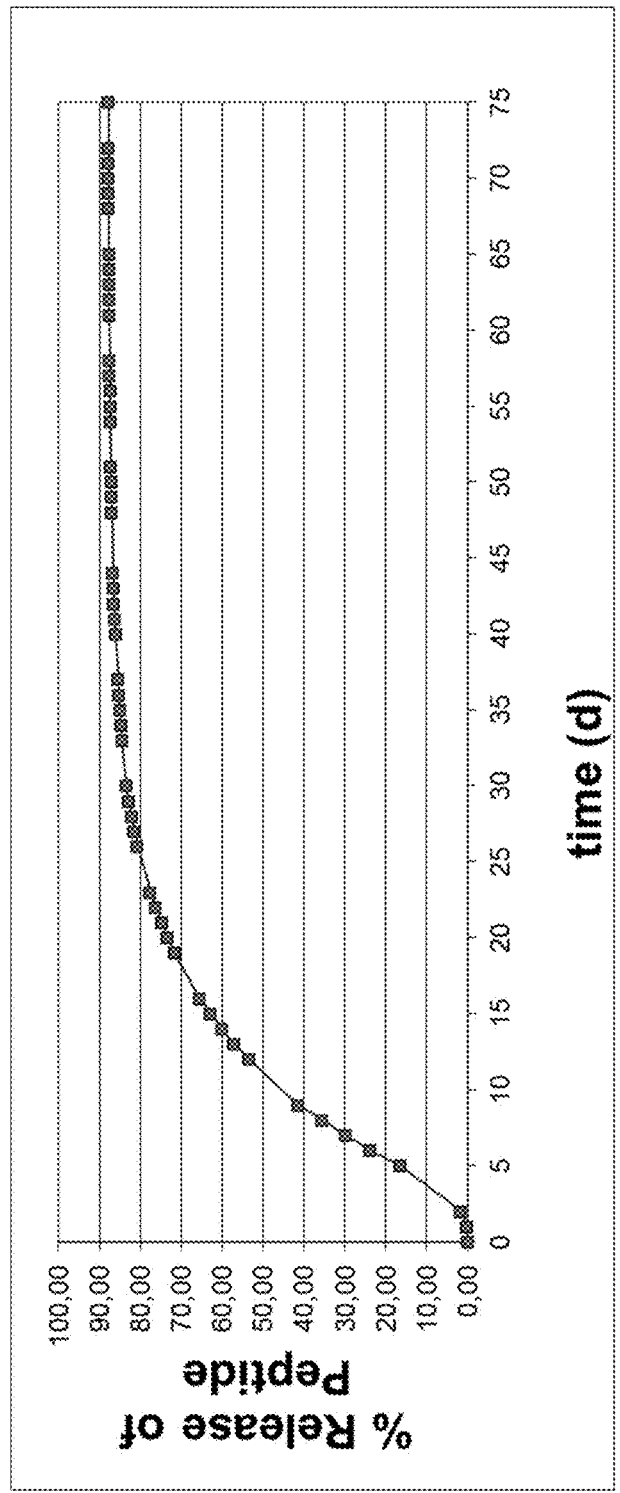

FIG. 3. In vitro release kinetics of Peptide with Seq. ID No. 5 from HA-hydrogel-Aib-linker conjugate.

Figure 4:
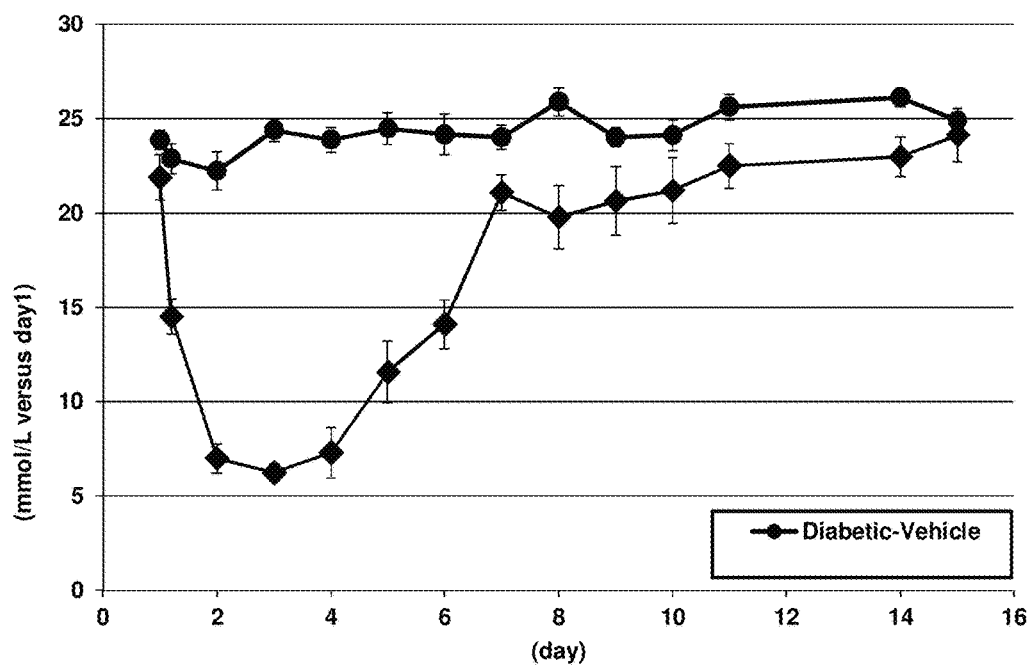

FIG. 4: Fed blood glucose profile in male db/db mice treated with a single-dose (day 1) SEQ ID NO: 5 with non-crosslinked HA.

Figure 5A:
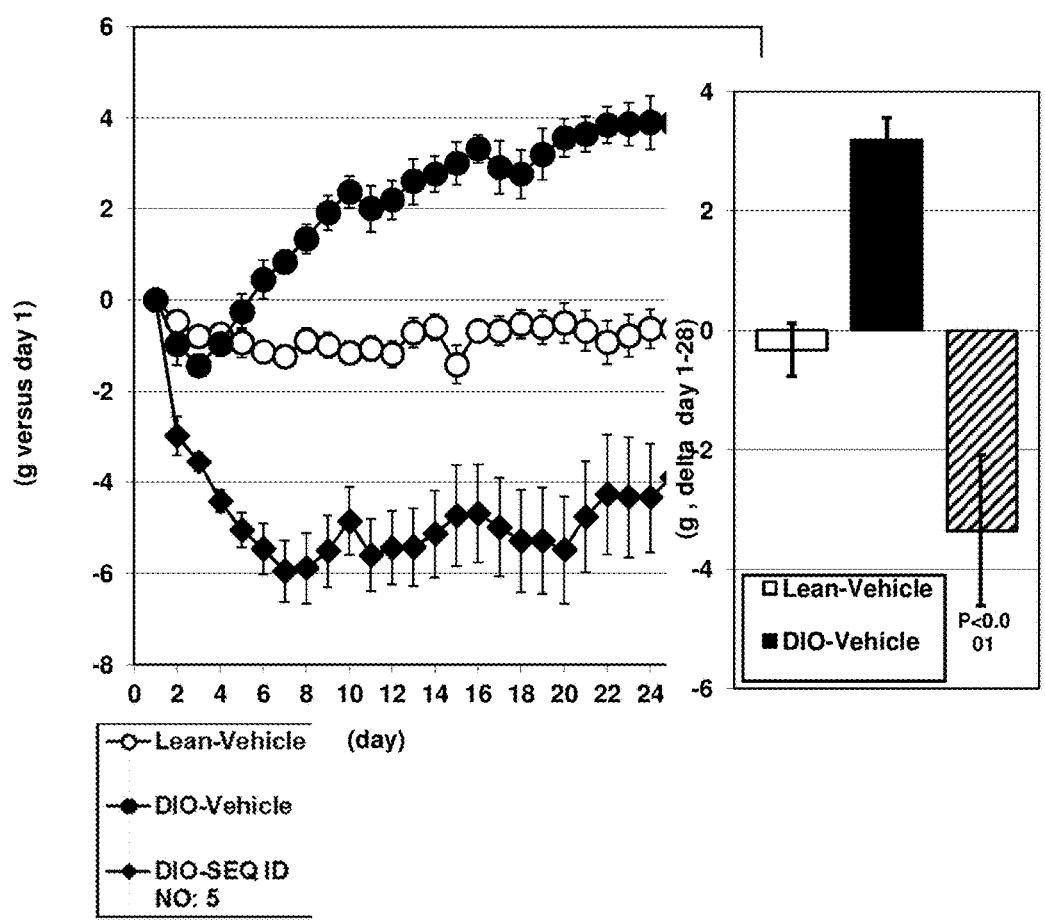

FIG. 5A: Body mass change of female diet-induced obese mice treated with four doses (day 1, 8, 15, 22) HA-hydrogel-Aib-linker conjugate with peptide of SEQ ID NO: 5.

Figure 5B:
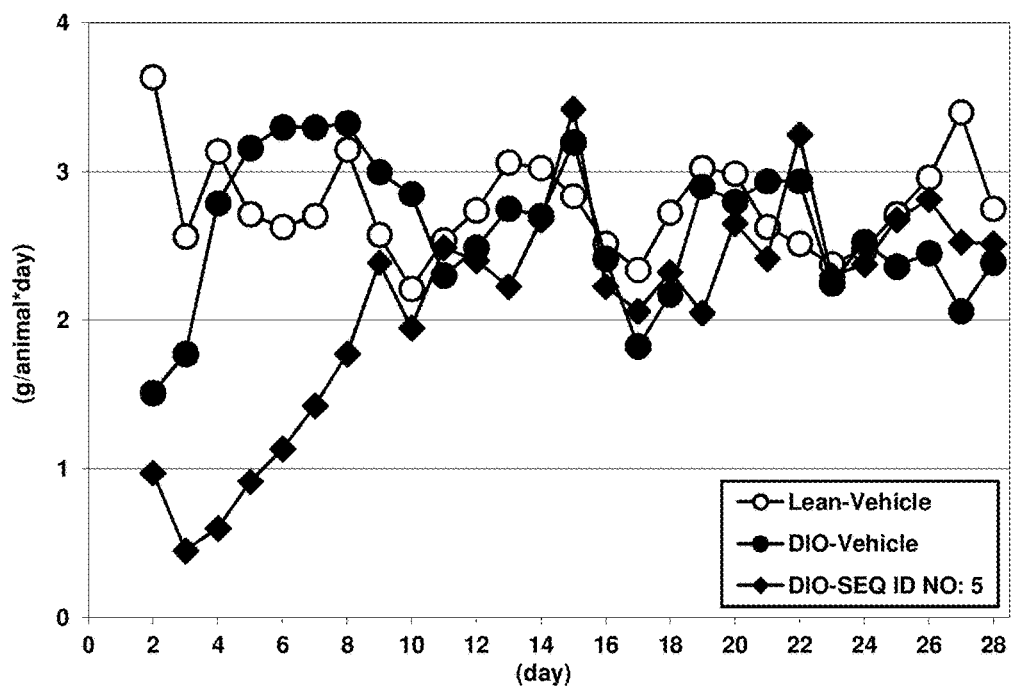

FIG. 5B: Feed consumption of female diet-induced obese mice treated with four doses (day 1, 8, 15, 22) HA-hydrogel-Aib-linker conjugate with peptide of SEQ ID NO: 5.

Figure 6:
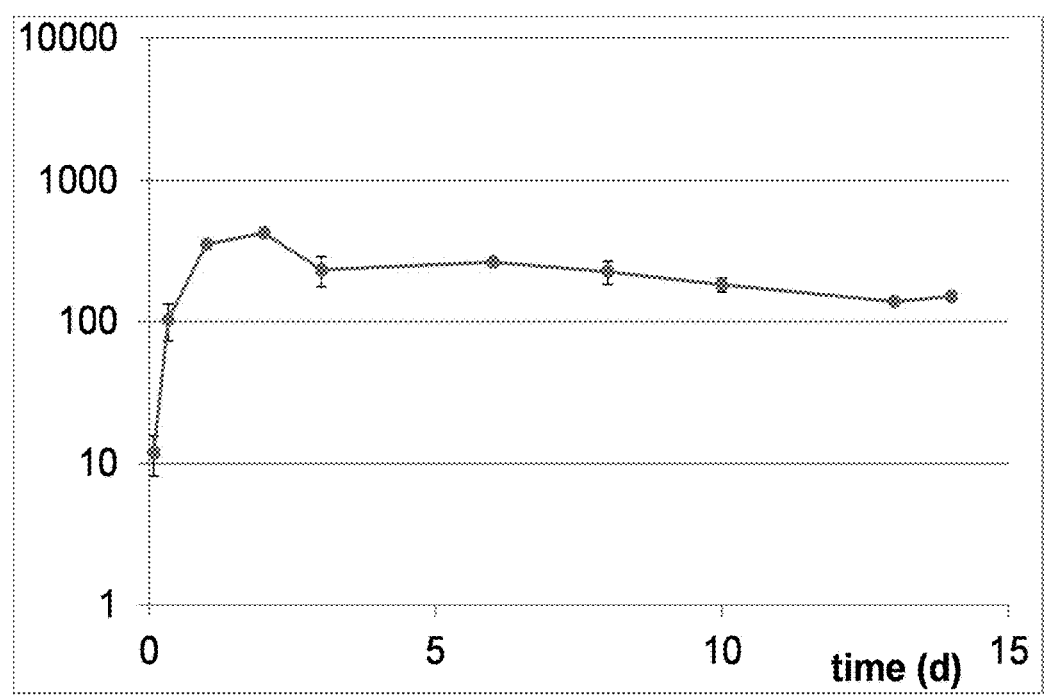

FIG. 6: Plasma concentrations of peptide of Seq. NO: 5 after single subcutaneous administration of 4.5 mg/kg of HA-Aib-linker-conjugate to female C57BL/6 mice.

Figure 7:
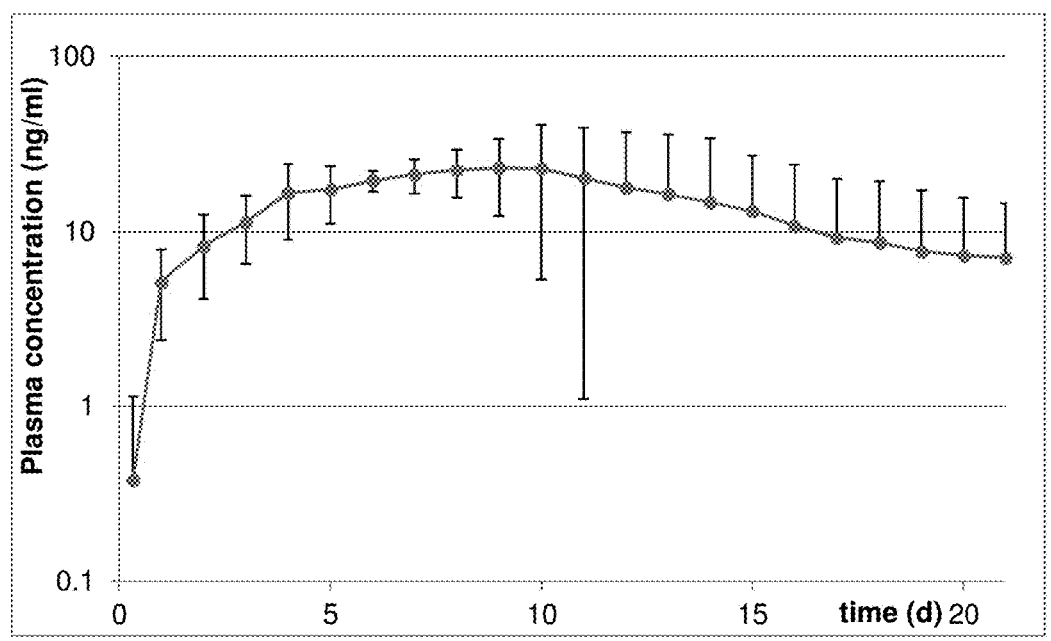

FIG. 7: Plasma concentrations of peptide of Seq. NO: 5 after single subcutaneous administration of 0.623 mg/kg in suspension (16.05%) as HA-Aib-linker-conjugate to female Göttingen minipigs.

Figure 8:
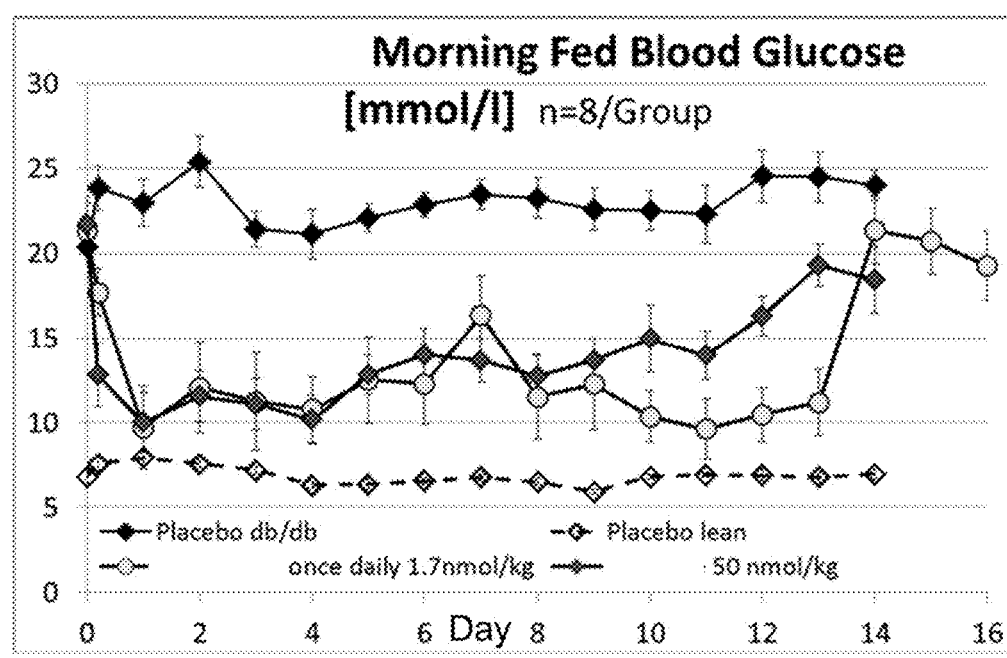

FIG. 8. Fed blood glucose profile in male db/db mice: Single s.c. treatment with 50 nmol/kg crosslinked HA conjugate of SEQ ID NO: 5 and once daily s.c. treatment with 1.7 nmol/kg pure peptide of SEQ ID NO: 5

DETAILED DESCRIPTION

The GLP-1/Glucagon agonist bound to a linker-L$^2$- is referred to as "GLP-1/Glucagon agonist moiety".

"Protective groups" refers to a moiety which temporarily protects a chemical functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

"Protected functional groups" means a chemical functional group protected by a protective group.

"Acylating agent" means a moiety of the structure R—(C═O)—, providing the acyl group in an acylation reaction, optionally connected to a leaving group, such as acid chloride, N-hydroxy succinimide, pentafluorphenol and para-nitrophenol.

"Alkyl" means a straight-chain or branched carbon chain. Each hydrogen of an alkyl carbon may be replaced by a substituent.

"Alkylene" means a straight-chain or branched carbon chain. wherein two moieties of a molecule are linked to the alkylene group. Each hydrogen of an alkylene carbon may be replaced by a substituent.

"Aryl" refers to any substituent derived from a monocyclic or polycyclic or fused aromatic ring, including heterocyclic rings, e.g. phenyl, thiophene, indolyl, napthyl, pyridyl, which may optionally be further substituted.

"Acyl" means a chemical functional group of the structure R—(C═O)—, wherein R is an alkyl or aryl.

"C$_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a C$_{1-4}$ alkyl carbon may be replaced by a substituent.

"C$_{1-6}$ alkylene" means an alkyl chain having 1-6 carbon atoms, wherein two moieties of a molecule are linked to the alkylene group, e.g. —CH$_2$—, —CH$_2$—CH$_2$—, —CH(CH$_3$)—, —CH$_2$—OH$_2$—CH$_2$—, —CH(C$_2$H$_5$)—, —C(CH$_3$)$_2$—. Each hydrogen of a C$_{1-6}$ alkyl carbon may be replaced by a substituent.

Accordingly, "C$_{1-18}$ alkyl" means an alkyl chain having 1 to 18 carbon atoms and "C$_{8-18}$ alkyl" means an alkyl chain having 8 to 18 carbon atoms. Accordingly, "C$_{1-50}$ alkyl" means an alkyl chain having 1 to 50 carbon atoms.

"Halogen" means fluoro, chloro, bromo or iodo. It is generally preferred that halogen is fluoro or chloro.

"Hyaluronic acid" means a polymer of a disaccharide composed of beta-1,3-D-glucuronic acid and beta-1,4-N-acetyl-D-glucosamine and their respective sodium salts. These polymers are linear.

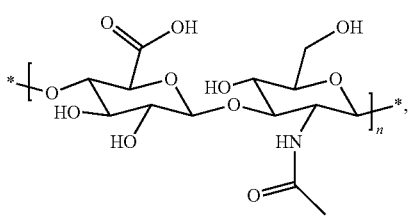

"Disaccharide unit" means the disaccharide composed of beta-1,3-D-glucuronic acid and beta-1,4-N-acetyl-D-glucosamine and their respective sodium salts and is the monomeric building block for HA.

"Crosslinked hyaluronic acid" means a polymer of hyaluronic acid" wherein different chains of HA are covalently connected by a crosslinker, forming a 3-dimensional polymer network. The degree of crosslinking refers the molar ratio of disaccharide units to crosslinker units in the polymer network.

"Crosslinker" may be a linear or branched molecule or chemical group, preferably is a linear molecule with at least chemical functional groups on each distal ends.

"Functionalized hyaluronic acid" means a polymer of hyaluronic acid" wherein HA is chemically modified with a group $L^1$ which bears a chemical functional chemical group at its distal end. The degree of functionalization refers the molar ratio of disaccharide units to $L^1$ units in the polymer.

The term "chemical functional group" refers to but not limited to carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine.

If a chemical functional group is coupled to another chemical functional group, the resulting chemical structure is referred to as "linkage". For example, the reaction of an amine group with a carboxyl group results in an amide linkage.

"Reactive functional groups" are chemical functional groups of the backbone moiety, which are connected to the hyperbranched moiety.

"Functional group" is the collective term used for "reactive functional group", "degradable interconnected functional group", or "conjugate functional group".

The terms "blocking group" or "capping group" are used synonymously and refer to moieties which are irreversibly connected to reactive functional groups to render them incapable of reacting with for example chemical functional groups.

The terms "protecting group" or "protective group" refers to a moiety which is reversibly connected to reactive functional groups to render them incapable of reacting with for example other chemical functional groups under specific conditions.

The term "activation group" refers to chemical functional groups suitably to activate forms of a corresponding chemical functional group which are known to the person skilled in the art. For example, activated forms of carboxyl groups include but are not limited to active esters, such as succinimidyl ester, benzotriazyl ester, nitrophenyl ester, pentafluorophenyl ester, azabenzotriazyl ester, acyl halogenides, mixed or symmetrical anhydrides, acyl imidazole.

The term "non-enzymatically cleavable linker" refers to linkers that are hydrolytically degradable under physiological conditions without enzymatic activity.

The terms "spacer", "spacer group", "spacer molecule", and "spacer moiety" are used interchangeably and if used to describe a moiety present in the hydrogel carrier of the invention, refer to any moiety suitable for connecting two moieties, such as $C_{1-50}$ alkyl, which fragment is optionally interrupted by one or more groups selected from —NH—, —N($C_{1-4}$ alkyl)-, —O—, —S—, —C(O)—, —C(O)NH—, —C(O)N($C_{1-4}$alkyl)-, —O—C(O)—, —S(O)—, —S(O)$_2$—.

The terms "terminal", "terminus" or "distal end" refer to the position of a functional group or linkage within a molecule or moiety, whereby such functional group may be a chemical functional group and the linkage may be a degradable or permanent linkage, characterized by being located adjacent to or within a linkage between two moieties or at the end of an oligomeric or polymeric chain.

The phrases "in bound form" or "moiety" refer to substructures which are part of a larger molecule. The phrase "in bound form" is used to simplify reference to moieties by naming or listing reagents, starting materials or hypothetical starting materials well known in the art, and whereby "in bound form" means that for example one or more hydrogen radicals (—H), or one or more activating or protecting groups present in the reagents or starting materials are not present in the moiety.

It is understood that all reagents and moieties comprising polymeric moieties refer to macromolecular entities known to exhibit variabilities with respect to molecular weight, chain lengths or degree of polymerization, or the number of functional groups. Structures shown for crosslinking reagents, and crosslinked moieties are thus only representative examples.

A reagent or moiety may be linear or branched. If the reagent or moiety has two terminal groups, it is referred to as a linear reagent or moiety. If the reagent or moiety has more than two terminal groups, it is considered to be a branched or multi-functional reagent or moiety.

The linkers used in the conjugates of the invention are transient, meaning that they are non-enzymatically hydrolytically degradable (cleavable) under physiological conditions (aqueous buffer at pH 7.4, 37° C.) with half-lives ranging from, for example, one hour to three months.

The term "GLP-1/Glucagon agonist hydrogel conjugate" refers to carrier-linked conjugates of GLP-1/Glucagon agonist, wherein the carrier is a hydrogel. The terms "hydrogel conjugate" and "hydrogel-linked conjugate" refer to conjugates of biologically active agents transiently linked to a hydrogel and are used synonymously.

A "hydrogel" may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

"Free form" of a drug refers to a drug, specifically to GLP-1/Glucagon agonist, in its unmodified, pharmacologically active form, such as after being released from a polymer conjugate.

The terms "drug", "biologically active molecule", "biologically active moiety", "biologically active agent", "active agent", are used synonymously and refer to GLP-1/Glucagon agonist, either in its bound or free form.

A "therapeutically effective amount" of GLP-1/Glucagon agonist as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which are all within the ordinary skills of a trained physician.

"Stable" and "stability" means that within the indicated storage time the hydrogel conjugates remain conjugated and do not hydrolyze to a substantial extent and exhibit an acceptable impurity profile relating to GLP-1/Glucagon agonist. To be considered stable, the composition contains less than 5% of the drug in its free form.

The term "pharmaceutically acceptable" means approved by a regulatory agency such as the EMEA (Europe) and/or the FDA (US) and/or any other national regulatory agencies for use in animals, preferably in humans.

"Pharmaceutical composition" or "composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient (pharmaceutically acceptable carrier).

"Dry composition" means that the GLP-1/Glucagon agonist hydrogel conjugate composition is provided in a dry form in a container. Suitable methods for drying are for example spray-drying and lyophilization (freeze-drying). Such dry composition of GLP-1/Glucagon agonist hydrogel conjugate has a residual water content of a maximum of 10%, preferably less than 5% and more preferably less than 2% (determined according to Karl Fischer method). The preferred method of drying is lyophilization. "Lyophilized composition" means that the GLP-1/Glucagon agonist hydrogel conjugate composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the addition of a liquid to a dry composition to bring it into the form of a liquid or suspension composition. It is understood that the term "reconstitution" is not limited to the addition of water, but refers to the addition of any liquid, including for example buffers or other aqueous solutions.

"Reconstitution solution" refers to the liquid used to reconstitute the dry composition of an GLP-1/Glucagon agonist hydrogel conjugate prior to administration to a patient in need thereof.

"Container" means any container in which the GLP-1/Glucagon agonist hydrogel conjugate composition is comprised and can be stored until reconstitution.

"Buffer" or "buffering agent" refers to chemical compounds that maintain the pH in a desired range. Physiologically tolerated buffers are, for example, sodium phosphate, succinate, histidine, bicarbonate, citrate and acetate, pyruvate. Antacids such as $Mg(OH)_2$ or $ZnCO_3$ may be also used. Buffering capacity may be adjusted to match the conditions most sensitive to pH stability.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as arginine, glycine, glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the conjugate of the invention. Stabilisation is achieved by strengthening of the protein-stabilising forces, by destabilisation of the denatured state, or by direct binding of excipients to the protein.

"Anti-adsorption agents" refers to mainly ionic or non-ionic surfactants or other proteins or soluble polymers used to coat or adsorb competitively to the inner surface of the composition's container. Chosen concentration and type of excipient depends on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin E, chelating agents such aus citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"Sealing a container" means that the container is closed in such way that it is airtight, allowing no gas exchange between the outside and the inside and keeping the content sterile.

The term "reagent" or "precursor" refers to an intermediate or starting material used in the assembly process leading to a conjugate of the present invention.

In another embodiment of the conjugate
-L$^1$-L$^2$-L- is a linker moiety of formula (IIa),

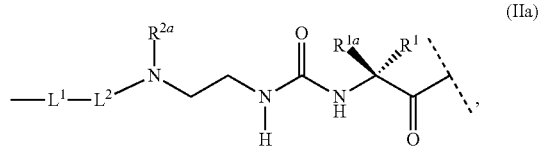

(IIa)

wherein the dashed line indicates attachment to Y by forming an amide bond;
R$^1$, R$^{1a}$, R$^{2a}$ are selected independently from the group consisting of H and C$_{1-4}$ alkyl;
-L$^1$-L$^2$- is defined as described above.

In another embodiment of the conjugate
-L$^1$-L$^2$-L- is a linker moiety of formula (IIa), wherein
R$^1$ is CH$_3$;
R$^{1a}$ is H;
R$^{2a}$ is H; and
-L$^1$-L$^2$- is defined as described above.

In another embodiment of the conjugate
-L$^1$-L$^2$-L- is a linker moiety of formula (IIa), wherein
R$^1$ is H;
R$^{1a}$ is CH$_3$;
R$^{2a}$ is H; and
-L$^1$-L$^2$- is defined as described above.

In another embodiment of the conjugate
-L$^1$-L$^2$-L- is a linker moiety of formula (IIa), wherein
R$^1$ is CH$_3$;
R$^{1a}$ is CH$_3$;
R$^{2a}$ is H; and
-L$^1$-L$^2$- is defined as described above.

In another embodiment of the conjugate
-L$^1$-L$^2$-L- is a linker moiety of formula (IIb),

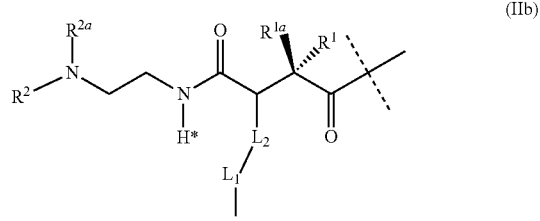

(IIb)

wherein the dashed line indicates attachment to Y by forming an amide bond;
R$^1$ is selected from H or C$_{1-4}$ alkyl, preferably H;
R$^{1a}$ is selected from H or C$_{1-4}$ alkyl, preferably H;
R$^2$, R$^{2a}$ are independently selected from the group consisting of H and C$_{1-4}$ alkyl;
wherein -L$^1$-L$^2$- is defined as described above.

In another embodiment of the conjugate
-L$^1$-L$^2$-L is a linker moiety of formula (IIb),

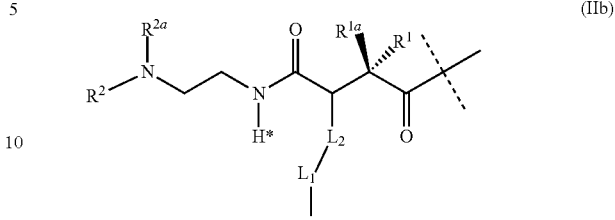

(IIb)

wherein the dashed line indicates attachment to Y by forming an amide bond;
R$^1$ and R$^{1a}$ are H;
R$^2$, R$^a$ are independently selected from the group consisting of H and CH$_3$;
wherein -L$^1$-L$^2$- is defined as described above.

In another embodiment of the conjugate
-L$^1$-L$^2$-L- is a linker moiety -L of formula (IIb), wherein
R$^1$ and R$^{1a}$ are H;
R$^2$ is H and R$^{2a}$ is CH$_3$;
wherein -L$^1$-L$^2$- is defined as described above.

In another embodiment of the conjugate
L$^2$ is a C$_{1-10}$ alkyl chain, in which optionally one or two carbon atoms are independently replaced by a group selected from —O— and C(O)N(R$^{3aa}$) and, wherein R$^{3aa}$ is independently selected from the group consisting of H and C$_{1-4}$ alkyl; and
L$^2$ is attached to L$^1$ via a terminal group selected from the group consisting of

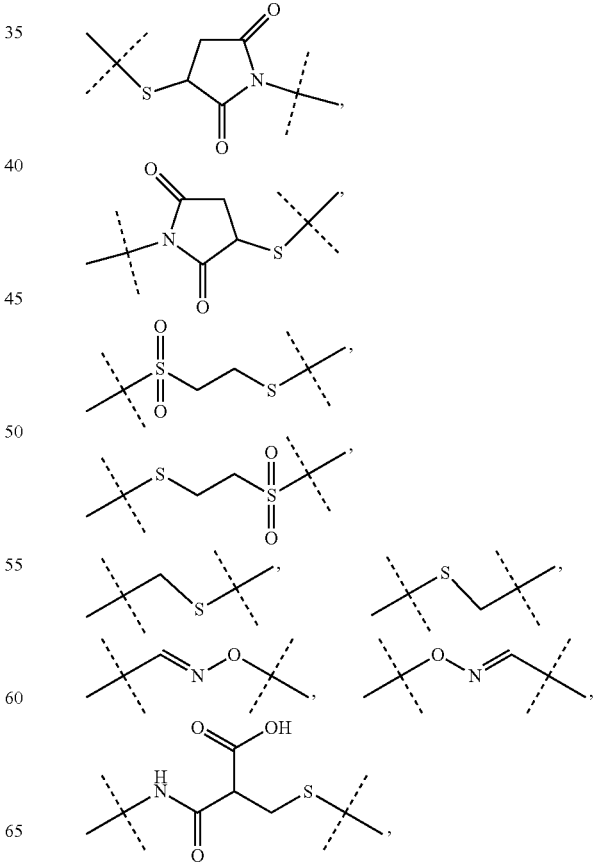

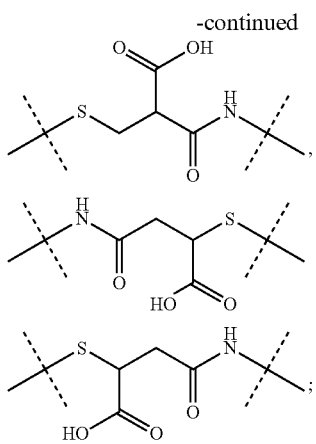

wherein L² is attached to the one position indicated with the dashed line and L¹ is attached to the position indicated with the other dashed line.

In another embodiment of the conjugate

L² is a $C_{1-6}$ alkyl chain, in which optionally one carbon atoms is independently replaced by a group selected from —O— and $C(O)N(R^{3aa})$ and, wherein $R^{3aa}$ is independently selected from the group consisting of H and $C_{1-4}$ alkyl; and L² is attached to L¹ via a terminal group selected from the group consisting of

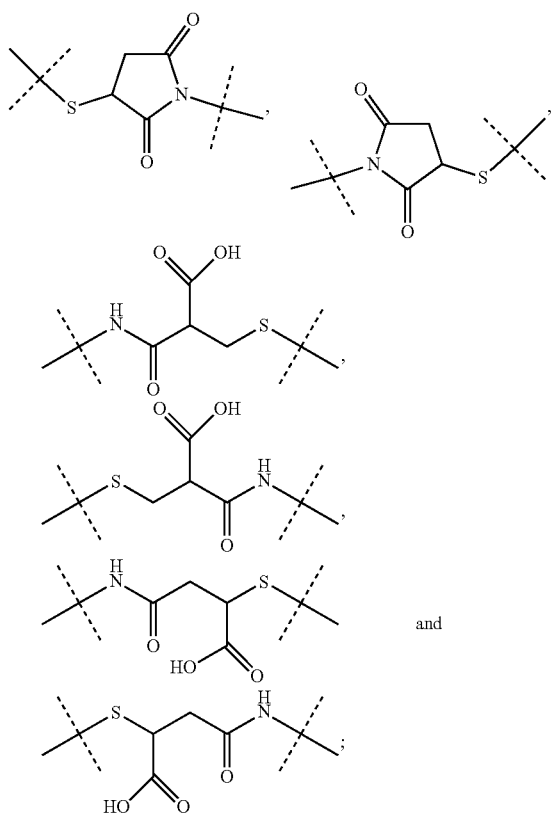

wherein L² is attached to the one position indicated with the dashed line and L¹ is attached to the position indicated with the other dashed line.

In another embodiment of the conjugate

L² is —$CH_2$—$CH_2$—$CH_2$—$CH_2$—$CH_2$—C(O)NH— or —$CH_2$—$CH_2$—$CH_2$—$CH_2$—$CH_2$—$CH_2$— and is attached to L¹ via the terminal group

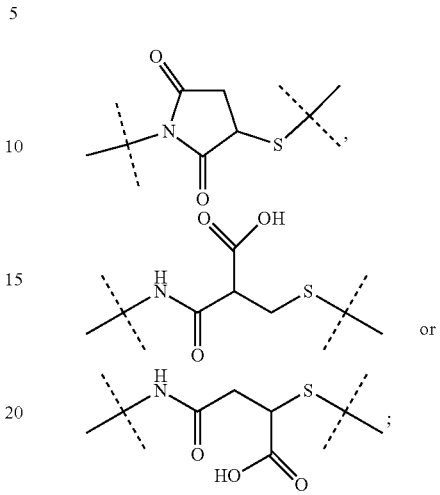

wherein L² is attached to the Sulfur atom indicated with the dashed line and L¹ is attached to nitrogen atom indicated with the dashed line.

In another embodiment of the conjugate

L² is —$CH_2$—$CH_2$—$CH_2$—$CH_2$—$CH_2$—C(O)NH— or —$CH_2$—$CH_2$—$CH_2$—$CH_2$—$CH_2$—$CH_2$— and is attached to L¹ via the terminal group

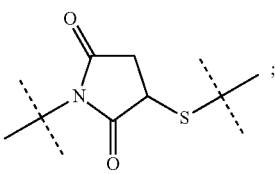

wherein L² is attached to the Sulfur atom indicated with the dashed line and L¹ is attached to nitrogen atom indicated with the dashed line.

In another embodiment of the conjugate

L¹ is a $C_{1-10}$ alkyl chain, with an amino group on one distal end, which is optionally interrupted by one or two groups independently selected from —O— and $C(O)N(R^{5aa})$ and, wherein $R^{5aa}$ is independently selected from the group consisting of H and $C_{1-4}$ alkyl.

A further embodiment relates to conjugates, wherein the crosslinker is divinylsulfone.

A further embodiment relates to conjugates, wherein 0.001 to 15 mol % of the monomeric disaccharide units are crosslinked by a crosslinker in the crosslinked hyaluronic acid hydrogel.

A further embodiment relates to conjugates, wherein 0.1 to 5 mol % of the monomeric disaccharide units are crosslinked by a crosslinker in crosslinked hyaluronic acid hydrogel.

A further embodiment relates to conjugates, wherein 0.2 to 10 mol % of the monomeric disaccharide units of the crosslinked hyaluronic acid hydrogel bear -L¹-L²-L-Y—R²⁰ groups.

A further embodiment relates to conjugates, wherein 0.5 to 7 mol % of the monomeric disaccharide units of the crosslinked hyaluronic acid hydrogel bear -L¹-L²-L-Y—R²⁰ groups.

A further embodiment relates to conjugates, wherein 0.5 to 5 mol % of the monomeric disaccharide units of the crosslinked hyaluronic acid hydrogel bear -L$^1$-L$^2$-L-Y—R$^{20}$ groups.

A further embodiment relates to conjugates, wherein 1 to 3.5 mol % of the monomeric disaccharide units of the crosslinked hyaluronic acid hydrogel bear -L$^1$-L$^2$-L-Y—R$^{20}$ groups.

An further embodiment is a conjugate or a pharmaceutically acceptable salt thereof comprising a
crosslinked hyaluronic acid hydrogel, in which
0.001 to 20 mol % of the monomeric disaccharide units are crosslinked by a crosslinker; and
0.2 to 20 mol % of the monomeric disaccharide units bear -L$^1$-L$^2$-L-Y—R$^{20}$ groups; and
0.2 to 30 mol % of the monomeric disaccharide units of the crosslinked hyaluronic acid hydrogel bear -L$^1$-Z—OH groups;

L$^1$ is a C$_{1-20}$ alkyl chain, in which optionally one or more carbon atoms are independently replaced by a group selected from —O—, NH(R$^{5aa}$) and C(O)N(R$^{5aa}$) and is optionally substituted with one or more groups independently selected from OH and C(O)N(R$^{5aa}$R$^{5aaa}$), wherein R$^{5aa}$ and R$^{5aaa}$ are independently selected from the group consisting of H and C$_{1-4}$ alkyl; and L$^1$ is attached to the hydrogel via a terminal amino group forming an amide bond with the carboxy group of the beta-1,3-D-glucuronic acid of the hyaluronic acid L$^2$ is a single chemical bond or is a C$_{1-20}$ alkyl chain, in which optionally one or more carbon atoms are independently replaced by a group selected from —O— and C(O)N(R$^{3aa}$) and is optionally substituted with one or more groups independently selected from OH and C(O)N (R$^{3aa}$R$^{3aaa}$, wherein R$^{3aa}$ and R$^{3aaa}$ are independently selected from the group consisting of H and C$_{1-4}$ alkyl; and L$^2$ is attached to L$^1$ via a terminal group selected from the group consisting of

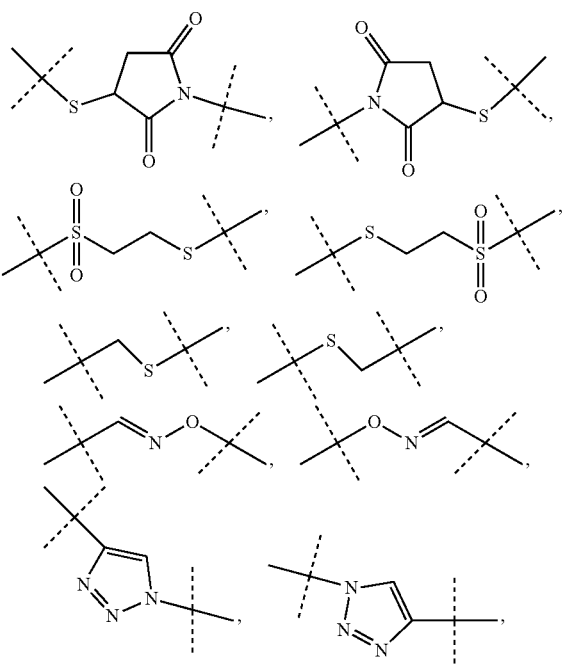

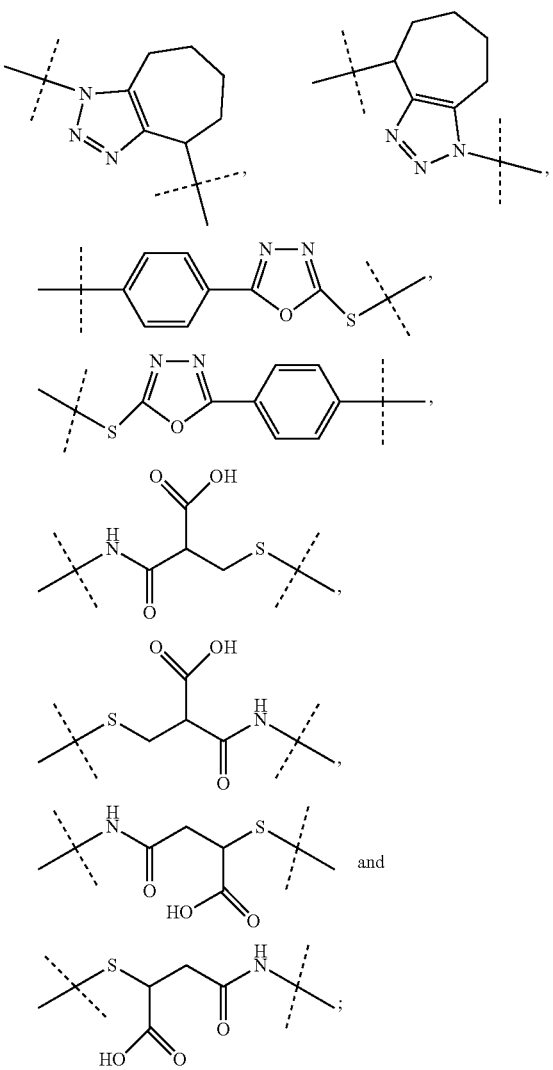

wherein L$^2$ is attached to the one position indicated with the dashed line and L$^1$ is attached to the position indicated with the other dashed line;

Z is a C$_{1-16}$ alkyl chain, in which optionally one or more carbon atoms are independently replaced by a group selected from —O— and C(O)N(R$^{6aa}$); wherein R$^{6aa}$ is hydrogen or C$_{1-4}$-alkyl; or Z is

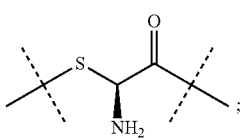

and

Z is attached to L$^1$ via a terminal group selected from the group consisting of

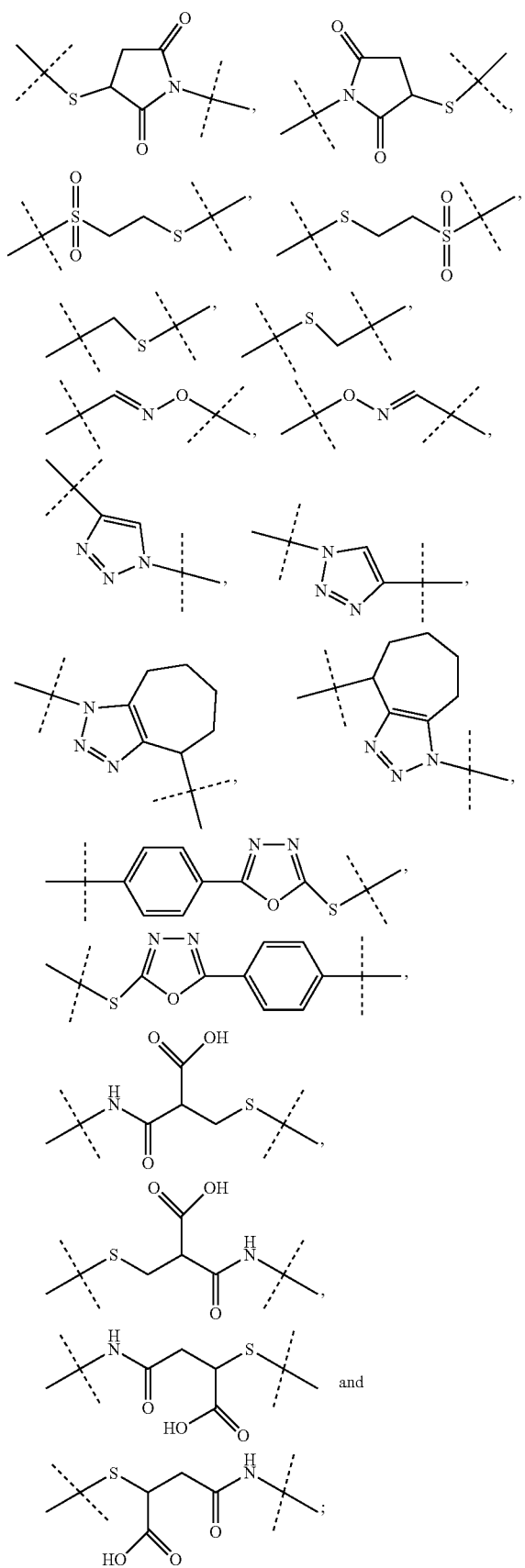

wherein Z is attached to the one position indicated with the dashed line and $L^1$ is attached to the position indicated with the other dashed line;

L is a linker of formula (Ia),

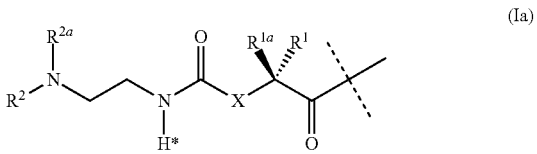

(Ia)

wherein the dashed line indicates the attachment to the N-Terminus of Y by forming an amide bond;

X is $C(R^4R^{4a})$ or $N(R^4)$;

$R^1$, $R^{1a}$, are independently selected from the group consisting of H; and $C_{1-4}$ alkyl;

$R^2$, $R^{2a}$, are independently selected from the group consisting of H; and $C_{1-4}$ alkyl;

$R^4$, $R^{4a}$, are independently selected from the group consisting of H; and $C_{1-4}$ alkyl;

wherein one of $R^2$, $R^{2a}$, $R^4$ or $R^{4a}$ is attached to $L^2$;

Y is a peptide moiety having the formula (Ib)

```
His-D-Ser-Gln-Gly-Thr-Phe-Thr-Ser-Asp-Leu-Ser-Lys-

Gln-X14-Glu-Ser-Lys-Ala-Ala-Gln-Asp-Phe-Ile-Glu-

Trp-Leu-Lys-Ala-Gly-Gly-Pro-Ser-Ser-Gly-Ala-Pro-

Pro-Pro-Ser (Ib)
``` wherein X14 represents Lys, wherein the —$NH_2$ side chain group is functionalized by (S)-4-carboxy-4-hexadecanoylamino-butyryl;

or Y is a peptide moiety having the formula (Ic)

```
His-dSer-Gln-Gly-Thr-Phe-Thr-Ser-Asp-Leu-Ser-Lys-

Gln-X14-Asp-Glu-Gln-Leu-Ala-Lys-Asp-Phe-Ile-Glu-

Trp-Leu-Lys-Ala-Gly-Gly-Pro-Ser-Ser-Gly-Ala-Pro-

Pro-Pro-Ser (Ic)
``` wherein X14 represents Lys, wherein the —$NH_2$ side chain group is functionalized by (S)-4-carboxy-4-octadecanoylamino-butyryl;

$R^{20}$ is OH or $NH_2$.

An further embodiment is a conjugate or a pharmaceutically acceptable salt thereof comprising a crosslinked hyaluronic acid hydrogel as described above, wherein 0.2 to 20 mol % of the monomeric disaccharide units of the crosslinked hyaluronic acid hydrogel bear -$L^1$-Z—OH groups.

An further embodiment is a conjugate or a pharmaceutically acceptable salt thereof comprising a crosslinked hyaluronic acid hydrogel as described above, wherein 0.2 to 10 mol % of the monomeric disaccharide units of the crosslinked hyaluronic acid hydrogel bear -$L^1$-Z—OH groups.

An further embodiment is a conjugate or a pharmaceutically acceptable salt thereof comprising a crosslinked hyaluronic acid hydrogel as described above, wherein the crosslinked hyaluronic acid hydrogel bear -$L^1$-Z—OH groups and wherein Z is a $C_{1-16}$ alkyl chain, in which optionally one or more carbon atoms are independently replaced by a group selected from —O— and $C(O)N(R^{6aa})$; or Z is

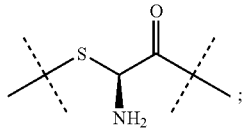

and

Z is attached to $L^1$ via a terminal group selected from the group consisting of

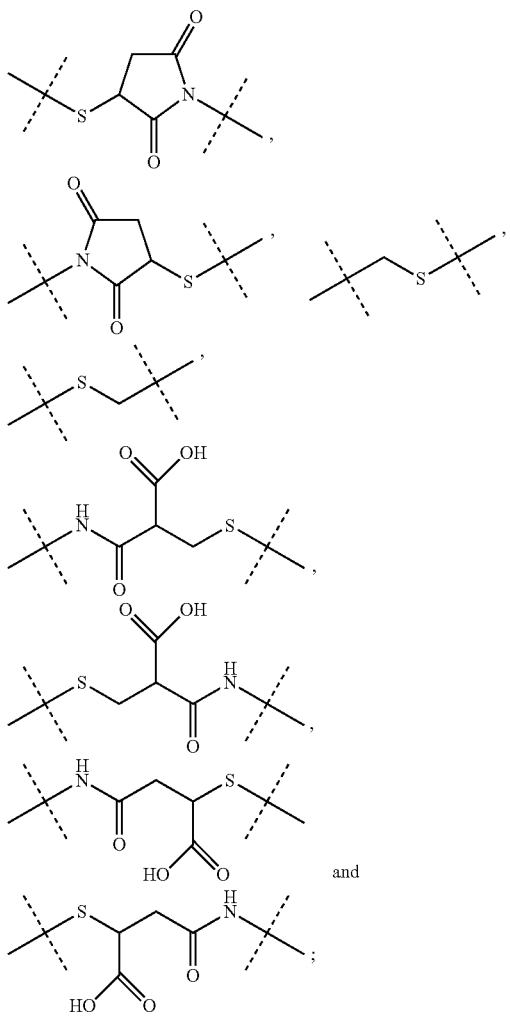

and wherein Z is attached to the one position indicated with the dashed line and $L^1$ is attached to the position indicated with the other dashed line.

An further embodiment is a conjugate or a pharmaceutically acceptable salt thereof comprising a crosslinked hyaluronic acid hydrogel as described above, wherein the crosslinked hyaluronic acid hydrogel bear -$L^1$-Z—OH groups and wherein Z is a $C_{1-8}$ alkyl chain, in which optionally one or more carbon atoms are independently replaced by a selected from —O—; or Z is

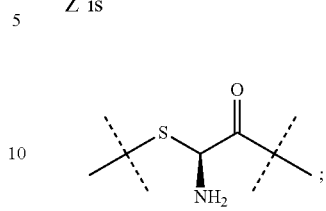

and

Z is attached to $L^1$ via a terminal group selected from the group consisting of

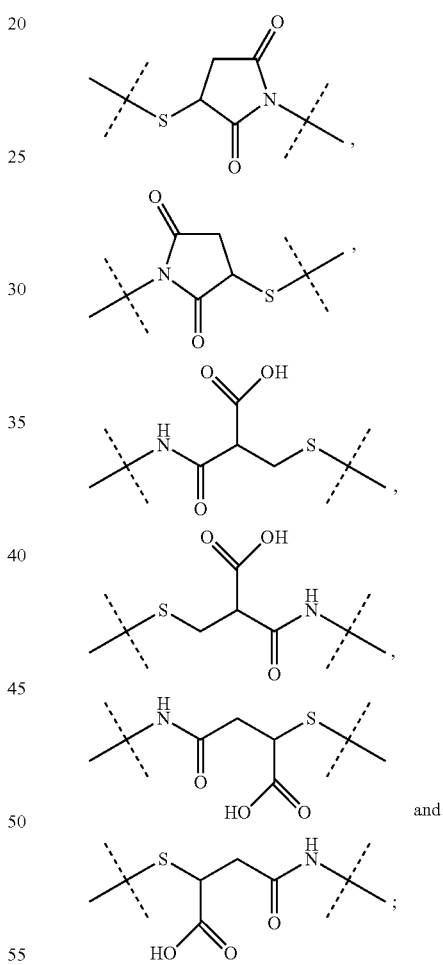

wherein Z is attached to the one position indicated with the dashed line and $L^1$ is attached to the position indicated with the other dashed line.

An further embodiment is a conjugate or a pharmaceutically acceptable salt thereof comprising a crosslinked hyaluronic acid hydrogel as described above, wherein the crosslinked hyaluronic acid hydrogel bear -$L^1$-Z—OH groups and wherein Z is —CH$_2$—CH$_2$—; or
Z is

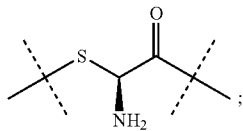

and
Z is attached to L$^1$ via a terminal group selected from the group consisting of

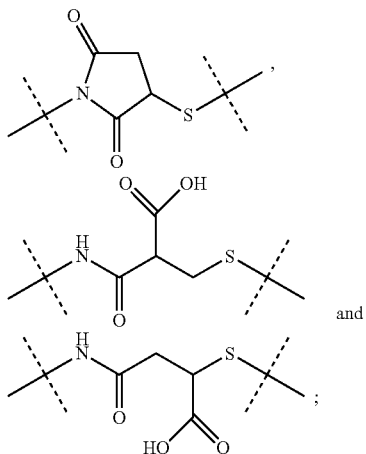

wherein Z is attached to the one position indicated with the dashed line and L$^1$ is attached to the position indicated with the other dashed line.

A further embodiment is a conjugate or a pharmaceutically acceptable salt thereof comprising a crosslinked hyaluronic acid hydrogel as described above, wherein the crosslinked hyaluronic acid hydrogel bear -L$^1$-Z—OH groups and wherein Z is —CH$_2$—CH$_2$—; and Z is attached to L$^1$ via a terminal group selected from the group consisting of

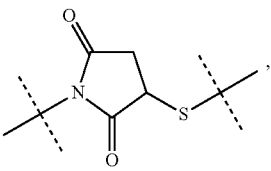

and;

wherein Z is attached to the one position indicated with the dashed line and L$^1$ is attached to the position indicated with the other dashed line.

In another embodiment of the conjugate the -L-L$^1$-L$^2$-L-Y group has a structure as represented by formula (IIIa)

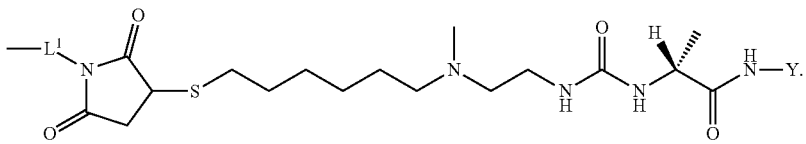

(IIIa)

In another embodiment of the conjugate the -L-L$^1$-L$^2$-L-Y group has a structure as represented by formula (IIIb)

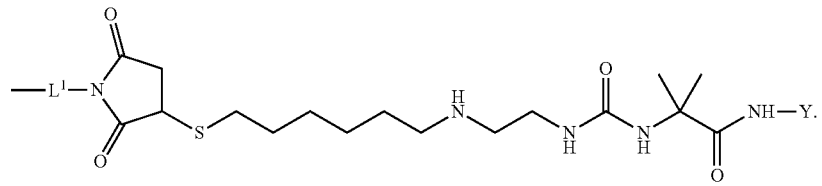

(IIIb)

In another embodiment of the conjugate the -L$^1$-L$^2$-L-Y group has a structure as represented by formula (IIIc)

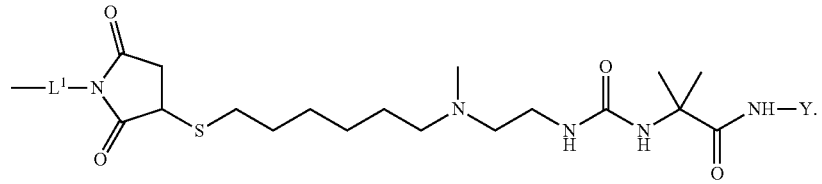

(IIIc)

In another embodiment of the conjugate the -L$^1$-L$^2$-L-Y group has a structure as represented by formula (IIId)

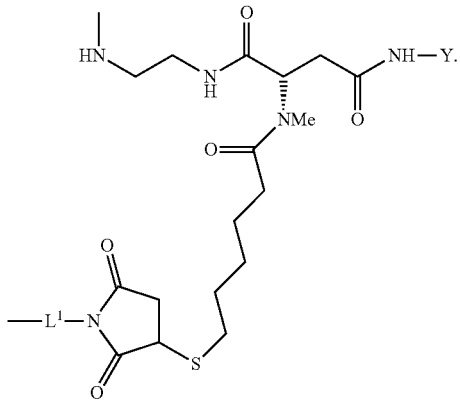

(IIId)

In one embodiment of the conjugate Y refers to an GLP-1/Glucagon agonist selected from sequence ID NO: 5.

In one embodiment of the conjugate Y refers to an GLP-1/Glucagon agonist selected from sequence ID NO: 6.

Another embodiment of the invention is a conjugate or a pharmaceutically acceptable salt thereof, comprising a crosslinked hyaluronic acid hydrogel, in which
0.001 to 20 mol % of the monomeric disaccharide units are crosslinked by divinylsulfone; and
0.5 to 5 mol % of the monomeric disaccharide units bear -L$^1$-L$^2$-L-Y—R$^{20}$ groups;
wherein In the -L$^1$-L$^2$-L-Y group has a structure as represented by formula (IIIb)

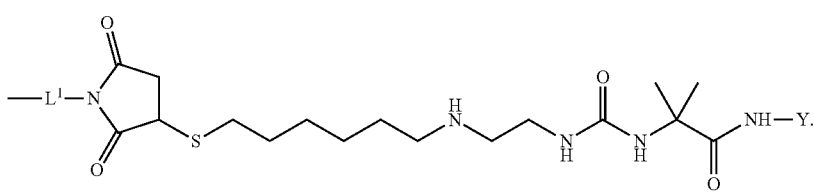

(IIIb)

L$^1$ is a NH—CH$_2$—CH$_2$—CH$_2$—NH—CO—CH$_2$—CH$_2$— or —CH$_2$—CH$_2$—CH$_2$—NH—CO—CH$_2$—CH$_2$—; and L$^1$ is attached to the hydrogel via a terminal amino group forming an amide bond with the carboxy group of the beta-1,3-D-glucuronic acid of the hyaluronic acid; and Y is a peptide moiety having sequence ID NO: 5.

Another embodiment of the invention is a conjugate or a pharmaceutically acceptable salt thereof, comprising a crosslinked hyaluronic acid hydrogel, in which
0.001 to 20 mol % of the monomeric disaccharide units are crosslinked by divinylsulfone; and
0.5 to 5 mol % of the monomeric disaccharide units bear -L$^1$-L$^2$L-Y—R$^{20}$ groups;
wherein In the -L$^1$-L$^2$-L-Y group has a structure as represented by formula (IIIb)

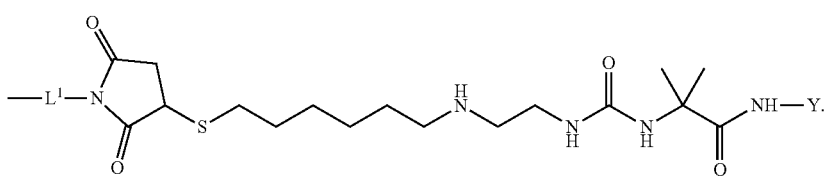

(IIIb)

L$^1$ is a NH—CH$_2$—CH$_2$—CH$_2$—NH—CO—CH$_2$—CH$_2$— or —CH$_2$—CH$_2$—CH$_2$—NH—CO—CH$_2$—CH$_2$—; and L$^1$ is attached to the hydrogel via a terminal amino group forming an amide bond with the carboxy group of the beta-1,3-D-glucuronic acid of the hyaluronic acid; and 0.2 to 30 mol % of the monomeric disaccharide units of the crosslinked hyaluronic acid hydrogel bear -L$^1$-Z—OH groups;

Z is —CH$_2$—CH$_2$—; and

Z is attached to L$^1$ via a terminal group,

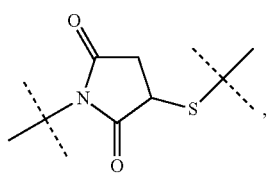

and;

wherein Z is attached to the one position indicated with the dashed line and L$^1$ is attached to the position indicated with the other dashed line;

Y is a peptide moiety having Y is a peptide moiety having sequence ID NO: 5.

TABLE 1

| SEQ ID | sequence |
|---|---|
| 1 | H-G-E-G-T-F-T-S-D-L-S-K-Q-M-E-E-A-V-R-L-F-I-E-W-L-K-N-G-G-P-S-S-G-A-P-P-P-S-NH2 |
| 2 | H-A-E-G-T-F-T-S-D-V-S-S-Y-L-E-G-Q-A-A-K-E-F-I-A-W-L-V-K-G-R-NH2 |
| 3 | H-S-Q-G-T-F-T-S-D-Y-S-K-Y-L-D-S-R-R-A-Q-D-F-V-Q-W-L-M-N-T |
| 4 | H-A-E-G-T-F-T-S-D-V-S-S-Y-L-E-G-Q-A-A-K(γE-x53)-E-I-A-W-L-V-R-G-R-G-OH |

TABLE 1-continued

| SEQ ID | sequence |
|---|---|
| 5 | H-dSer-Q-G-T-F-T-S-D-L-S-K-Q-K(γE-x53)-E-S-K-A-A-Q-D-F-I-E-W-L-K-A-G-G-P-S-S-G-A-P-P-P-S-NH2 |
| 6 | H-dSer-Q-G-T-F-T-S-D-L-S-K-Q-K(γE-x70)-D-E-Q-L-A-K-D-F-I-E-W-L-K-A-G-G-P-S-S-G-A-P-P-P-S-NH2 |

K(γE-x53) represents Lys, wherein the -NH₂ side chain group is functionalized by (S)-4-carboxy-4-hexadecanoylamino-butyryl.
K(γE-x70) represents Lys, wherein the -NH₂ side chain group is functionalized by (S)-4-carboxy-4-octadecanoylamino-butyryl.

In case the conjugates of the invention contain one or more acidic or basic groups, the invention also comprises their corresponding pharmaceutically or toxicologically acceptable salts, in particular their pharmaceutically utilizable salts. Thus, the conjugate of the invention which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. The conjugates of the invention which contain one or more basic groups, i.e. groups which can be protonated, can be present and can be used according to the invention in the form of their addition salts with inorganic or organic acids. If the conjugates of the invention simultaneously contain acidic and basic groups in the molecule, the invention also includes, in addition to the salt forms mentioned, inner salts or betaines (zwitterions). The respective salts according to the conjugate of the invention can be obtained by customary methods which are known to the person skilled in the art like, for example by contacting these with an organic or inorganic acid or base in a solvent or dispersant, or by anion exchange or cation exchange with other salts. The present invention also includes all salts of the conjugate of the invention which, owing to low physiological compatibility, are not directly suitable for use in pharmaceuticals but which can be used, for example, as intermediates for chemical reactions or for the preparation of pharmaceutically acceptable salts.

Process of Making Hyaluronic Acid Hydrogel Synthesis

Crosslinked hyaluronic acid may be derived by different methods. Reaction of HA with the crosslinker, reaction of modified (activated) HA with the crosslinker, the reaction of two different modified HA with the crosslinker. Examples are described in Oh et al, Journal of Controlled Release 141 (2010), 2-12. Example 7 describes the crosslinking of unmodified HA with divinylsulfone which is a mono bifunctional crosslinker as depicted in scheme 1. Crosslinking of unmodified HA with a crosslinker may also achieved by the hydroxyl mediated alkylation (Scheme 2), the Auto crosslinking with 1-methyl, 2-chloro pyridinium iodide (Scheme 3), Amide formation (Scheme 4) and the diol-epoxide chemistry (Scheme 5).

Crosslinking methods starting from two different modified HA's are the Michael addition reaction of thiols with maleiimides (Scheme 6), and the Click chemistries shown in Schemes 7 and 8.

Crosslinking methods starting from modified HA are aldehyde (diol oxidation) (Scheme 9) and 2+2cyclo addition reactions shown in Scheme 10 and 11.

Scheme 1: Crosslinking with Divinyl sulfone

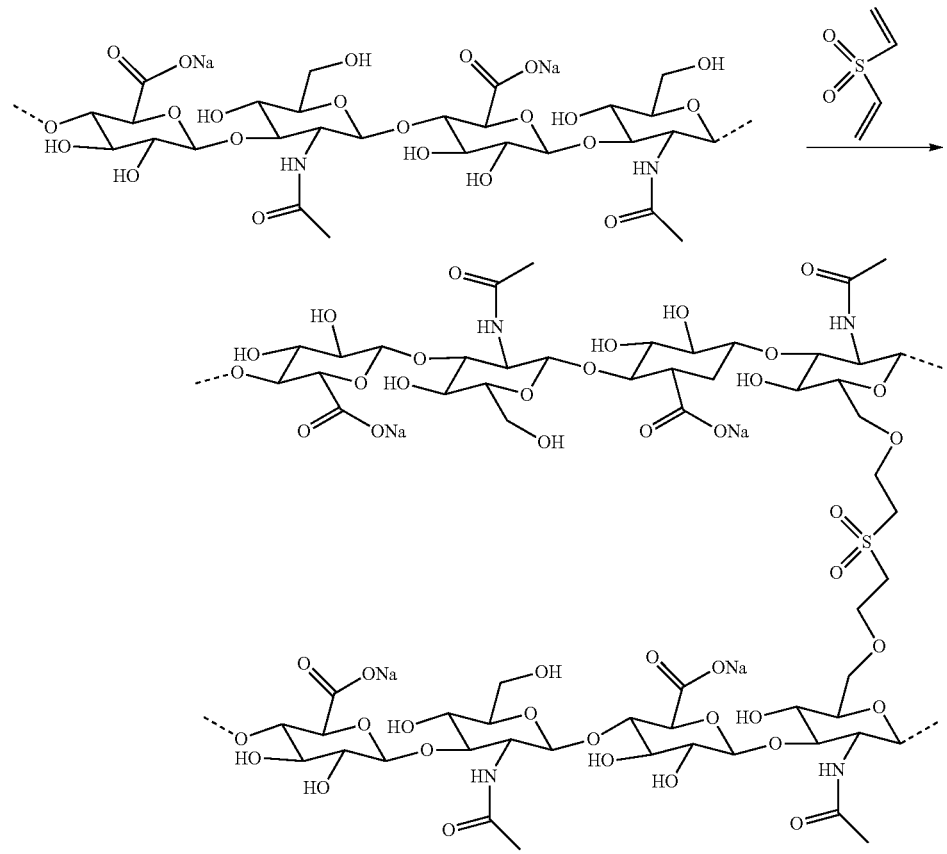

Scheme 2: Hydroxyl mediated alkylation
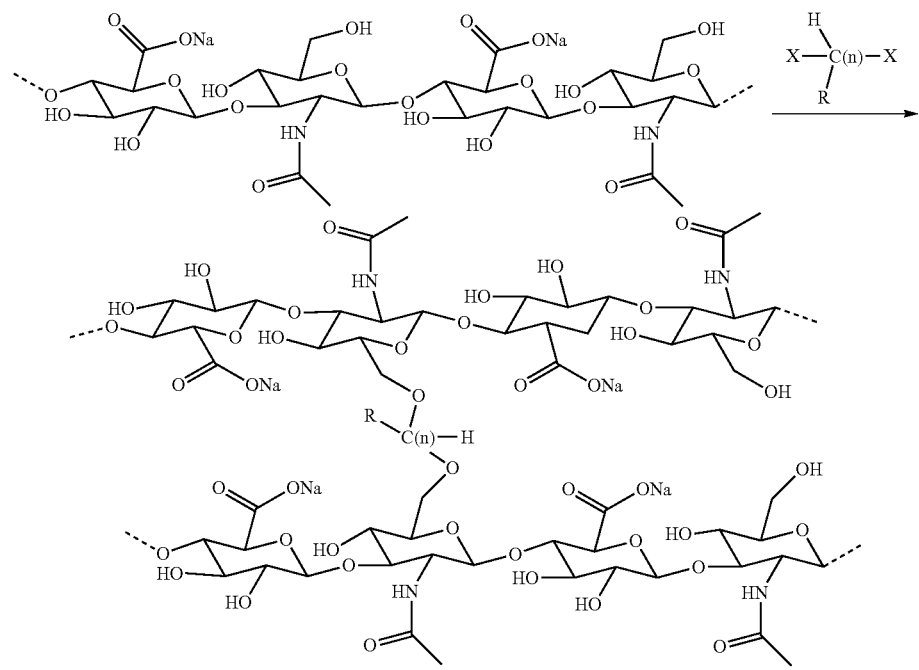
n = 2, 3, 4, etc
R = H, alkyl, aryl
X = halo, sulphonate, other leaving group
Scheme 3: Auto crosslinking
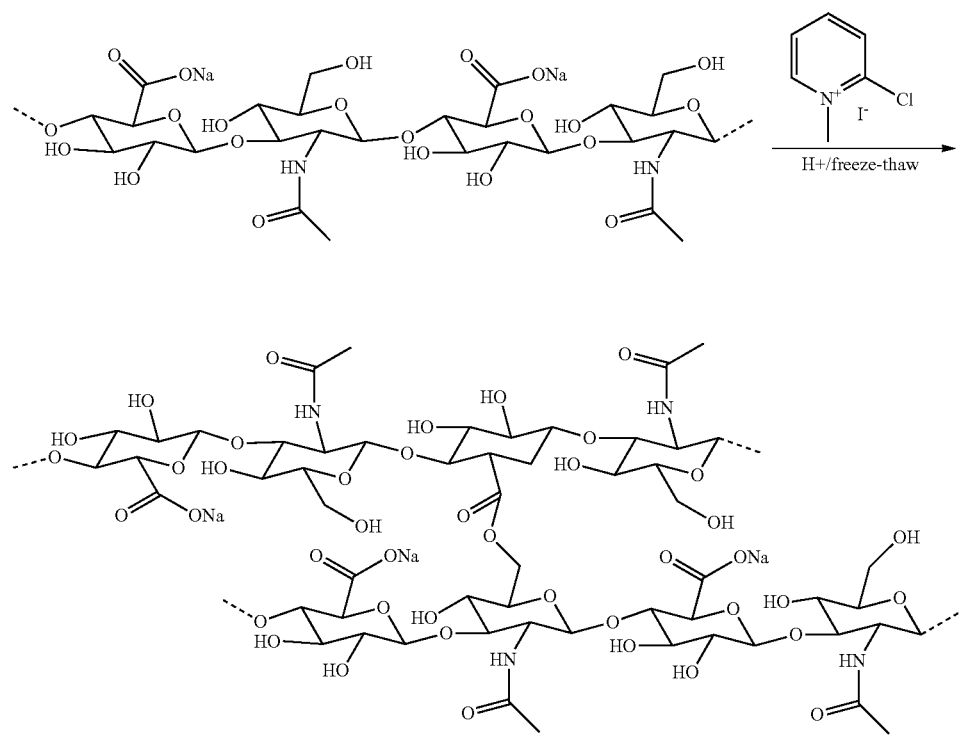

Scheme 4: Amide reaction
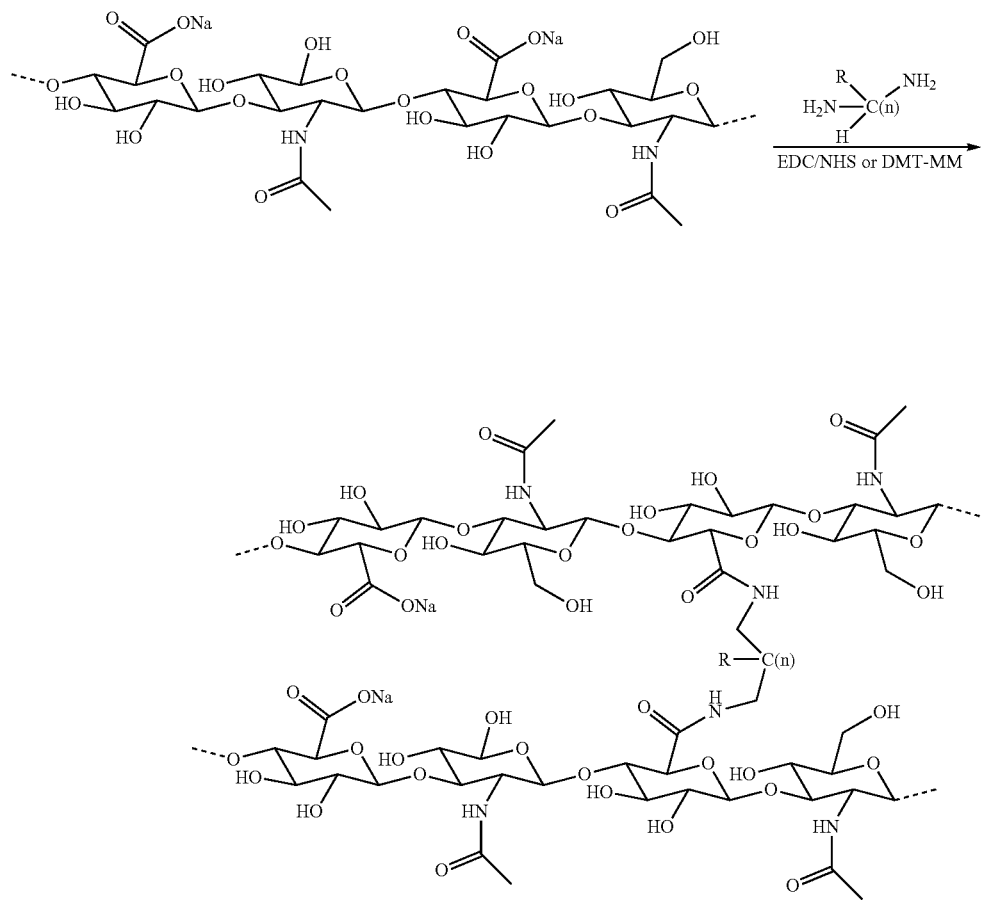
n = 2, 3, 4 etc
R = H, alkyl, aromatic, heteroaromatic diaminoacid ester etc
Scheme 5: Diol-Epoxide Chemistry
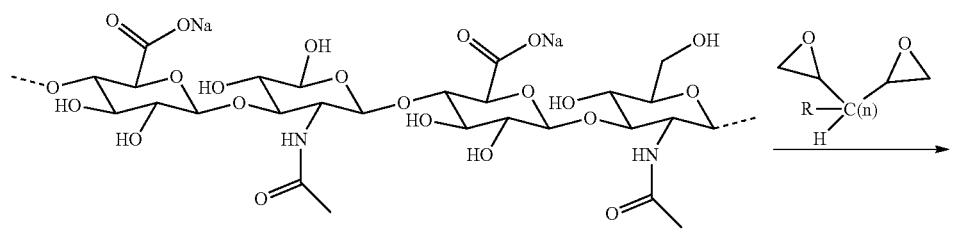

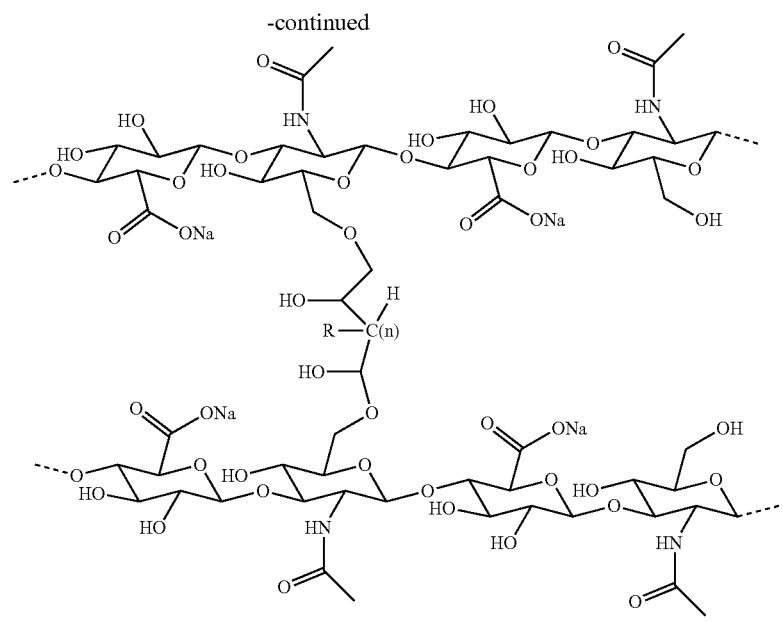
R = H, alkyl, aromatic, heteroaromatic diaminoacid ester etc
n = 0, 1, 2, etc
Scheme 6: Michael Addition Crosslinking (Thiol-maleimide)
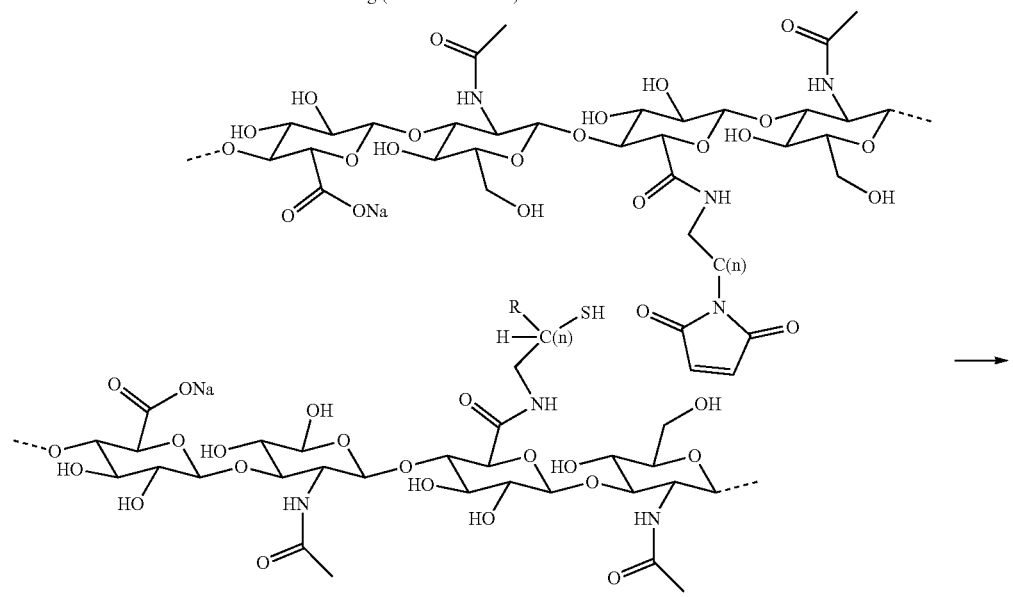

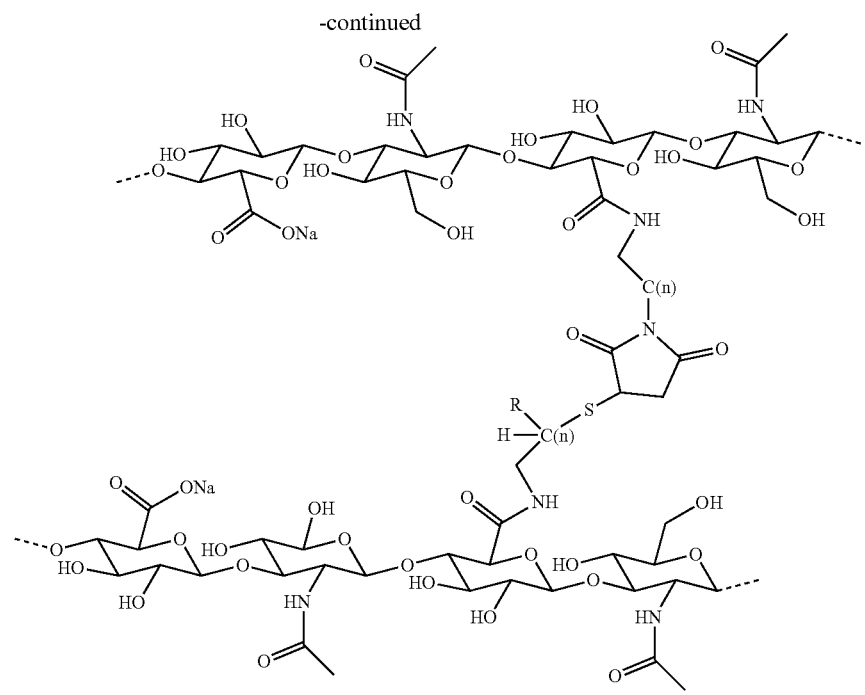
Scheme 7: Click Chemistry
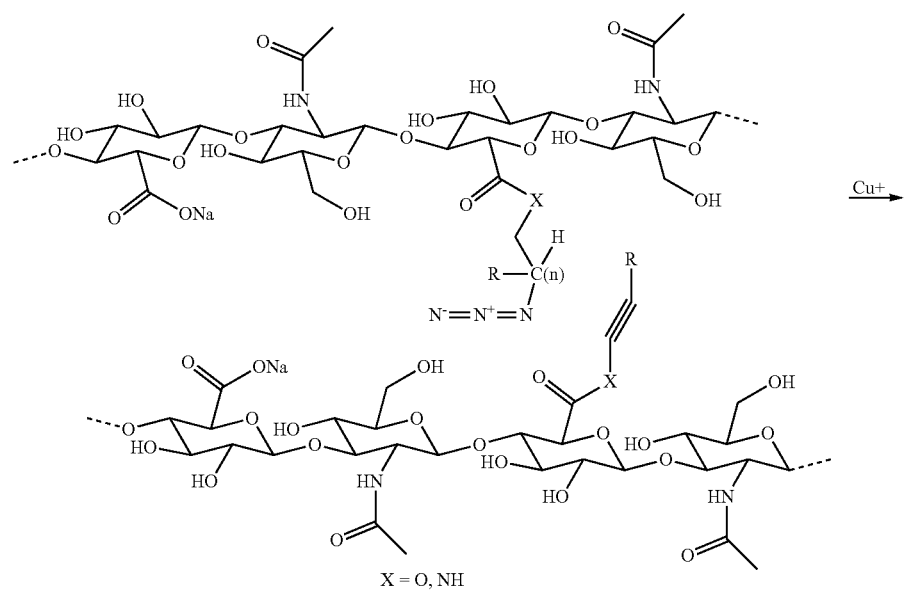
X = O, NH

-continued
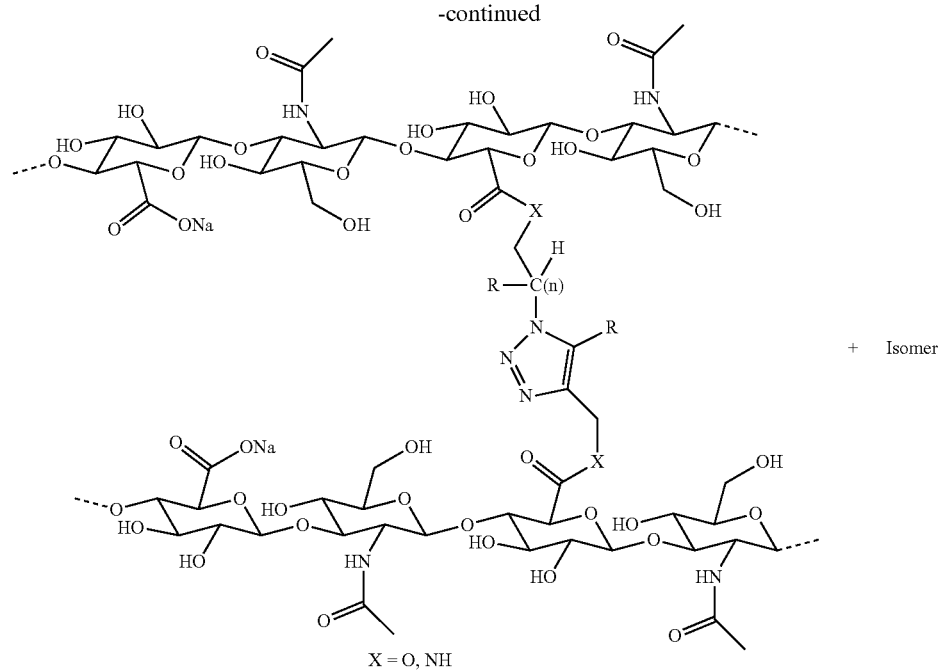
X = O, NH
+ Isomer
Scheme 8: Click Chemistry
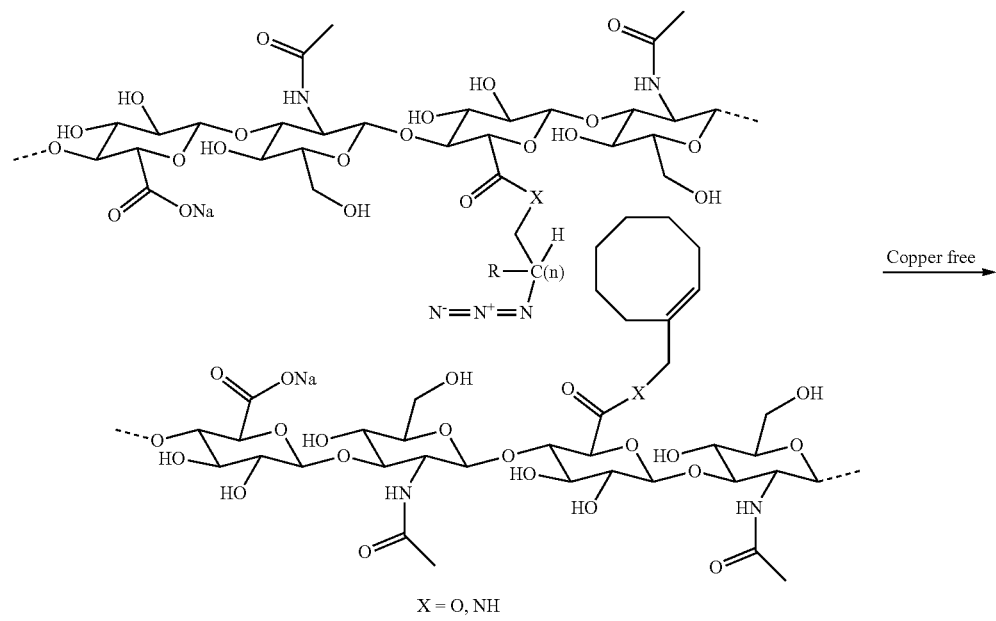
Copper free →
X = O, NH

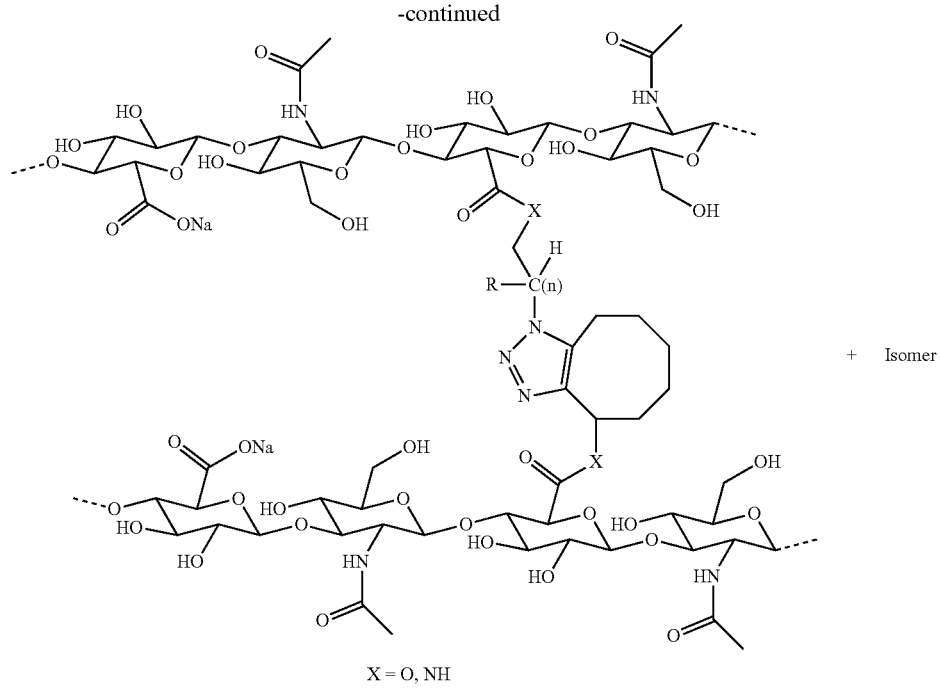
X = O, NH
Scheme 9: Aldehyde (diol oxidation) - amine reductive amination
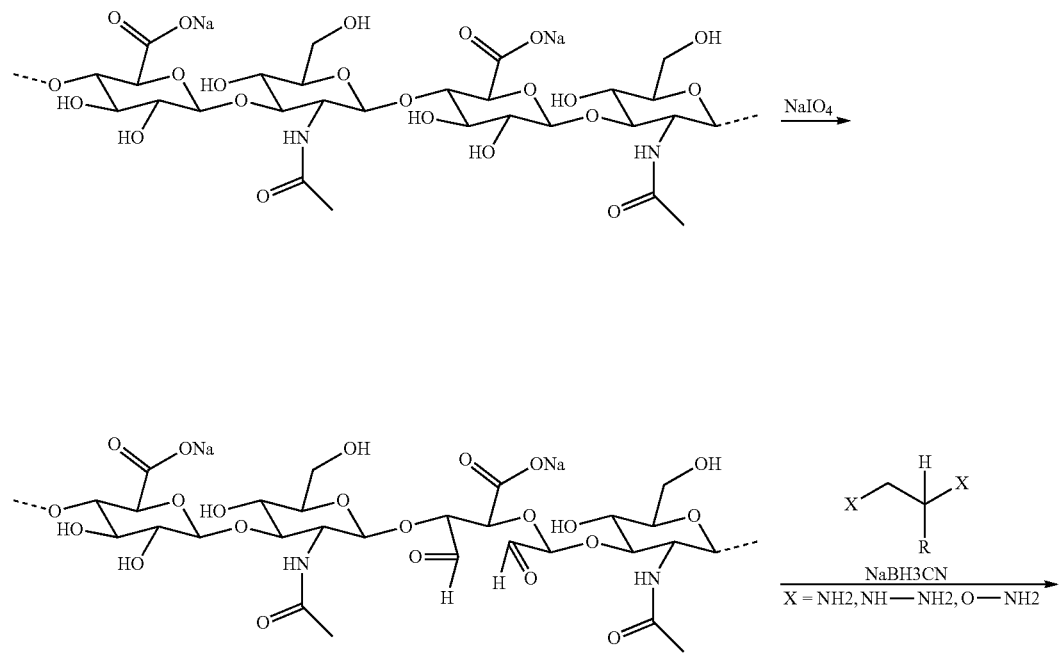

-continued
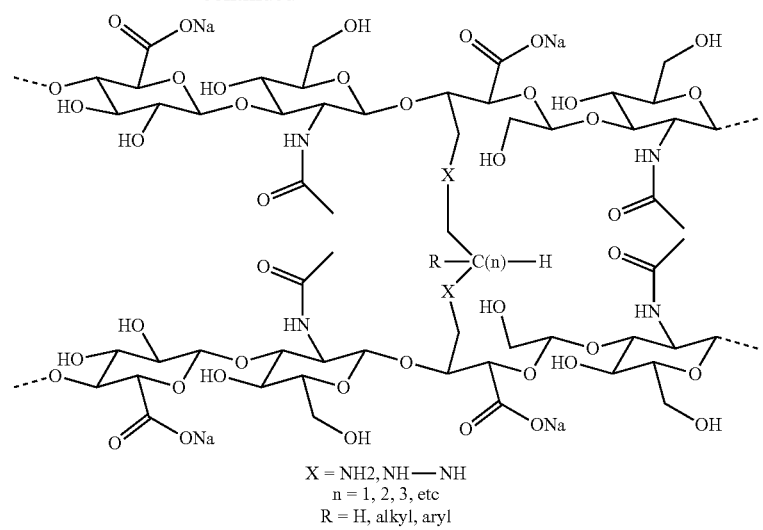
X = NH2, NH—NH
n = 1, 2, 3, etc
R = H, alkyl, aryl
Scheme 10: 2 + 2 Cycloaddition
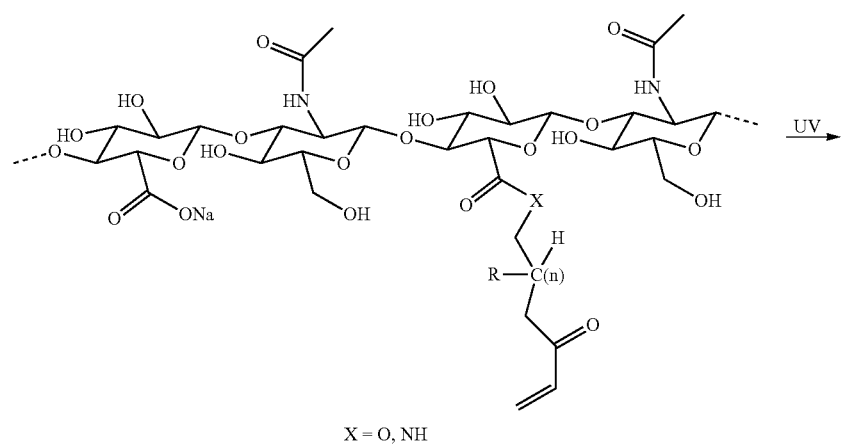
X = O, NH -continued
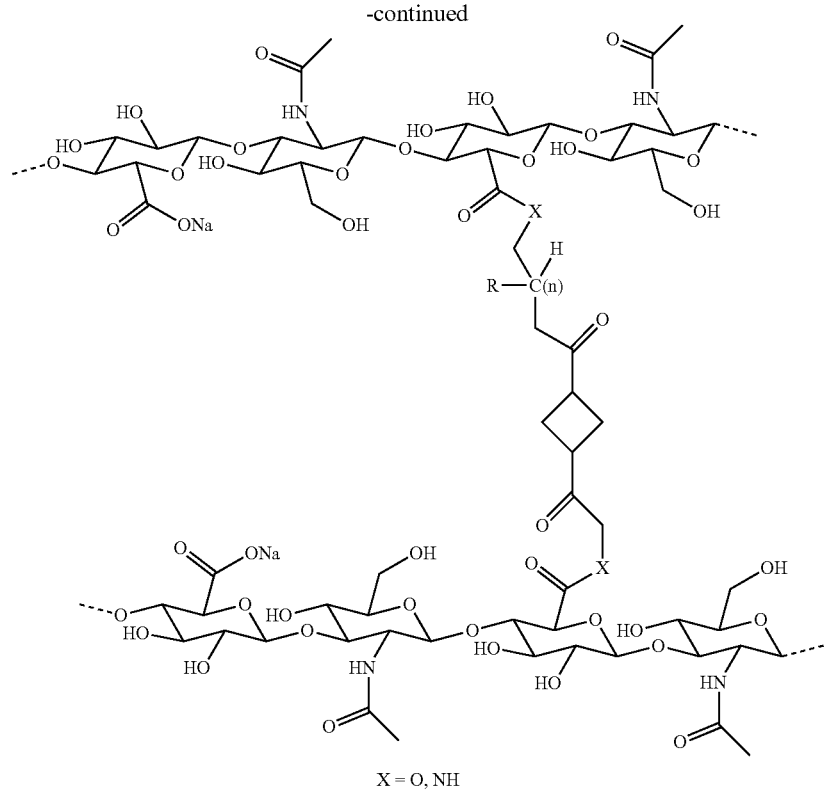
X = O, NH
Scheme 11: 2 + 2 Cycloaddition
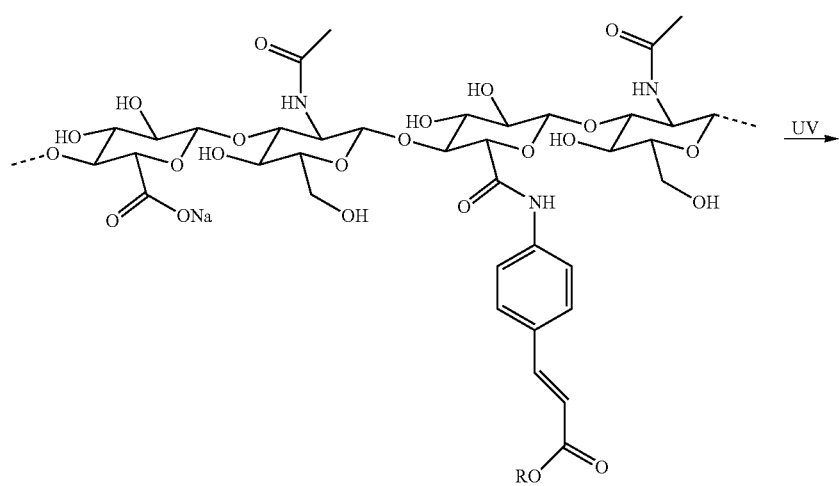

-continued

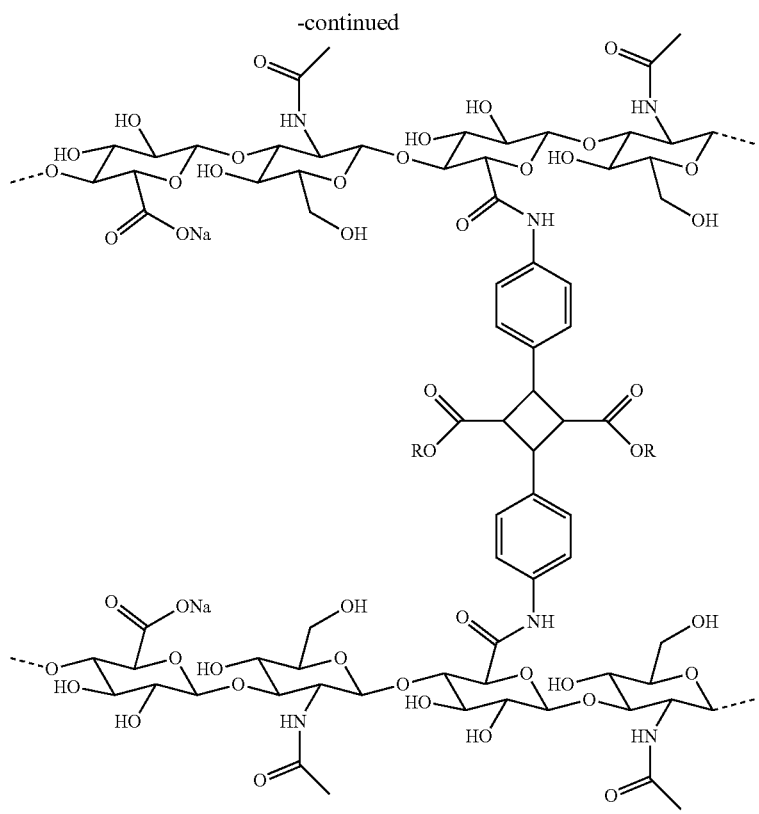

The linkers L are prepared by methods as described in the examples and as disclosed in WO2009/095479, WO2011/012718 and WO2012/035139.

Peptide-Linker Conjugates Synthesis

A preferred way of manufacturing peptides that contain unnatural amino acids and side-chain modifications of amino-groups like within lysine is solid phase synthesis on a suitable resin (SPPS).

Examples are given in: Stewart and Young, Solid Phase Peptide Synthesis, Pierce Chemical Co., Rockford, Ill., 1984; Atherton and Sheppard, Solid Phase Peptide Synthesis, a practical approach, Oxford, IRL Press, New York, 1989; Pennington and Dunn, Methods in Molecular Biology, Volume 35, Peptide Synthesis Protocols, Humana Press, Totowa, N.J., 1994; Jones, The Chemical Synthesis of Peptides, Clarendon Press, Oxford, 1991.

Solid-phase synthesis of a peptide is started with a N-terminally protected amino acid derivative to a solid support-bearing linker. A solid support can be any polymer which is compatible to the solvents used in SPPS and allows coupling of an amino acid derivative with its carboxy group onto the resin (e.g. a trityl resin, a chlorotrityl resin, a Wang-resin when a peptide acid is wanted or a Rink-resin, a Sieber-resin when a peptide amide has to be obtained by using the Fmoc-strategy). Stability of the polymer support must be given under the conditions used for deprotection of the α-amino group during peptide synthesis.

After the first N-terminally protected amino acid was coupled onto the linker-resin construct the N-terminal protecting group is cleaved with bases such as with piperidine/dimethylformamide mixtures (Fmoc-strategy). The liberated amino group is reacted with a Fmoc-protected amino acid derivative using coupling reagents such as e.g. BOP (Benzotriazole-1-yl-oxy-tris(dimethylamino)-phosphonium hexafluorophosphate), HBTU (2-(1H-Benzotriazole-1-yl)-1,1,3,3-tetramethylaminium hexafluorophosphate), HATU (O-(7-Azabenzotriazol-1-yl)-N,N,N',N'-tetramethyluronium hexafluorophosphate) together with a tertiary base like DIPEA (Diisopropylethyl amine) or NMM (N-Methylmorpholine) or alternatively with DIC (N,N'-diisopropylcarbodiimide)/HOBt Hydrate (1-hydroxybenzotriazol). This process is repeated until the desired amino acid sequence is obtained.

Reactive side-chain functions of the amino acid derivatives are usually blocked with suitable protecting groups that are stable under the conditions used for solid phase peptide synthesis. They are removed concomitantly with the cleavage of the desired product from the resin under the same conditions after the peptide has been assembled on the solid phase. Protecting groups and the procedures for their introduction can be found in Greene and Wuts, Protective Groups in Organic Synthesis, $3^{rd}$ ed., Wiley & Sons, New York, 1999 or in Kocienski, Protecting Groups, Georg Thieme Verlag, Stuttgart, N.Y., 1994.

There is also a possibility to remove side-chain protecting groups selectively in SPPS in order to modify them. The conditions for the removal of such a protecting group must be as such that all other protecting groups remain intact. A lysine may be protected with the ivDde- or the Dde-group (see Chhabra et al., Tetrahedron Lett. 39, 1603, 1998) which is labile to a hydrazine-solution in DMF. Once the N-terminal protecting group as well as all the side-chain protecting groups are with acid labile protecting groups, the ivDde- or the Dde-protecting group can be cleaved with hydrazine in DMF. The liberated amino group from the lysine side-chain can be modified thereafter e.g. with other Fmoc-amino acids or fatty acids.

Modification of the Lys(14) side-chain: The peptides Y have 4 lysine amino acids in their sequence, wherein the lysine in position 14 is modified in the side chain (see formula I and II). Therefore for the peptide synthesis two different side chain protected lysines are used: As building block for the position 14, a Mmt-side chain (Monomethoxytrityl) protected lysine is used and Boc-sidechain protected lysines for the others.

The cleavage of these two different protecting groups can be selectively chosen to each other.

The peptide can be finally be cleaved from the resin concomitantly with all the side chain protecting groups with the use of trifluoroacetic acid containing cocktails e.g. the King's cocktail (King et al., Int. J. Peptide Protein Res. 36, 255-266, 1990). Such cocktails might e.g. contain trifluoroacetic acid (TFA), water, ethandithiol (EDT), thioanisol, phenol, triethylsilane (TES) or triisoproplysilane (TIPS) in variable amounts.

After a certain reaction time the resin is filtered off and the crude peptide precipitated in ether e.g. diethyl ether, methyltert.butyl ether or diisopropyl ether. The precipitate can be filtered off or separated from the solution by centrifugation.

A further object of the invention was therefore providing a process for the preparation of the linker-conjugate $L^{2*-}$-L-Y comprising the steps
 a) Assembling of the peptide sequence of Y on a resin including the D-Ser in position 2;
 b) Coupling of His as Fmoc-His(Trt)-OH at position 1;
 c) Deprotection of Fmoc;
 d) Coupling of the linker reagent $L^{2*}$-L- of formula Iaa

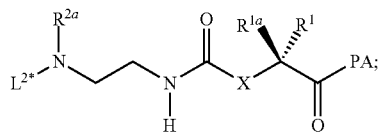

Iaa wherein $L^{2*}$ is a $C_{1-20}$ alkyl chain, which is optionally interrupted by one or more groups independently selected from —O— and $C(O)N(R^{3aa})$ and is optionally substituted with one or more groups independently selected from OH and $C(O)N(R^{3aa}R^{3aaa})$, wherein $R^{3aa}$ and $R^{3aaa}$ are independently selected from the group consisting of H and $C_{1-4}$ alkyl; and comprises a chemical functional group intended for conjugation to $L^1$;
 PA is OH or an activating group like p-nitrophenylester;
 e) Deprotection of Mmt at position 14;
 f) Coupling of Palm-Glu(γOSu)-OtBu or Stea-Glu (γOSu)-OtBu at position 14;
 g) Cleavage from the resin and deprotection from all protected groups.

In another embodiment of the process
$L^{2*}$ is a $C_{1-6}$ alkyl chain, which is optionally interrupted by one group selected from —O— and $C(O)N(R^{3aa})$ and, wherein $R^{3aa}$ is independently selected from the group consisting of H and $C_{1-4}$ alkyl; and comprises a chemical functional group selected from thiol or maleimide.

In another embodiment of the process
$L^{2*}$ is —CH$_2$—CH$_2$—CH$_2$—CH$_2$—CH$_2$—C(O)NH— or —CH$_2$—CH$_2$—CH$_2$—CH$_2$—CH$_2$—CH$_2$— and and comprises a thiol group as chemical functional group.

An object of the invention is therefore providing a process for the preparation of the linker-conjugate $L^{2*-}$-L-Y comprising the steps a) Assembling of the peptide sequence of Y on a resin including the D-Ser in position 2;
 b) Coupling of His as Fmoc-His(Trt)-OH at position 1;
 c) Deprotection of Fmoc;
 d) Coupling of the linker reagent $L^{2*}$-L- of formula Iab

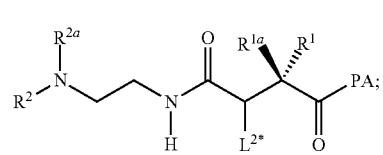

Iab wherein the definitions are as described above;
 e) Deprotection of Mmt at position 14;
 f) Coupling of Palm-Glu(γOSu)-OtBu or Stea-Glu (γOSu)-OtBu at position 14;
 g) Cleavage from the resin and deprotection from all protected groups.

For linker conjugates $L^{2*-}$-L-Y wherein X in L is NH an alternative process is the coupling of the linker reagent $L^{2*}$-L- in two steps first coupling the amino acid part and secondly coupling the residing part of the linker.

An object of the invention is therefore providing a process for the preparation of the linker-conjugate $L^{2*-}$-L-Y wherein X in L is NH, comprising the steps a) Assembling of the peptide sequence of Y on a resin including the D-Ser in position 2;
 b) Coupling of His as Fmoc-His(Trt)-OH at position 1;
 c) Deprotection of Fmoc;
 d) Coupling of an amino acid of formula Icc

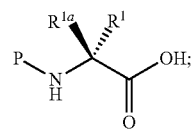

Icc wherein P is a protecting group, preferably Fmoc;
 e) Deprotection of Fmoc;
 f) Coupling of the linker reagent $L^{2*}$-L*- of formula Icd

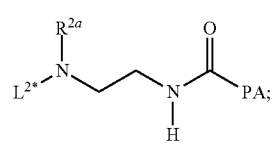

Icd wherein the definitions are as described above; PA is OH or a activation group like p-nitrophenylester;
 g) Deprotection of Mmt at position 14;
 h) Coupling of Palm-Glu(γOSu)-OtBu or Stea-Glu (γOSu)-OtBu at position 14;
 i) Cleavage from the resin and deprotection from all protected groups;
 wherein
 $R^1$, $R^{1a}$, $R^{2a}$ are selected independently from the group consisting of H and $C_{1-4}$ alkyl;
 $L^{2*}$- is defined as described above.

In one embodiment of the process $R^1$ is $CH_3$ and $R^{1a}$ is H in formula Icc.

In another embodiment of the process $R^1$ is H and $R^{1a}$ is $CH_3$ in formula Icc.

In another embodiment of the process $R^1$ is $CH_3$ and $R^{1a}$ is $CH_3$ in formula Icc.

Another object of the invention is therefore providing a process for the preparation of a linker-conjugate of formula $L^{2*-}L-Y$ comprising the steps:
 a) Assembling of the peptide sequence of Y on a resin including the D-Ser in position 2;
 b) Coupling of His as Fmoc-His(Trt)-OH at position 1;
 c) Deprotection of Fmoc;
 d) Coupling of Fmoc-Aib-OH;
 e) Deprotection of Fmoc;
 f) Coupling of the linker reagent $L^{2*}-L^{*}-$ of formula Iac

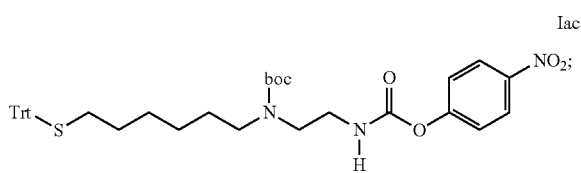

Iac g) Deprotection of Mmt at position 14;
 h) Coupling of Palm-Glu(γOSu)-OtBu or Stea-Glu(γOSu)-OtBu at position 14;
 i) Cleavage from the resin and deprotection from all protected groups.

Another object of the invention is providing a process for the preparation of a linker-conjugate of formula $L^{2*-}L-Y$ comprising the steps:
 a) Assembling of the peptide sequence of Y on a resin including the D-Ser in position 2;
 b) Coupling of His as Fmoc-His(Trt)-OH at position 1;
 c) Deprotection of Fmoc;
 d) Coupling of Fmoc-Aib-OH;
 e) Deprotection of Fmoc;
 f) Coupling of the linker reagent $L^{2*}-L^{*}-$ of formula Iac

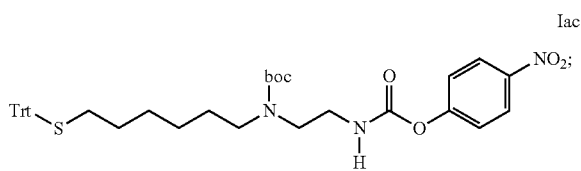

Iac g) Deprotection of Mmt at position 14;
 h) Coupling of Fmoc-Glu(tBu);
 i) Deprotection of Fmoc;
 j) Coupling of Palm-NHS or Stea-NHS;
 k) Cleavage from the resin and deprotection from all protected groups.

Another object of the invention is providing a process for the preparation of a linker-conjugate of formula $L^{2*-}L-Y$ comprising the steps:
 a) Assembling of the peptide sequence of Y on a resin including the D-Ser in position 2;
 b) Coupling of His as Fmoc-His(Trt)-OH at position 1;
 c) Deprotection of Fmoc;
 d) Coupling of Fmoc-Aib-OH;
 e) Deprotection of Fmoc;
 f) Coupling of Coupling of Palm-Glu(γOSu)-OtBu or Stea-Glu(γOSu)-OtBu at position 14;
 g) Deprotection of Fmoc;

h) Coupling of the linker reagent $L^{2*}-L^{*}-$ of formula Iad

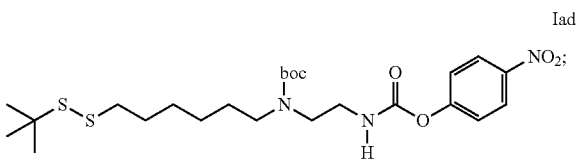

Iad i) Cleavage from the resin and deprotection from all protected groups;
 j) Reductive cleavage of S-tBu protecting group.

An additional subsequent process step for all above described processes is the purification by chromatography and the isolation of the peptide linker conjugate of formula $-L^{2*-}L-Y$ by methods known in the art.

The conjugate of the present invention can be prepared by synthesizing the building blocks activated hyaluronic acid hydrogel with $-L^{1*}$ and activated peptide linker conjugate $L^{2*}-L-Y$.

Activated groups $L^{1*}$ and $L^{2*}$ are used to conjugate peptide to the polymers. Scheme 12 shows different types of linking chemistries which can be used to conjugate the peptide with self-immolative linkers to the polymer. Thus, besides thiol-maleimide chemistry, other biorthogonal chemistries can be used. In scheme 12 the dashed lines indicates the positions where $L^1$ and $L^2$ are attached.

After loading the GLP-1/Glucagon agonist-linker conjugate to the functionalized hyaluronic acid hydrogel, all remaining functional groups are optionally capped with a suitable blocking reagent to prevent undesired side-reactions.

In the case of a functionalized maleimido group-containing HA-hydrogel, a thiol containing compound such as mercaptoethanol is a suitable blocking agent.

Scheme 12

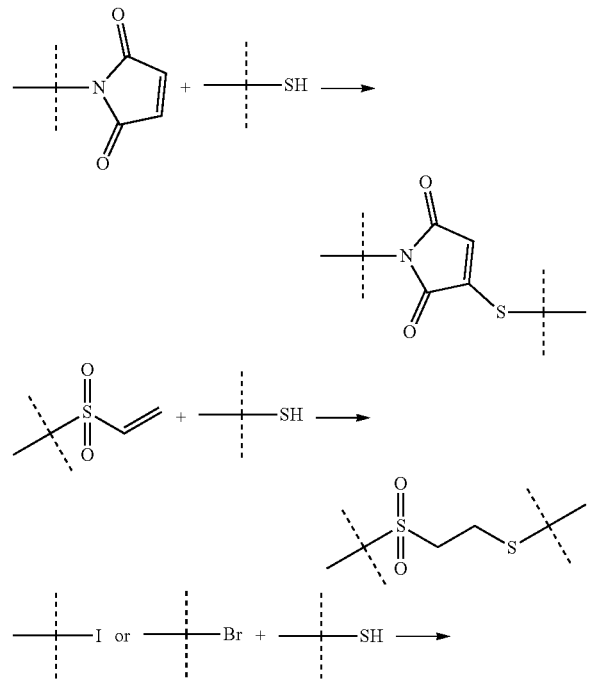

-continued

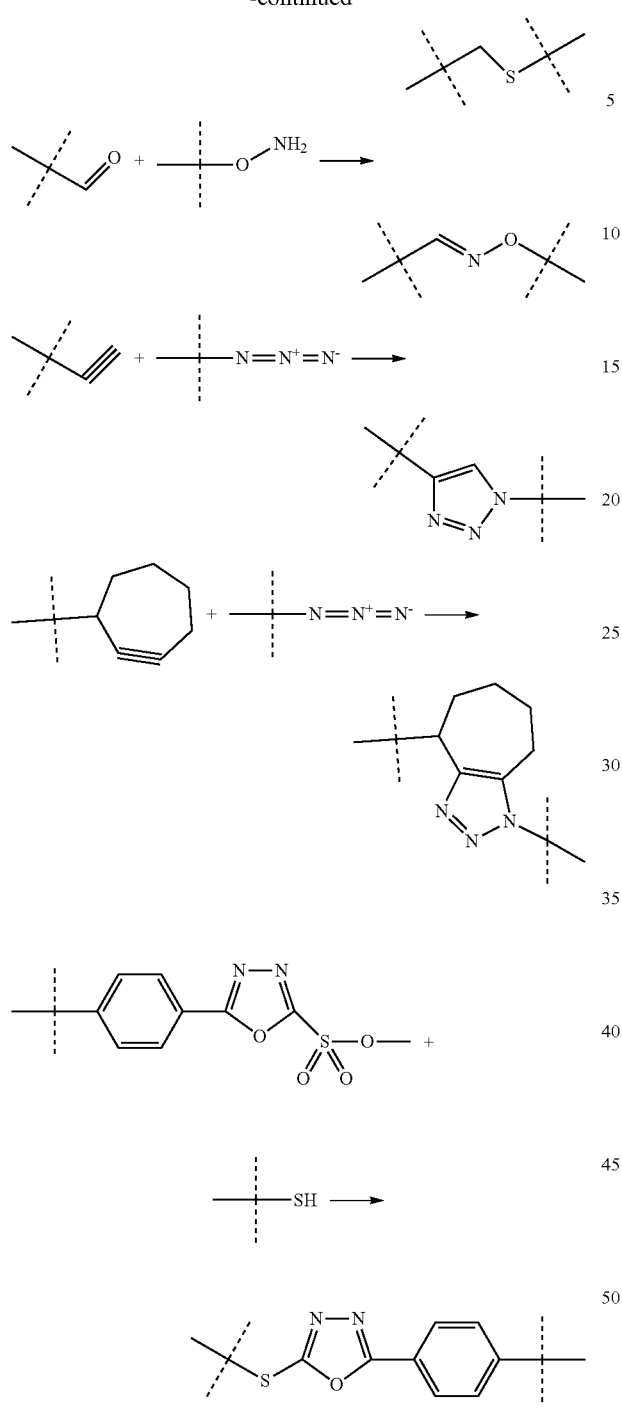

Another aspect of the present invention are functionalized intermediates comprising $L^{2*}$-L-Y wherein $L^{2*}$, L and Y are defined as described above.

One embodiment of $L^{2*}$-L-Y comprises a thiol functionalization, resulting in the formula IV

wherein $L^2$, L and Y have the meanings as described above.

One embodiment of $L^{2*}$-L-Y is of formula (IVa)

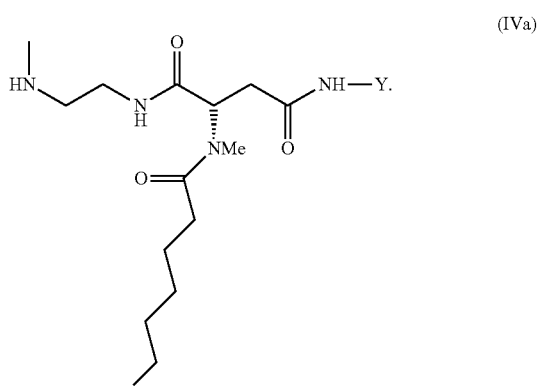

One embodiment of $L^{2*}$-L-Y is of formula (IVb)

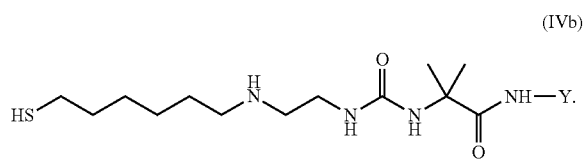

One embodiment of $L^{2*}$-L-Y is of formula (IVc)

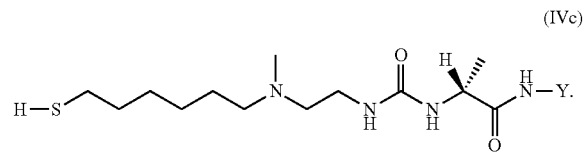

In another embodiment the hydrogel for the conjugate of the present invention can be obtained from the preparation methods in form of microparticles. In a preferred embodiment of the invention, the reactive hydrogel is shaped by a mesh or a stent. Most preferably, the hydrogel is formed into microparticulate beads which can be administered as subcutaneous or intramuscular injection by means of a standard syringe. Such soft beads may have a diameter of between 1 and 500 micrometer.

Pharmaceutical Composition

Another aspect of the present invention is a pharmaceutical composition comprising a conjugate of the present invention or a pharmaceutically acceptable salt thereof together with a pharmaceutically acceptable excipient. The pharmaceutical composition is further described in the following paragraphs.

The composition of conjugate of the invention may be provided as a suspension composition or as a dry composition. In one embodiment the pharmaceutical composition of the conjugate of the invention is a dry composition. Suitable methods of drying are, for example, spray-drying and lyophilization (freeze-drying). Preferably, the pharmaceutical composition of the conjugate of the invention is dried by lyophilization.

In another embodiment the pharmaceutical composition of the conjugate of the invention is a ready to use suspension.

In another embodiment the pharmaceutical composition of the conjugate of the invention is a ready to use suspension wherein the conjugate is swollen in water/buffer to a concentration of 0.5 to 8% (w/v).

In another embodiment the pharmaceutical composition of the conjugate of the invention is a ready to use suspension wherein the conjugate is swollen in water/buffer to a concentration of 1 to 4% (w/v).

In another embodiment the pharmaceutical composition of the conjugate of the invention is a ready to use suspension wherein the conjugate is swollen in water/buffer to a concentration of 1.5 to 3% (w/v).

Preferably, the conjugate of the invention is sufficiently dosed in the composition to provide therapeutically effective amount of GLP-1/Glucagon agonist for at least three days in one application. More preferably, one application of the conjugate of the invention is sufficient for one week.

The pharmaceutical composition of the conjugate of the invention according to the present invention contains one or more excipients.

Excipients used in parenteral compositions may be categorized as buffering agents, isotonicity modifiers, preservatives, stabilizers, anti-adsorption agents, oxidation protection agents, viscosifiers/viscosity enhancing agents, or other auxiliary agents. In some cases, these ingredients may have dual or triple functions. The compositions of the conjugate of the invention according to the present invention contain one or more than one excipient, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability (ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum (iii) Preservatives and/or antimicrobials: multidose parenteral preparations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride (iv) Stabilizers: Stabilisation is achieved by strengthening of the protein-stabilising forces, by destabilisation of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used (v) Anti-adsorption agents: Mainly ionic or non-ionic surfactants or other proteins or soluble polymers are used to coat or adsorb competitively to the inner surface of the composition's or composition's container. E.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value (vi) Lyo- and/or cryoprotectants: During freeze- or spray drying, excipients may counteract the destabilising effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, methionine, glutathione, monothioglycerol, morin, polyethylenimine (PEI), propyl gallate, vitamin E, chelating agents such as citric acid, EDTA, hexaphosphate, thioglycolic acid (viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).
(ix) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.
(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture In one embodiment the composition of the conjugate of the invention contains one or more than one viscosifier and/or viscosity modifying agent.

In another embodiment the composition of the conjugate of the invention contains hyaluronic acid as viscosifier and/or viscosity modifying agent.

In another embodiment the composition the conjugate of the invention comprises hyaluronic acid as viscosifier and/or viscosity modifying agent in a concentration of 5 to 30 wt %.

In another embodiment the composition of the conjugate of the invention comprises hyaluronic acid as viscosifier and/or viscosity modifying agent of a molecular weight of 200 kDa to 6 million kDa.

In another embodiment the composition of the conjugate of the invention comprises hyaluronic acid as viscosifier and/or viscosity modifying agent of a molecular weight of 500 kDa to 3 million kDa.

In another embodiment the composition comprises at least one conjugate of the invention for use in a method of treatment of Type 1 diabetes, Type 2 diabetes, obesity or hyperglycemia characterized in that the composition is subcutaneously administered via an injection device comprising a tube having a needle gauge of 26 or greater and wherein said composition is administered once weekly.

The term "excipient" preferably refers to a diluent, adjuvant, or vehicle with which the therapeutic is administered. Such pharmaceutical excipient can be sterile liquids. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. Such compositions will contain a therapeutically effective amount of the therapeutic, preferably in purified form, together with a suitable amount of excipient so as to provide the form for proper administration to the patient. The formulation should suit the mode of administration.

In a general embodiment a pharmaceutical composition of the present invention whether in dry form or as a suspension or in another form may be provided as single or multiple dose composition.

In one embodiment of the present invention, the dry composition of the conjugate of the invention is provided as a single dose, meaning that the container in which it is supplied contains one pharmaceutical dose.

Thus, in another aspect of the present invention the composition is provided as a single dose composition.

In another aspect of the present invention the composition is comprised in a container. In one embodiment the container is a dual-chamber syringe. Especially the dry composition according to the present invention is provided in a first chamber of the dual-chamber syringe and reconstitution solution is provided in a second chamber of the dual-chamber syringe.

Prior to applying the dry composition the conjugate of the invention to a patient in need thereof, the dry composition is reconstituted. Reconstitution can take place in the container in which the dry composition of the conjugate of the invention is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials. If the composition is provided as single dose, the reconstitution solution may contain one or more preservative and/or antimicrobial. Preferably, the reconstitution solution is sterile water.

An additional aspect of the present invention relates to the method of administration of a reconstituted composition. The composition can be administered by methods of injection or infusion, including intradermal, subcutaneous, intramuscular, intravenous, intraosseous, and intraperitoneal.

A further aspect is a method of preparing a reconstituted composition comprising a therapeutically effective amount of an conjugate of the invention, and optionally one or more pharmaceutically acceptable excipients, wherein the GLP-1/Glucagon agonist is transiently linked to a hydrogel, the method comprising the step of
  contacting the composition of the present invention with a reconstitution solution.

Another aspect is a reconstituted composition comprising a therapeutically effective amount of a conjugate of the invention, and optionally one or more pharmaceutically acceptable excipients, wherein the GLP-1/Glucagon agonist is transiently linked to a hydrogel obtainable by the method above.

Another aspect of the present invention is the method of manufacturing a dry composition of the conjugate of the invention. In one embodiment, such suspension composition is made by
  (i) admixing the conjugate of the invention with one or more excipients,
  (ii) transferring amounts equivalent to single or multiple doses into a suitable container,
  (iii) drying the composition in said container, and
  (iv) sealing the container.

Suitable containers are vials, syringes, dual-chamber syringes, ampoules, and cartridges.

Another aspect is a kit of parts. When the administration device is simply a hypodermic syringe then the kit may comprise the syringe, a needle and a container comprising the dry composition for use with the syringe and a second container comprising the reconstitution solution. In more preferred embodiments, the injection device is other than a simple hypodermic syringe and so the separate container with reconstituted conjugate of the invention is adapted to engage with the injection device such that in use the liquid composition in the container is in fluid connection with the outlet of the injection device. Examples of administration devices include but are not limited to hypodermic syringes and pen injector devices. Particularly preferred injection devices are the pen injectors in which case the container is a cartridge, preferably a disposable cartridge.

A preferred kit of parts comprises a needle and a container containing the composition according to the present invention and optionally further containing a reconstitution solution, the container being adapted for use with the needle. Preferably, the container is a dual-chamber syringe.

In another aspect, the invention provides a cartridge containing a composition of the conjugate of the invention as hereinbefore described for use with a pen injector device. The cartridge may contain a single dose or multiplicity of doses of GLP-1/Glucagon agonist.

In one embodiment of the present invention the suspension composition of the conjugate of the invention does not only comprise the conjugate of the invention and one or more than one excipients, but also other biologically active agents, either in their free form or as conjugates. Preferably, such additional one or more biologically active agent is a conjugate, more preferably a hydrogel conjugate. Such biologically active agents include, but are not limited to, compounds described under combination therapy.

Injectability

Preferably, the formulation can be administered by injection through a needle smaller than 0.26 mm inner diameter (26 Gauge), even more preferably through a needle smaller than 0.18 mm inner diameter (28 Gauge), and most preferably through a needle small than 0.16 mm inner diameter (30 Gauge).

It is understood that the terms "can be administered by injection", "injectable" or "injectability" refer to a combination of factors such as a certain force applied to a plunger of a syringe containing the biodegradable HA hydrogel according to the invention swollen in a liquid at a certain concentration (w/v) and at a certain temperature, a needle of a given inner diameter connected to the outlet of such syringe, and the time required to extrude a certain volume of the biodegradable hydrogel according to the invention from the syringe through the needle.

In order to provide for injectability, a volume of 1 mL of the conjugates according to the invention swollen in water/buffer and contained in a syringe (holding a plunger of a diameter of 4.7 mm) can be extruded at room temperature within 10 seconds by applying a force of equal/less than 20 Newton through a needle of 26 gauge.

A preferred injectability is a volume of 1 mL of the conjugates according to the invention swollen in water/buffer and contained in a syringe (holding a plunger of a diameter of 4.7 mm) which can be extruded at room temperature within 10 seconds by applying a force of equal/less than 20 Newton through a needle of 30 gauge.

In order to provide for injectability, a volume of 1 mL of the conjugates according to the invention swollen in water/buffer to a concentration of at least 1.5% (w/v) and contained in a syringe holding a plunger of a diameter of 4.7 mm can be extruded at room temperature within 10 seconds by applying a force of less than 30 Newton through a needle of 30 gauge.

More preferably injectability is achieved for a conjugate according to the invention swollen in water/buffer to a concentration of at least 2% (w/v) by applying a force of less than 30 Newtons through a needle of 30 gauge.

Most preferably injectability is achieved for a conjugate according to the invention swollen in water/buffer to a concentration of at least 2% (w/v) by applying a force of less than 20 Newtons through a needle of 30 gauge.

An important characteristic of the conjugate is the forming of a stable depot which stays its application site. The degradation of the polymer should start after release of the drug.

Another embodiment is a injection device comprising a tube having a gauge of 28 or greater and further comprising a conjugate of the invention for use in a method of treatment of Type 1 diabetes, Type 2 diabetes, obesity, or hyperglycemia.

Administration Unit, Package, Pen Device and Administration

The compound(s) of the present invention can be prepared for use in suitable pharmaceutical compositions. The suitable pharmaceutical compositions may be in the form of one or more administration units.

The compositions may be prepared by any suitable pharmaceutical method which includes a step in which the compound(s) of the present invention and the carrier (which may consist of one or more additional ingredients) are brought into contact.

The administration units may be for example capsules, tablets, dragées, granules sachets, drops, solutions, suspensions, lyophylisates and powders, each of which contains a defined amount of the compound(s) of the present invention.

Each of the above-mentioned administration units of the compound(s) of the invention or pharmaceutical composition of the invention (administration units) may be provided in a package for easy transport and storage. The administration units are packaged in standard single or multi-dosage packaging, their form, material and shape depending on the type of units prepared.

For example, tablets and other forms of solid administration units can be packaged in single units, and the single packaged units can be packaged in multi-pack containers.

Liquid formulations can be packaged in single units, such as e.g. vials, cartridges, syringes/prefilled syringes, infusion bags, collapsible plastic bags, infusion bottles, blow-filled seal bottles or infusion tubings or in single or multiple dose injectable form, for example in the form of a pen device, pump or syringe and the single packaged units can be packaged in multi-pack containers. A single package may comprise only one or a plurality of administration units. The package may for example be made of paper, cardboard, paperboard, plastic, metal, combinations or laminates of one or more of paper, plastics and metal, or glass. Exemplary embodiments are blister packages containing e.g. tablets or capsules, which in turn may be provided inside a cardboard box, aluminum barrier laminate sachets containing e.g. a powder, glass or plastic bottles containing e.g. tablets or a solution, or vials, cartridges, syringes, infusion bags, infusion bottles, infusion tubings or ampoules containing a solution or suspension.

In certain embodiments administration units may be provided together with a device for application, for example together with a syringe, an injection pen or an autoinjector. Such devices may be provided separate from a pharmaceutical composition or prefilled with the pharmaceutical composition.

A "pen-type injection device", often briefly referred to as "injection pen", is typically an injection device having an elongated shape that resembles to a fountain pen for writing.

Although such pens usually have a tubular cross-section, they could easily have a different cross-section such as triangular, rectangular or square or any variation around these geometries. Generally, pen-type injection devices comprise three primary elements: a cartridge section that includes a cartridge often contained within a housing or holder; a needle assembly connected to one end of the cartridge section; and a dosing section connected to the other end of the cartridge section. The cartridge, often also referred to as "ampoule", typically includes a reservoir that is filled with a medication, a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

Combination Therapy

The conjugates of the present invention, dual agonists for the GLP-1 and glucagon receptors, can be widely combined with other pharmacologically active compounds, such as all drugs mentioned in the Rote Liste 2016, e.g. with all weight-reducing agents or appetite suppressants mentioned in the Rote Liste 2015, chapter 1, all lipid-lowering agents mentioned in the Rote Liste 2016, chapter 58, all antihypertensives and nephroprotectives, mentioned in the Rote Liste 2016, or all diuretics mentioned in the Rote Liste 2016, chapter 36.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Other active substances which are suitable for such combinations include in particular those which for example potentiate the therapeutic effect of one or more active substances with respect to one of the indications mentioned and/or which allow the dosage of one or more active substances to be reduced.

Therapeutic agents which are suitable for combinations include, for example, antidiabetic agents such as:

Insulin and Insulin derivatives, for example: Glargine/Lantus, 270-330 U/mL of insulin glargine (EP 2387989 A), 300 U/mL of insulin glargine (EP 2387989 A), Glulisin/Apidra®, Detemir/Levemir®, Lispro/Humalog®/Liprolog®, Degludec/DegludecPlus, Aspart, basal insulin and analogues (e.g. LY-2605541, LY2963016, NN1436), PEGylated insulin Lispro, Humulin®, Linjeta, SuliXen®, NN1045, Insulin plus Symlin, PE0139, fast-acting and short-acting insulins (e.g. Linjeta, PH20, NN1218, HinsBet), (APC-002)hydrogel, oral, inhalable, transdermal and sublingual insulins (e.g. Exubera®, Nasulin®, Afrezza, Tregopil, TPM 02, Capsulin, Oral-lyn®, Cobalamin® oral insulin, ORMD-0801, NN1953, NN1954, NN1956, VIAtab, Oshadi oral insulin). Additionally included are also those insulin derivatives which are bonded to albumin or another protein by a bifunctional linker.

GLP-1, GLP-1 analogues and GLP-1 receptor agonists, for example: Lixisenatide/AVE0010/ZP10/Lyxumia, Exenatide/Exendin-4/Byetta/Bydureon/ITCA 650/AC-2993, Liraglutide/Victoza, Semaglutide, Taspoglutide, Syncria/Albiglutide, Dulaglutide, rExendin-4, CJC-1134-PC, PB-1023, TTP-054, Langlenatide/HM-112600, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

DPP-4 inhibitors, for example: Alogliptin/Nesina, Trajenta/Linagliptin/BI-1356/Ondero/Trajenta/Tradjenta/Trayenta/Tradzenta, Saxagliptin/Onglyza, Sitagliptin/Januvia/Xelevia/Tesave/Janumet/Velmetia, Galvus/Vildagliptin, Anagliptin, Gemigliptin, Teneligliptin, Melogliptin, Trelagliptin, DA-1229, Omarigliptin/MK-3102, KM-223, Evogliptin, ARI-2243, PBL-1427, Pinoxacin.

SGLT2 inhibitors, for example: Invokana/Canaglifozin, Forxiga/Dapagliflozin, Remoglifozin, Sergliflozin, Empagliflozin, Ipragliflozin, Tofogliflozin, Luseogliflozin, LX-4211, Ertuglifozin/PF-04971729, RO-4998452, EGT-0001442, KGA-3235/DSP-3235, LIK066, SBM-TFC-039, Biguanides (e.g. Metformin, Buformin, Phenformin), Thiazolidinediones (e.g. Pioglitazone, Rivoglitazone, Rosiglitazone, Troglitazone), dual PPAR agonists (e.g. Aleglitazar, Muraglitazar, Tesaglitazar), Sulfonylureas (e.g. Tolbutamide, Glibenclamide, Glimepiride/Amaryl, Glipizide), Meglitinides (e.g. Nateglinide, Repaglinide, Mitiglinide), Alpha-glucosidase inhibitors (e.g. Acarbose, Miglitol, Voglibose), Amylin and Amylin analogues (e.g. Pramlintide, Symlin).

GPR119 agonists (e.g. GSK-263A, PSN-821, MBX-2982, APD-597, ZYG-19, DS-8500), GPR40 agonists (e.g. Fasiglifam/TAK-875, TUG-424, P-1736, JTT-851, GW9508).

Other suitable combination partners are: Cycloset, inhibitors of 11-beta-HSD (e.g. LY2523199, BMS770767, RG-4929, BMS816336, AZD-8329, HSD-016, BI-135585), activators of glucokinase (e.g. TTP-399, AMG-151, TAK-329, GKM-001), inhibitors of DGAT (e.g. LCQ-908), inhibitors of protein tyrosine phosphatase 1 (e.g. Trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha2-antagonists, CCR-2 antagonists, SGLT-1 inhibitors (e.g. LX-2761).

One or more lipid lowering agents are also suitable as combination partners, such as for example: HMG-CoA-reductase inhibitors (e.g. Simvastatin, Atorvastatin), fibrates (e.g. Bezafibrate, Fenofibrate), nicotinic acid and the derivatives thereof (e.g. Niacin), PPAR-(alpha, gamma or alpha/gamma) agonists or modulators (e.g. Aleglitazar), PPAR-delta agonists, ACAT inhibitors (e.g. Avasimibe), cholesterol absorption inhibitors (e.g. Ezetimibe), Bile acid-binding substances (e.g. cholestyramine, colesevelam), ileal bile acid transport inhibitors, MTP inhibitors, or modulators of PCSK9.

HDL-raising compounds such as: CETP inhibitors (e.g. Torcetrapib, Anacetrapid, Dalcetrapid, Evacetrapid, JTT-302, DRL-17822, TA-8995) or ABC1 regulators.

Other suitable combination partners are one or more active substances for the treatment of obesity, such as for example: Sibutramine, Tesofensine, Orlistat, antagonists of the cannabinoid-1 receptor, MCH-1 receptor antagonists, MC4 receptor agonists, NPY5 or NPY2 antagonists (e.g. Velneperit), beta-3-agonists, leptin or leptin mimetics, agonists of the 5HT2c receptor (e.g. Lorcaserin), or the combinations of bupropione/naltrexone, bupropione/zonisamide, bupropione/phentermine or pramlintide/metreleptin.

Other suitable combination partners are:

Further gastrointestinal peptides such as Peptide YY 3-36 (PYY3-36) or analogues thereof, pancreatic polypeptide (PP) or analogues thereof.

Glucagon receptor agonists or antagonists, GIP receptor agonists or antagonists, ghrelin antagonists or inverse agonists, Xenin and analogues thereof.

Moreover, combinations with drugs for influencing high blood pressure, chronic heart failure or atherosclerosis, such as e.g.: Angiotensin II receptor antagonists (e.g. telmisartan, candesartan, valsartan, losartan, eprosartan, irbesartan, olmesartan, tasosartan, azilsartan), ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

Use

In another aspect, this invention relates to the use of a conjugate according to the invention or a physiologically acceptable salt thereof combined with at least one of the active substances described above as a combination partner, for preparing a medicament which is suitable for the treatment or prevention of diseases or conditions which can be affected by binding to the receptors for GLP-1 and glucagon and by modulating their activity.

Said compositions are for use in a method of treating or preventing diseases or disorders known for GLP-1/Glucagon agonist and GLP-1/Glucagon agonist agonists, for example, for treatment and prevention of hyperglycemia and for treatment and prevention of diabetes mellitus of any type, e.g. insulin-dependent diabetes mellitus, non-insulin dependent diabetes mellitus, prediabetes or gestational diabetes mellitus, for prevention and treatment of metabolic syndrome and/or obesity and/or eating disorders, insulin resistance syndrome, lowering plasma lipid level, reducing the cardiac risk, reducing the appetite, reducing the body weight, etc.

Said conjugates or compositions are useful in the treatment or prevention of hepatosteatosis, preferably non-alcoholic liver-disease (NAFLD) and non-alcoholic steatohepatitis (NASH).

Another aspect of the invention is a method of treating or preventing diseases or disorders which can be treated by GLP-1/Glucagon agonist, the method comprising administering a conjugate as described above or a pharmaceutical composition thereof.

Another aspect of the invention is a method of treating or preventing diabetes, the method comprising administering a conjugate as described above or a pharmaceutical composition thereof.

Another aspect of the invention is a method of treating or preventing dyslipidemia, the method comprising administering a conjugate as described above or a pharmaceutical composition thereof.

Another aspect of the invention is a method of treating or preventing metabolic syndrome, the method comprising administering a conjugate as described above or a pharmaceutical composition thereof.

Another aspect of the invention is a method of treating or preventing hepatosteatosis, the method comprising administering a conjugate as described above or a pharmaceutical composition thereof.

The use of the conjugates according to the invention, or a physiologically acceptable salt thereof, in combination with one or more active substances may take place simultaneously, separately or sequentially.

The use of the conjugate according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours. 12 hours, but particularly less than or equal to 6 hours.

Consequently, in another aspect, this invention relates to a medicament which comprises a conjugate according to the invention or a physiologically acceptable salt of such a compound and at least one of the active substances described above as combination partners, optionally together with one or more inert carriers and/or diluents.

The conjugate according to the invention, or physiologically acceptable salt or solvate thereof, and the additional active substance to be combined therewith may both be present together in one formulation, for example a suspension, or separately in two identical or different formulations, for example as so-called kit-of-parts.

Yet another aspect of the present invention is a method of treating, controlling, delaying or preventing in a mammalian patient, preferably in a human, in need of the treatment of one or more conditions comprising administering to said patient a therapeutically effective amount of a conjugate of the present invention or a pharmaceutical composition of the present invention or a pharmaceutically acceptable salt thereof.

Methods

Abbreviations employed are as follows:
AA amino acid
AcOH acetic acid
AcOEt ethyl acetate
Aib alpha-amino-isobutyric acid
cAMP cyclic adenosine monophosphate
Bn benzyl
Boc tert-butyloxycarbonyl
BOP (benzotriazol-1-yloxy)tris(dimethylamino)phosphonium hexafluorophosphate
BSA bovine serum albumin
tBu tertiary butyl
dAla D-alanine
DBU 1,3-diazabicyclo[5.4.0]undecene
DCC N,N-dicyclohexylcarbodiimide
DCM dichloromethane
Dde 1-(4,4-dimethyl-2,6-dioxocyclohexylidene)-ethyl
ivDde 1-(4,4-dimethyl-2,6-dioxocyclohexylidene)3-methyl-butyl
DIC N,N'-diisopropylcarbodiimide
DIPEA N,N-diisopropylethylamine
DMAP dimethylamino-pyridine
DMEM Dulbecco's modified Eagle's medium
DMF dimethyl formamide
DMS dimethylsulfide
DMSO dimethylsulfoxide
DTT DL dithiothreitol
DVS Di-vinylsulfone
EDC 1-Ethyl-3-(3-dimethylaminopropyl)carbodiimid
EDT ethanedithiol
EDTA ethylenediaminetetraacetic acid
eq stoichiometric equivalent
EtOH ethanol
FA formic acid
FBS fetal bovine serum
Fmoc fluorenylmethyloxycarbonyl
gGlu gamma-glutamate (γE)
HATU O-(7-azabenzotriazol-1-yl)-N,N,N',N'-tetramethyl-uronium hexafluorophosphate
HBSS Hanks' Balanced Salt Solution HBTU 2-(1H-benzotriazol-1-yl)-1,1,3,3-tetramethyl-uronium hexafluorophosphate
HEPES 2-[4-(2-hydroxyethyl)piperazin-1-yl]ethanesulfonic acid
HOBt 1-hydroxybenzotriazole
HOSu N-hydroxysuccinimide
HPLC High Performance Liquid Chromatography
HTRF Homogenous Time Resolved Fluorescence
IBMX 3-isobutyl-1-methylxanthine
LC/MS Liquid Chromatography/Mass Spectrometry
Mal 3-maleimido propyl
Mal-PEG6-NHS N-(3-maleimidopropyl)-21-amino-4,7,10,13,16,19-hexaoxa-heneicosanoic acid NHS ester
Me methyl
MeOH methanol
Mmt 4-methoxytrityl
MS mass spectrum/mass spectrometry
MTBE methyl tert.-butyl ether
MW molecular mass
NHS N-hydroxy succinimide
Palm palmitoyl
iPrOH 2-propanol
PBS phosphate buffered saline
PEG polyethylene glycol
PK pharmacokinetic
PyBOP benzotriazole-1-yl-oxy-tris-pyrrolidino-phosphonium hexafluorophosphate Phth phthalimido
RP-HPLC reversed-phase high performance liquid chromatography
rpm rounds per minute
RT room temperature
SEC size exclusion chromatography
Stea stearyl
TCEP tris(2-carboxyethyl)phosphine hydrochloride
TES triethylsilane
TFA trifluoroacetic acid
THF tetrahydrofurane
TMEDA N,N,N"N"-tetramethylethylene diamine
Tris tris(hydroxymethyl)aminomethane
Trt trityl
UPLC Ultra Performance Liquid Chromatography
UV ultraviolet
V volume General Synthesis of Peptidic Compounds Materials:

Different Rink-Amide resins (4-(2',4'-Dimethoxyphenyl-Fmoc-aminomethyl)-phenoxyacetamido-norleucylaminomethyl resin, Merck Biosciences; 4-[(2,4-Dimethoxyphenyl)(Fmoc-amino)methyl]phenoxy acetamido methyl resin, Agilent Technologies) were used for the synthesis of peptide amides with loadings in the range of 0.2-0.7 mmol/g.

Fmoc protected natural amino acids were purchased from Protein Technologies Inc., Senn Chemicals, Merck Biosciences, Novabiochem, Iris Biotech, Nagase or Bachem. The following standard amino acids were used throughout the syntheses: Fmoc-L-Ala-OH, Fmoc-L-Asp(OtBu)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Lys(Mmt)-OH, Fmoc-L-Phe-OH, Fmoc-L-Pro-OH, Fmoc-L-Ser(tBu)-OH, Fmoc-D-Ser(Boc)-OH, Fmoc-L-Thr(tBu)-OH, Fmoc-L-Trp(Boc)-OH.

In addition, the following special amino acids were purchased from the same suppliers as above: Fmoc-L-Lys(ivDde)-OH, Fmoc-Aib-OH, Fmoc-D-Ser(tBu)-OH, Fmoc-D-Ala-OH, Boc-L-His(Boc)-OH (available as toluene solvate) and Boc-L-His(Trt)-OH.

The solid phase peptide syntheses were performed for example on a Prelude Peptide Synthesizer (Protein Technologies Inc.) or similar automated synthesizer using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF 2× for 20 min. Washes: 5×DMF.

In cases where a Lys-side-chain was modified, Fmoc-L-Lys(ivDde)-OH or Fmoc-L-Lys(Mmt)-OH was used in the corresponding position. After completion of the synthesis, the ivDde group was removed according to a modified literature procedure (S. R. Chhabra et al., Tetrahedron Lett. 39, (1998), 1603), using 4% hydrazine hydrate in DMF. The Mmt group was removed by repeated treatment with 1% TFA in dichloromethane. The following acylations were carried out by treating the resin with the N-hydroxy succinimide esters of the desired acid or using coupling reagents like HBTU/DIPEA or HOBt/DIC.

All the peptides that had been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analyzed by analytical HPLC and checked by ESI mass spectrometry. Crude peptides were purified by a conventional preparative HPLC purification procedure.

Analytical HPLC/UPLC

Analytical HPLC was performed on an Agilent 1100 Series HPLC system with a Waters XBridge BEH130 3.5 µm C18 column (2.1×150 mm) at 40° C. with a gradient elution at a flow rate of 0.5 mL/min and monitored at 215 and 280 nm. The gradients were set up as 10% B to 90% B over 15 min and then 90% B for 1 min or as 15% B to 50% B over 12.5 min and then 50% B to 90% B over 3 min. Buffer A=0.1% formic acid in water and B=0.1% formic acid in acetonitrile.

General Preparative HPLC Purification Procedure:

The crude peptides were purified either on an Äkta Purifier System or on a Jasco semiprep HPLC System. Preparative RP-C18-HPLC columns of different sizes and with different flow rates were used depending on the amount of crude peptide to be purified. Acetonitrile+0.1% TFA (B) and water +0.1% TFA (A) were employed as eluents. Product-containing fractions were collected and lyophilized to obtain the purified product.

LCMS Method A: Detection at 215 nm
column: Aeris Widepore, 3.6 µm, 100×2.1 mm at 40° C.
solvent: H$_2$O+0.1% TFA:ACN+0.1% TFA (flow 0.5 ml/min)
gradient: 90:10 (0 min) to to 10:90 (10 min) to 10:90 (10.67 min) to 90:10 (11 min) to 90:10 (12 min)

Stability-Testing of Exendin-4 Derivatives

Prior to the testing of solubility and stability of a peptide batch, its content was determined. Therefore, two parameters were investigated, its purity (HPLC-UV) and the amount of salt load of the batch (ion chromatography).

For stability testing, an aliquot of the supernatant obtained for solubility was stored for 7 days at 25° C. or 40° C. After that time course, the sample was centrifuged for 20 min at 4000 rpm and the supernatant was analysed with HPLC-UV.

For determination of the amount of the remaining peptide, the peak areas of the target compound at t0 and t7 were compared, resulting in "% remaining peptide", following the equation $$\% \text{ remaining peptide} = [(\text{peak area peptide } t7) \times 100] / \text{peak area peptide } t0.$$

The amount of soluble degradation products was calculated from the comparison of the sum of the peak areas from all observed impurities reduced by the sum of peak areas observed at to (i.e. to determine the amount of newly formed peptide-related species). This value was given in percentual relation to the initial amount of peptide at t0, following the equation:

$$\% \text{ soluble degradation products} = \{[(\text{peak area sum of impurities } t7) - (\text{peak area sum of impurities } t0)] \times 100\} / \text{peak area peptide } t0.$$

The potential difference from the sum of "% remaining peptide" and "% soluble degradation products" to 100% reflects the amount of peptide which did not remain soluble upon stress conditions following the equation:

$$\% \text{ precipitate} = 100 - ([\% \text{ remaining peptide}] + [\% \text{ soluble degradation products}])$$

This precipitate includes non-soluble degradation products, polymers and/or fibrils, which have been removed from analysis by centrifugation.

The chemical stability is expressed as "% remaining peptide".

Anion Chromatography

Instrument: Dionex ICS-2000, pre/column: Ion Pac AG-18 2×50 mm (Dionex)/AS18 2×250 mm (Dionex), eluent: aqueous sodium hydroxide, flow: 0.38 mL/min, gradient: 0-6 min: 22 mM KOH, 6-12 min: 22-28 mM KOH, 12-15 min: 28-50 mM KOH, 15-20 min: 22 mM KOH, suppressor: ASRS 300 2 mm, detection: conductivity.

In vitro cellular assays for GLP-1 receptor and glucagon receptor efficacy Peptidic compounds of Seq. ID No. 5 and 6 were prepared according to the methods described in WO2014056. Potencies of peptidic compounds at the GLP-1 and glucagon receptors were determined by exposing cells expressing human glucagon receptor (hGlucagon R) or human GLP-1 receptor (hGLP-1 R) to the listed compounds at increasing concentrations and measuring the formed cAMP. Agonism of peptides for the receptors was determined by functional assays measuring cAMP response of HEK-293 cell lines stably expressing human GIP, GLP-1 or glucagon receptor.

cAMP content of cells was determined using a kit from Cisbio Corp. (cat. no. 62AM4PEC) based on HTRF (Homogenous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 µl-aliquots dispensed into the wells of 96-well plates. For measurement, 25 µl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/620 nm. In vitro potency of agonists was quantified by determining the concentrations that caused 50% activation of maximal response (EC50).

Hydrogel Analytical Methods

Estimation of maleimide content in hyaluronic acid hydrogels.

Estimation of maleimide groups incorporated to HA hydrogels was performed by a colorimetric analysis method. 5-Thio 2-nitrobenzoic acid was prepared by the reduction of 5,5'-dithiobis-(2-nitrobenzoic acid) with Tris-(2-carboxyethyl) phosphine hydrochloride (TCEP) in PBS buffer at pH 7.5. A 20 mol % excess of 5,5'-dithiobis-(2-nitrobenzoic acid) was used to prevent side reactions with TCEP. A predetermined amount of maleimide functionalized hydrogel suspended in 20 mM Succinate buffered saline (SBS) at pH 3.5. Above 5-Thio 2-nitrobenzoic acid solution was added to the hydrogel suspension and the reaction mixture was vortex mixed (2×10 seconds) and was subsequently stirred gently at 25° C. for 45 min. The suspension was subsequently centrifuged at 25° C. for 10 min and an aliquot of the supernatant taken. The absorbance of the supernatant was measured at 412 nm. The concentration 5-thio 2-nitrobenzoic acid in the solution was estimated using a calibration curve. Maleimide concentration in the hydrogels is equivalent to the moles of thiol reacted, which is calculated from the difference between the amount 5-thio 2-nitrobenzoic acid added and that present in the supernatant.

Procedure for Estimation of Peptide Loading in the Hydrogel-Peptide Conjugates

A predetermined amount HA hydrogel-peptide conjugate was suspended in CHES buffer (pH9.5) and the suspension was allowed to gently stir at 70° C. The suspension was centrifuged and the aliquot was analyzed for peptide content by HPLC method. The HPLC method comprises of using q C-18 Kinetics column (inner diameter=4.6 mm and length=100 mm, particle size 2.6 µm, Phenomenex) using Agilent 1100 LC. The composition of mobile phase A is 90% water/10% Acetonitrile/0.1% Trifluoroacetic acid (TFA) and the mobile phase B is 10% Acetonitrile/90% water/0.09% TFA. The gradient is from mobile phase 25% B to 55% B in 8 minutes. The flow rate was kept at 1 mL/min. Pure peptides were used as standards to quantify the released peptide from the hydrogel.

Quantitative Analysis with $^1$H-NMR (Nuclear Magnetic Resonance)

Solid state or (Gel state) MAS (magic angle spinning) Proton NMR was used for characterization of the HA-hydrogel conjugates. In a version, the sample was swollen in D2O with expedients to enhance the line shape of the resulting NMR spectra and loaded into a ZrO2 (Zirconium dioxide) rotor. The rotor was placed in a MAS probe installed in a 400 MHz magnet, capable to rotate the sample at high rotation (4-13 KHz) speed under magic angle (54.7°) condition. Significant line shape narrowing results and leads to acquisition of NMR spectra useful to estimate the degree of cross-linking (p.e. DVS)
   the degree of hydrogel functionalization (p.e. maleimide)
   the peptide loading of HA hydrogel
   the amount of free peptide not bound to the polymer backbone
   the determination of residual free small molecules e.g. solvents or reagents
   the determination of conjugate purity In a version of experiment, broadband homonuclear decoupled T2 spin-spin relaxation filter was used to suppress broad signals of the Hyaluronic acid backbone resonances.

In a version of the experiment, diffusion ordered NMR experiment was used to suppress non polymer bound small molecule or peptide components. DOSY mixing times of up to 800 ms at maximum MAS rates was used. The DOSY filter enabled a direct prove for the chemical substitution of the substitutents to the polymer backbone. All experiments were performed without chemical decomposition of the HA bio conjugate directly in its native state at the swollen condition.

In a version of the analyses, diffusion and T2 spin-spin relaxation filter were combined in a hybrid experiment to establish 1) connectivity of the substitutent to the backbone of the polymer 2) to edit the complex spin system by its T2 relaxation rates.

Sample Preparation of HA Conjugates for NMR

Stock Solution:

An exact amount of 5 to 10 mg Maleic acid was weighed into a 5 mL flask and 1.5 mL 2,2,2-Trifluoroethanol-$d_3$ was added. Then the flask was filled to 5 mL with $D_2O$. This mixture was used as stock solution for subsequent swelling of the lyophilized HA material.

Preparation of HA Conjugate Gel:

An exact amount of 3 to 5 mg of the HA conjugate was weight into an Eppendorf-Cap and 150 µL stock solution was added. The Eppendorf-Cap was shaken with a vortexer before the gel formation started. The gel was kept overnight at room temperature. Then the gel was placed into a HR-MAS-Rotor. The rotor was measured in a solid state NMR spectrometer at 9.39 T, which corresponds to a proton resonance of 400.13 MHz. In order to reduce dipole-dipole interactions the rotor was adjusted to a magic angle ca. 54.7° and spun at 10 KHz. A proton spectrum was recorded with a Recycle Delay of 25 sec and 2048 Scans.

Evaluation:

After recording of the data, the FID (free induction decay) was subjected to window multiplication and Fourier transformation. The spectra were phase corrected and a baseline correction routine was applied to the spectra before signal integration. The proton signals of a the aromic functions from 7.5 to ca. 7 ppm were integrated and calculated to the corresponding numbers of the aromatic protons of the peptide. The same was done for the maleic acid signal of the internal standard. Both values were set into ratio for estimation of the peptide loading. For other structural features of the conjugates the proton signals shown in Table 2 were used.

TABLE 2

| Structural feature | Analyzed NMR signal | Reference |
| --- | --- | --- |
| Degree of DVS crosslinking | Ethylene protons of DVS after coupling at 3 to 3.8 ppm | Acetyl protons of HA sugar units at 1.6 to 1.8 ppm |
| Degree of maleimide functionalisation | Olefinic protons of maleimide at 6.7 ppm | Acetyl protons of HA sugar units at 1.6 to 1.8 ppm |
| Peptide loading | Aromatic amino acid protons at 6.8 to 7.5 ppm | Acetyl protons of HA sugar units at 1.6 1.8 ppm |

FIG. 2 shows a typical 1H-NMR spectra of HA-hydrogel-Aib-linker conjugate of peptide of Seq. ID NO: 5.

EXAMPLES

Example 1

Synthesis of Aib-Linker-Peptide Conjugate with SEQ ID NO: 5

The solid phase synthesis was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.34 mmol/g. The Fmoc-synthesis strategy was applied with HBTU/DIPEA-activation. In position 14 Fmoc-Lys(Mmt)-OH and in position 1 Fmoc-His(Trt)-OH were used in the solid phase synthesis protocol. Then Fmoc-Aib-OH was coupled.

Then the Mmt-group was cleaved from the peptide on resin by repeated (8×) treatment with 1% TFA in dichloromethane. Then the resin was treated 3×3% DIPEA in dichloromethane and then washed 3× with dichloromethane, followed by 3×DMF. Hereafter N-hydroxy succinimide ester Palm-Glu(γOSu)-OtBu (3 eq. in DMF) was coupled to the liberated amino-group followed by Fmoc-cleavage.

After the Fmoc cleavage the linker reagent 5c was coupled (2 eq. in DMF).

The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (Sunfire, Prep C18) using an acetonitrile/water gradient (both buffers with 0.1% TFA).

Finally, the molecular mass of the purified peptide was confirmed by LC-MS.

Example 2

Synthesis Asn-Linker-Peptide Conjugate Using SEQ ID NO: 5

The solid phase synthesis as described in Methods was carried out on Rink-Amide resin (4-(2',4'-Dimethoxyphenyl-Fmoc-aminomethyl)-phenoxyacetamido-norleucylaminomethyl resin). The Fmoc-synthesis strategy was applied with HBTU/DIPEA-activation. In position 14 Fmoc-Lys(ivDde)-OH and in position 1 Fmoc-His(Trt)-OH were used in the solid phase synthesis protocol.

Linker attachment: After cleavage of the N-terminal Fmoc group using the standard protocol, 2.5 equivalents 7e, 3 equivalents PyBOP, and 3 equivalents DIPEA in DMF (50 ml per mmol peptide) we mixed. After 15 minutes, the resin-bound peptide was added and the mixture was reacted under gentle shaking for 16 h at ambient temperature. Then the solvent was removed by filtration and the filtrate was washed subsequently with DMF, DCM, iso-propanol and diethyl ether.

Lysine acylation and cleavage: The ivDde-group was cleaved from the peptide on resin according to literature (S. R. Chhabra et al., Tetrahedron Lett. 39, (1998), 1603). Hereafter, Palm-gGlu-OSu was coupled to the liberated amino-group employing DIPEA as base. The peptide was cleaved from the resin with King's cocktail (D. S. King, C. G. Fields, G. B. Fields, Int. J. Peptide Protein Res. 36, 1990, 255-266). The crude product was purified via preparative HPLC on a Waters column (XBridge, BEH130, Prep C18 5 µM) using an acetonitrile/water gradient (both buffers with 0.1% TFA). The purified peptide-linker conjugate was analysed by LCMS (Method A), molecular ion peak, m/z 1189, z=4).

Example 3

Synthesis of Linker Reagent 5c

Linker reagent 5c was synthesized according to the following scheme:

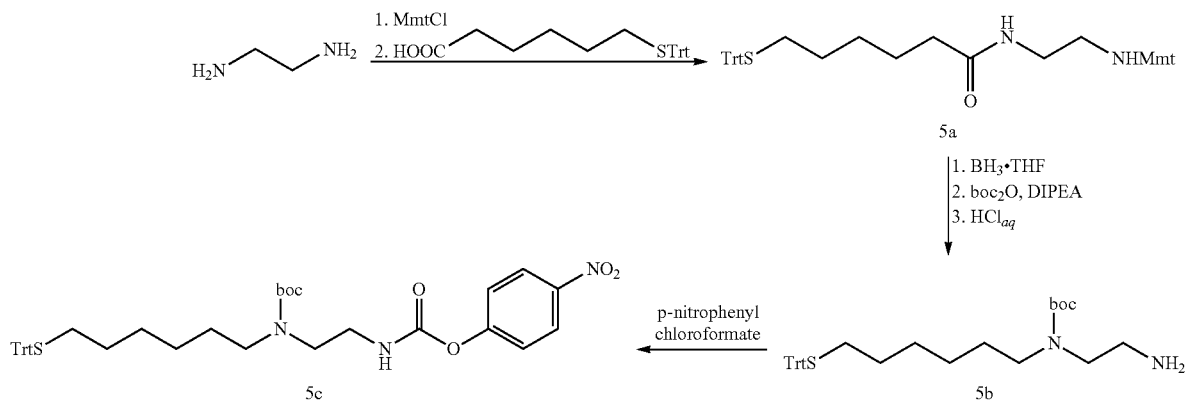

Synthesis of Linker Reagent Intermediate 5a:

m-Methoxytrityl chloride (3 g, 9.71 mmol) was dissolved in DCM (20 mL) and added dropwise to a solution of ethylenediamine (6.5 mL, 97.1 mmol) in DCM (20 mL). After two hours the solution was poured into diethyl ether (300 mL) and washed three times with 30/1 (v/v) brine/0.1 M NaOH solution (50 ml each) and once with brine (50 mL). The organic phase was dried over $Na_2SO_4$ and volatiles were removed under reduced pressure. Mmt-protected intermediate (3.18 g, 9.56 mmol) was used in the next step without further purification.

The Mmt-protected intermediate (3.18 g, 9.56 mmol) was dissolved in anhydrous DCM (30 mL). 6-(S-Tritylmercapto)hexanoic acid (4.48 g, 11.47 mmol), PyBOP (5.67 g, 11.47 mmol) and DIPEA (5.0 mL, 28.68 mmol) were added and the mixture was agitated for 30 min at RT. The solution was diluted with diethyl ether (250 mL) and washed three times with 30/1 (v/v) brine/0.1 M NaOH solution (50 mL each) and once with brine (50 mL). The organic phase was dried over $Na_2SO_4$ and volatiles were removed under reduced pressure. 5a was purified by flash chromatography.

Yield: 5.69 g (8.09 mmol).

MS: m/z 705.4=$[M+H]^+$ (MW calculated=705.0).

Synthesis of Linker Reagent Intermediate 5b:

To a solution of 5a (3.19 g, 4.53 mmol) in anhydrous THF (50 mL) was added $BH_3$·THF (1 M solution, 8.5 mL, 8.5 mmol) and the solution was stirred for 16 h at RT. Further $BH_3$·THF (1 M solution, 14 mL, 14 mmol) was added and stirred for 16 h at RT. The reaction was quenched by addition of methanol (8.5 mL). N,N-dimethyl-ethylenediamine (3 mL, 27.2 mmol) was added and the solution was heated to reflux and stirred for three h. Reaction mixture was allowed to cool down to RT and was then diluted with ethyl acetate (300 mL), washed with saturated, aqueous $Na_2CO_3$ solution (2×100 mL) and saturated, aqueous $NaHCO_3$ solution (2×100 mL). The organic phase was dried over $Na_2SO_4$ and volatiles were removed under reduced pressure to obtain crude amine intermediate (3.22 g).

The amine intermediate (3.22 g) was dissolved in DCM (5 mL). $Boc_2O$ (2.97 g, 13.69 mmol) dissolved in DCM (5 mL) and DIPEA (3.95 mL, 22.65 mmol) were added and the mixture was agitated at RT for 30 min. The mixture was purified by flash chromatography to obtain the crude Boc- and Mmt-protected intermediate (3.00 g).

MS: m/z 791.4=$[M+H]+$, 519.3=$[M-Mmt+H]^+$ (MW calculated=791.1).

0.4 M aqueous HCl (48 mL) was added to a solution of the Boc- and Mmt-protected intermediate in acetonitrile (45 mL). The mixture was diluted with acetonitrile (10 mL) and stirred for 1 h at RT. Subsequently, the pH value of the reaction mixture was adjusted to 5.5 by addition of 5 M NaOH solution. Acetonitrile was removed under reduced pressure and the aqueous solution was extracted with DCM (4×100 mL). The combined organic phases were dried over $Na_2SO_4$ and volatiles were removed under reduced pressure. Crude 5b was used in the next step without further purification.

Yield: 2.52 g (3.19 mmol).

MS: m/z 519.3=$[M+H]^+$ (MW calculated=519.8 g/mol).

Synthesis of Linker Reagent 5c:

Intermediate 5b (985 mg, 1.9 mmol) and p-nitrophenyl chloroformate (330 mg, 2.5 mmol) were dissolved in anhydrous THF (10 mL). DIPEA (0.653 mL, 3.7 mmol) was added and the mixture was stirred for 2 h at RT. The solution was acidified by addition of acetic acid (1 mL). 5c was purified by RP-HPLC.

Yield: 776 mg, (1.13 mmol).

MS m/z 706.3=$[M+Na]^+$ (MW calculated=706.3).

Example 4

Synthesis of Linker Reagent 7f (Asn Linker)

Linker reagent 7f was synthesized according to the following scheme:

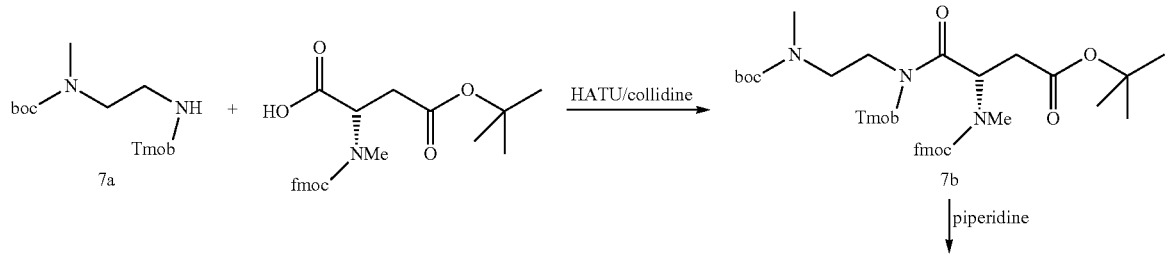

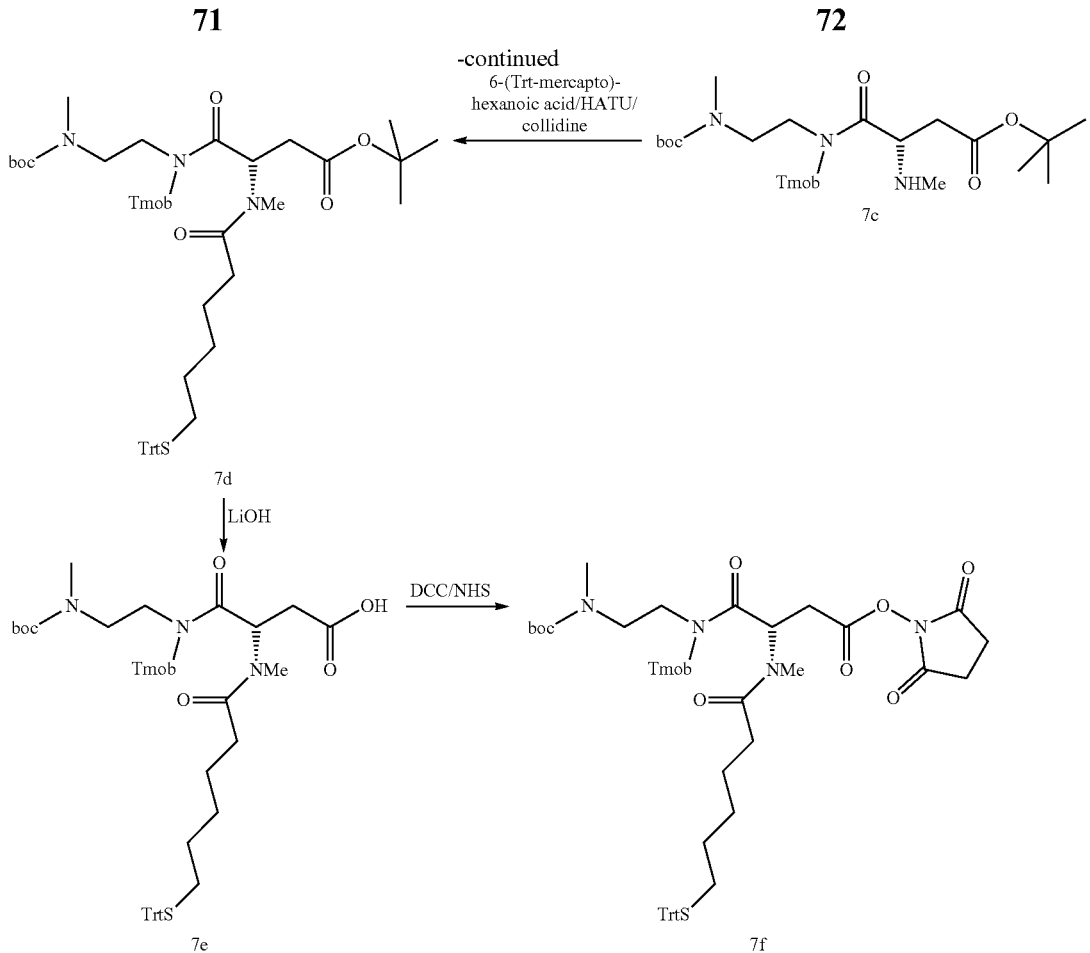

To a cooled (0° C.) solution of N-Methyl-N-boc ethylenediamine (0.5 mL, 2.79 mmol) and NaCNBH$_3$ (140 mg, 2.23 mmol) in MeOH (10 mL) and acetic acid (0.5 mL) was added a solution of 2,4,6-trimethoxybenzaldehyde (0.547 mg, 2.79 mmol) in EtOH (10 mL). The mixture was stirred at RT for 2 h, acidified with 2 M HCl (1 mL) and neutralized with saturated aqueous Na$_2$CO$_3$ (50 mL). Evaporation of all volatiles, DCM extraction of the resulting aqueous slurry and concentration of the organic fractions yielded N-Methyl-N-boc-N'-tmob-ethylendiamine (7a) as a crude oil which was purified by RP-HPLC.

Yield: 593 mg (1.52 mmol)

MS: m/z 377.35=[M+Na]$^+$, (calculated=377.14).

N-Fmoc-N-Me-Asp(OtBu)-OH (225 mg, 0.529 mmol) was dissolved in DMF (3 mL) and 7a (300 mg, 0.847 mmol), HATU (201 mg, 0.529 mmol), and collidine (0.48 mL, 3.70 mmol) were added. The mixture was stirred at RT for 2 h to yield 7b. For fmoc deprotection, piperidine (0.22 mL, 2.16 mmol) was added and stirring was continued for 1 h. Acetic acid (1 mL) was added, and 7c was purified by RP-HLPC.

Yield: 285 mg (0.436 mmol as TFA salt)

MS: m/z 562.54=[M+Na]$^+$, (calculated=562.67).

6-Tritylmercaptohexanoic acid (0.847 g, 2.17 mmol) was dissolved in anhydrous DMF (7 mL). HATU (0.825 g, 2.17 mmol), and collidine (0.8 mL, 6.1 mmol) and 7c (0.78 g, 1.44 mmol) were added. The reaction mixture was stirred for 60 min at RT, acidified with AcOH (1 mL) and purified by RP-HPLC. Product fractions were neutralized with saturated aqueous NaHCO$_3$ and concentrated. The remaining aqueous phase was extracted with DCM and 7d was isolated upon evaporation of the solvent.

Yield: 1.4 g (94%)

MS: m/z 934.7=[M+Na]$^+$, (calculated=934.5).

To a solution of 7d (1.40 mg, 1.53 mmol) in MeOH (12 mL) and H$_2$O (2 mL) was added LiOH (250 mg, 10.4 mmol) and the reaction mixture was stirred for 14 h at 70° C. The mixture was acidified with AcOH (0.8 mL) and 7e was purified by RP-HPLC. Product fractions were neutralized with saturated aqueous NaHCO$_3$ and concentrated. The aqueous phase was extracted with DCM and 7e was isolated upon evaporation of the solvent.

Yield: 780 mg (60%)

MS: m/z 878.8=[M+Na]$^+$, (calculated=878.40).

To a solution of 7e (170 mg, 0.198 mmol) in anhydrous DCM (4 mL) were added DCC (123 mg, 0.59 mmol) and N-hydroxy-succinimide (114 mg, 0.99 mmol), and the reaction mixture was stirred for 1 h. The mixture was filtered, and the filtrate was acidified with 0.5 mL AcOH and 7f purified by RP-HPLC. Product fractions were neutralized with saturated aqueous NaHCO$_3$ and concentrated. The remaining aqueous phase was extracted with DCM and 7f was isolated upon evaporation of the solvent.

Yield: 154 mg (0.161 mmol)

MS: m/z 953.4=[M+H]$^+$, (calculated=953.43).

Example 5

Synthesis of Linker Reagent 8e

Linker reagent 8e was synthesized according to the following scheme:

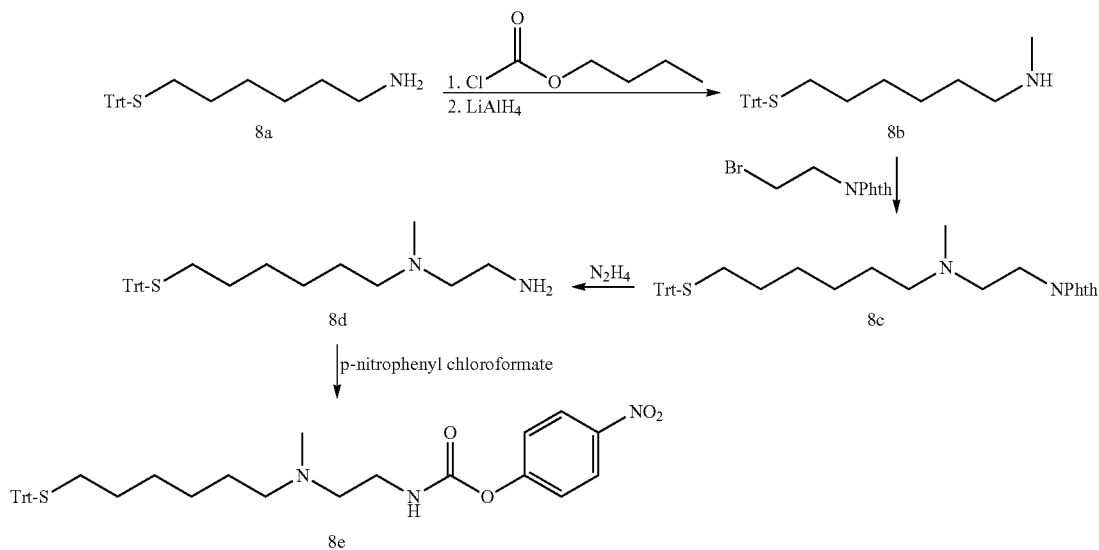

Synthesis of linker reagent intermediate 8b was performed under nitrogen atmosphere. A solution of amine 8a (1.69 g, 4.5 mmol, for preparation see WO-A 2009/133137) in 30 mL THF (dry, mol. sieve) was cooled to 0° C. Butyl chloroformate (630 µl, 4.95 mmol) in 3 mL THF (dry, mol. sieve) and DIPEA (980 µl, 5.63 mmol) were added. Mixture was stirred for 10 min at 0° C., cooling was removed and mixture stirred for further 20 min at RT. 1 M LiAlH$_4$ in THF (9 mL, 9 mmol) was added and mixture was refluxed for 1.5 h. Reaction was quenched by slowly adding methanol (11 mL) and 100 mL sat. Na/K tartrate solution. Mixture was extracted with ethyl acetate, organic layer was dried over Na$_2$SO$_4$ and solvent was evaporated under reduced pressure. Crude product 8b (1.97 g) was used in the next step without further purification.

MS: m/z 390.2=[M+H]$^+$ (MW calculated=389.6).

A solution of crude product 8b (1.97 g), N-(bromoethyl)-phthalimide (1.43 g, 5.63 mmol) and K$_2$CO$_3$ (1.24 g, 9.0 mmol) in 120 mL acetonitrile was refluxed for 6 h. 60 mL of a sat. NaHCO$_3$ solution was added and mixture was extracted 3× with ethyl acetate. Combined organics were dried (Na$_2$SO$_4$) and solvent was removed under reduced pressure. Phthalimide 8c was purified on silica by using heptane (containing 0.02% NEt$_3$) and an ascending amount of ethyl acetate (containing 0.02% NEt$_3$) as eluents.

Yield: 0.82 g (1.46 mmol)

MS: m/z 563.3=[M+H]$^+$ (MW calculated=562.8).

Phthalimide 8c (819 mg 1.46 mmol) was dissolved in 35 mL ethanol and hydrazine hydrate (176 µl, 3,64 mmol) was added. Mixture was refluxed for 3 h. Precipitate was filtered off. Solvent was removed under reduced pressure and residue was treated with 15 mL dichloromethane. Precipitate was filtered off and dichloromethane was removed under reduced pressure. Residue was purified by RP HPLC. Pooled HPLC fractions were adjusted to pH 7 by adding NaHCO$_3$ and extracted several times with dichloromethane. Combined organics were dried (Na$_2$SO$_4$) and solvent was removed under reduced pressure to yield amine 8d.

Yield: 579 mg (1.34 mmol)

MS: m/z 433.3=[M+H]$^+$ (MW calculated=432.7).

Para-nitrophenyl chloroformate (483 mg, 2.40 mmol) was dissolved in 10 mL dichloromethane (dry, mol. sieve). A solution of amine 8d (1.00 g, 2.31 mmol) in 5 mL dichloromethane (dry, mol. sieve) and 1.8 mL of sym-collidine were added and mixture was stirred at room temperature for 40 min. Dichloromethane was removed under reduced pressure, residue was acidified with acetic acid and purified by RP-HPLC to yield para-nitrophenyl carbamate 8e.

Yield: 339 mg (0.57 mmol)

MS: m/z 598.3=[M+H]$^+$ (MW calculated=597.8).

Example 6

In Vitro Cellular Assays for GLP-1 Receptor and Glucagon Receptor Efficacy

Peptidic compounds of Seq. ID No. 5 and 6 were prepared according to the methods described in WO2014056. Potencies of peptidic compounds at the GLP-1 and glucagon receptors were determined by the methods described above exposing cells expressing human glucagon receptor (hGlucagon R) or human GLP-1 receptor (hGLP-1 R).

The results are shown in Table 3:

TABLE 3

| EC50 values of exendin-4 derivatives at GLP-1 and Glucagon receptors (indicated in pM) | | |
|---|---|---|
| SEQ ID NO | EC50 hGLP-1R | EC50 hGlucagon-R |
| 5 | 1.9 | 9.4 |
| 6 | 5.1 | 9.1 |

Synthesis of Hyaloronic Acid Hydrogels

Example 7

Divinyl Sulfone Crosslinked Hyaluronic Acid

Example 7a

To 0.2M sodium hydroxide (168.9 g) was added sodium chloride (23.4 g) with stirring until dissolved. To the solution under rapid mechanical stirring was added sodium hyaluronate (25.4 g, 400-500 KDa) which continued for 2 h. The resulting polymer solution has a concentration of ~12% w/w. A solution of divinylsulfone (0.41 mL, 0.48 g) in isopropanol (1.6 mL) was prepared and added (5×0.4 mL) over ~30 sec. The mixture was stirred for an additional 2 min and poured into a 23×28×6.5 cm glass tray and sealed with a plastic cover. After standing at RT for 4 h the gel was transferred as a single piece to a solution of 1M hydrochloric acid (100.1 g) in 0.9% saline (3 kg). It was agitated gently at RT. After 24 h the pH of the solution was 2.28. The solution discarded leaving a gel (416.2 g). To the gel was then added 0.9% saline (3 kg) and it was agitated gently at RT for 18 h. To the mixture was added 1M sodium hydroxide (9.7 mL) at 0,2,4,6 and 8 h. The gel was gently agitated for a further 24 h at RT at which time the pH of the gel was 6.65. The gel was stored at 2-8° C. for 120 h and then 10 mM sodium phosphate solution pH 7.4 (2 L) was added. The gel was agitated for an additional 21 h and the wash discarded leaving a gel (1036.2 g) with a final polymer concentration of 2.4%.

Example 7b

Alternative Synthesis of Divinylsulfone Crosslinked Hyaluronic Acid

To 35 g of sodium hyaluronate was added 946 mL of sterile water. The reaction mixture was kept at 2-8° C. for 7 days, during which time a clear solution has formed. To this solution was added 1M 111 mL of 1.0 M sodium hydroxide solution and the resulting reaction mixture was stirred vigorously for 5 min. The reaction mixture was kept at 2-8° C. for 90 min. Subsequently a suspension of 6.7 mL of divinylsulfone in 10 mL of sterile water was to the polymer solution and the resulting reaction mixture was stirred vigorously for 5 minutes. Subsequently, reaction mixture was stored at 2-8° C. for 150 minutes followed by for 90 minutes at 25° C. The polymer gel thus formed was washed with 0.9% sterile saline for four days. The pH of the suspension was adjusted to 7.0 with either 1.)M NaOH or 1.0 M HCl. The final concentration of the gel suspension was 0.58%.

Example 8

Synthesis of 1-(tert-butoxycarbonyl) amino 3-(3-maleimidopropyl) aminopropane

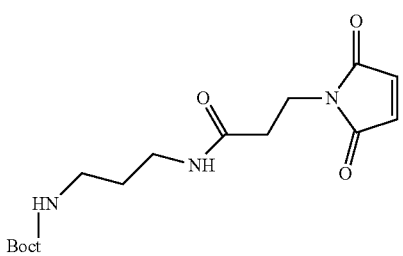

In 250 ml round bottomed flask were taken 3.0 g of 1-(tert-Butoxycarbonyl) amino 3-aminopropane) and 100 mL of anhydrous chloroform. The reaction mixture was stirred at 25° C. until a clear solution was formed. To this solution was added N-succinimidyl 3-maleimidopropionate (5.05 g) with stirring until dissolved followed 3.42 mL of diisoproylethylamine. The resulting reaction mixture was stirred at 25° C. for 18 h. The solution was washed with 1M hydrochloric acid (50 mL), 10% brine (50 mL), saturated sodium bicarbonate (50 mL), semi-saturated brine (50 mL). The organic phase was isolated and was dried over anhydrous sodium sulfate. After removing the sodium sulfate by filtration, the solution was concentrated under reduced pressure and the residue was purified by silica gel column chromatography using ethyl acetate: hexanes gradient as the mobile phase. Removal of the solvent under reduced pressure followed by vacuum drying offered the desired product as an off white solid (4.03 g).

Example 9

Synthesis of 1-amino 3-(3-maleimidopropyl) aminopropane methyl sulfonate

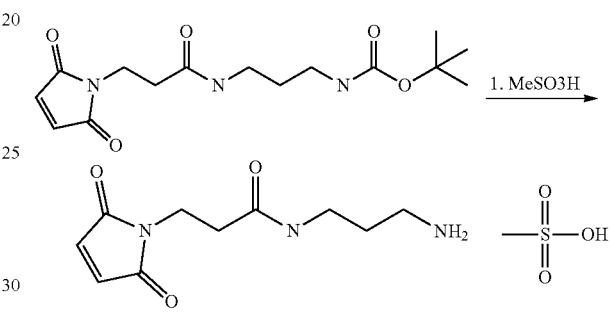

0.25 mol (80 g) of 1-(tert-Butoxycarbonyl) amino 3-aminopropane) were dissolved in 400 mL acetone. 35 mL (2.19 eq) methanesulfonic acid were added dropwise until the gas formation was ended (1.5 h) at 35° C.

After cooling to room temperature the product was washed with acetone (3×50 mL) and dried at 40° C. and 20 mbar.

The crude product was purified by treatment with 200 mL acetone at 56° C. for 1 h. After filtration at 40° C. the product washed with acetone (3×50 mL) and dried at 40° C. and 20 mbar, (Yield: 76.2 g reddish solid, 96%)

Example 10

General Method for the synthesis of 3-(3-maleimido-propyl) aminopropane functionalized HA hydrogel To appropriate amount divinylsulphone crosslinked HA suspension (Example 7b) was added sterile saline to obtain a gel concentration of ~1% w/v. The resulting suspension was stirred at 25° C. for 15-30 minutes. A water miscible organic solvent (preferably ethanol) was added to the suspension and the resulting suspension was stirred for additional 30-60 min. To this suspension was added appropriate amount of an ethanolic solution of 4-(4,6-dimethoxy-1,3,5-triazin-2-yl)-4-methyl-morpholinium chloride (DMT-MM). The container containing DMT-MM solution was rinsed twice with ethanol and the washings were added to the above suspension. The resulting reaction mixture was stirred at 25° C. for 90 minutes. Appropriate amount of 1-(tert-butoxycarbonyl) amino 3-(3-maleimidopropyl) aminopropane was dissolved in dichloromethane. To this solution was added trifluoroacetic acid to give a 1:1(v/v) solution. After stirring at room temperature for 60-90 minutes, the reaction mixture was evaporated to dryness under reduced pressure. The residue was dissolved in ethanol and was added to the above suspension. The container containing maleimide derivative was rinsed twice with ethanol and the washings were added to the suspension. The pH of the suspension was adjusted to pH 6.4-6.6 using an organic or inorganic base (for example 10% N-methylmopholine in ethanol). After stirring for 16-20 h at 25° C., the suspension was treated with ethanol to a volume of 60-65% v/v. The solvent was removed from the reaction mixture either by centrifugation at 120 G followed by decanting the supernatant or by applying a slight overpressure of $N_2$ gas to the system and filtering through a glass frit or filter membrane. The residue was subsequently treated with sterile 20 mM succinate saline (0.9%) at pH 3.8 for ~15-20 min and was precipitated by adding ethanol to a volume of 60-65% v/v. The solvent is removed from the reaction mixture by following the above procedure. This procedure was repeated one more time.

Example 11

Conjugation of Linker Thiol Peptides to Maleimide Functionalized HA Hydrogel

General procedure for the thiol terminated trace-linker bearing peptides to maleimide functionalized HA hydrogels.

In a sterile and depyrogenated reactor with medium porosity frit or filter was taken appropriate amount of the maleimide modified HA hydrogel (example 10). Subsequently, appropriate amount of sterile filtered 20 mMol SB buffer (containing 15% v/v propylene glycol and 0.01% w/v Tween 20, pH 3.8) was added to the reaction such that the concentration of the resulting suspension is ~1% w/w. The suspension was allowed to mix for 30-90 minutes with gentle shaking. At the end of this time, appropriate amount of thiol terminated trace-linker bearing peptide dissolved in sterile filtered 20 mMol SB buffer (containing 15% v/v propylene glycol and 0.01% w/v Tween 20, pH 3.8) was added to the reactor and the resulting reaction mixture was allowed to shake gently at ambient temperature for 1.5-24 hours. At the end of the reaction, the supernatant was removed by filtration using a slight excess pressure of nitrogen or by centrifugation of the suspension. The residue was treated with sterile filtered 20 mM SBS buffer (containing 15% v/v propylene glycol and 0.01% w/v Tween 20, pH 3.0) to prepare a suspension 0.7w/v %, shaken for 3 minutes, centrifuged and the supernatant was removed by decantation. This process was repeated five times. The residue was treated with 10 mM solution of 1-Hydroxy-2-mercaptoethane dissolved in sterile filtered 20 mM SBS buffer (containing 15% v/v propylene glycol and 0.01% w/v Tween 20, pH 3.0) to prepare a ~1 wt % suspension and was allowed to stir gently for 30 minutes with gentle shaking/mixing. The solvent was removed by centrifugation followed by decantation as mentioned above. This process of 1-Hydroxy-2-mercaptoethane treatment was repeated four times. The residue was suspended in sterile filtered 20 mM SBS buffer (containing 15% v/v propylene glycol and 0.01% w/v Tween 20, pH 3.0) to prepare a suspension of ~0.5 wt % concentration and mixed for 3 minutes followed by removal of the by centrifugation and decantation. The resulting residue was suspended in 20 mM SBS buffer (containing 15% v/v propylene glycol and 0.01% w/v Tween 20, pH 6.5) to prepare a 0.7 wt % suspension and stirred for 20 minutes and filtered. After repeating this process one more time, the residue was in 20 mM SBS buffer (containing 15% v/v propylene glycol and 0.01% w/v Tween 20, pH 4.5) to prepare a 0.5 wt. % suspension, stirred for 15 minutes, and filtered. This process was repeated once. The residue was suspended in sterile water (pH 4.5), stirred for 5 minutes, and filtered. The process was repeated five times and. The residue was aseptically filtered using a sterile membrane filter and lyophilized to dryness.

Example 12

Alternative Synthesis of HA-Aib-Linker-Peptide SEQ ID NO: 5 Conjugates

To 40 g of divinyl sulfone crosslinked Ha hydrogel suspension (0.92 g dry mass (0.00229 mol)) was added 100 ml of 0.9% NaCl solution in water and the resulting suspension was stirred at 25° C. for 10 minutes and transferred with 20 ml of 0.9% NaCl into the reactor. 70 mL was filtered off thereof.

After adding 50 ml of ethanol to the suspension, it was stirred for additional 30 min. It was followed by addition of a solution of 0.63 g (0.00229 mol, 1 eq.) 4-(4,6-dimethoxy-1,3,5-triazin-2-yl)-4-methyl-morpholinium (DMT-MM) chloride in 15 mL ethanol and was stirred for 1 h 30 min.

This was followed by addition of a solution of 0.15 g (0.00046 mol, 0.2 eq 1-amino 3-(3-maleimidopropyl) aminopropane-methyl sulfonate in 5 mL 0.9% NaCl. 10 mL ethanol was added and the pH adjusted to 6-6.5 with 10% N-methylmorpholine in ethanol and stirred overnight.

The suspension was filtered off and washed 2× with 50 mL 70% ethanol in buffer pH 3.8. Then washed with 50 mL 50% ethanol in buffer pH 3.8, then with 50 mL 20% ethanol in buffer pH 3.8, then with 50 mL buffer pH 3.8 (20 mM lactic acid, 0.9% NaCl, 0.01% Tween 20, pH adjusted with NaOH). Then 50 mL buffer pH 3.8 was added.

A solution of 108 mg (0.01 eq, 0.02 mmol) of Aib-linker-peptide conjugate with SEQ ID No. 5 (example 1) in 15 mL buffer pH 3.8 (20 mM lactic acid, 0.9% NaCl, 0.01% Tween 20, pH adjusted with NaOH) was added to the reactor. The flask with the conjugate solution was rinsed 2× with 5 mL buffer pH 3.8 and added to the reactor. The suspension was stirred overnight.

The suspension in the reactor was filtered off and washed 5×50 mL buffer pH 3.8.

The residue was treated with 50 mL 10 mM solution of 1-Hydroxy-2-mercaptoethane dissolved in sterile filtered 20 mM SBS buffer (containing 15% v/v propylene glycol and 0.01% w/v Tween 20, pH 3.8) and stirred for 1. Then 50 mL of 0.2 M lactic acid in sterile filtered 20 mM SBS buffer (containing 15% v/v propylene glycol and 0.01% w/v Tween 20, pH 3.8) was added and stirred for 25 min. after filtering, the residue was washed 5× with 50 mL 0.9% NaCl pH 4.5 (0.1 N HCl).

The residue was removed with 70 mL buffer pH 4.5 (0.1 N HCl) from the reactor and the reactor rinsed with 20 mL buffer pH 4.5 (0.1 N HCl) and the 2 fractions were unified and freeze dried.

Peptide content was determined by 1H-NMR and shown for 2 batches in table 4.

TABLE 4

| $l_{peptide}$ (ca. 7.1 ppm) | $m_{peptide}$ [mg] | $M_{peptide}$ [g/mol] | $l_{maleic\ acid}$ (6.25-6.3 ppm) | $m_{maleic\ acid}$ [mg] | $N_{peptide}$ | Content [% w/w] | Content [mol %] |
|---|---|---|---|---|---|---|---|
| 1.527 | 5.69 | 4440 | 4.235 | 0.2458 | 15 | 7.94 | 0.79 |
| 1.460 | 5.24 | 4440 | 4.235 | 0.2458 | 15 | 8.25 | 0.83 |

Analogously batches with different peptide content were prepared:

| Batch | Crosslinked HA | Seq. ID. No. 5 Content [% w/w] | Seq. ID. No. 5 Content [mol %] | Used in example |
|---|---|---|---|---|
| A | yes | 16.1 | 1.6 | 15, 19, 20 |
| B | yes | 16.5 | 1.64 | 18 |
| C | yes | 21.3 | 2.11 | 17, 21 |
| D | yes | 19.2 | 1.91 | 20 |
| E | no | 10.0 | 0.99 | 16 |

Example 13

Synthesis of Soluble Maleimide Functionalized HA

In a 100 mL flask were taken 200 mg of hyaluronic acid, sodium salt (mol. wt.=500 kDa) and 24 ml of DI water. It was stirred until a clear solution was obtained. To the rapidly stirred HA solution was added 16 mL of ethanol followed by 55 mg (0.2 mmol) of 4-(4,6-Dimethoxy-1,3,5-triazin-2-yl)-4-methylmorpholinium chloride in water/ethanol and N-methylmorpholine (20μl, 0.2 mmol). The reaction mixture reaction was stirred for one hour. Subsequently, an aqueous solution of 1-(2-(2-aminoethoxy)ethyl)-1H-pyrrole-2,5-dione.trifluoroacetate salt (60 mg, 0.2 mmol) was added and the resulting reaction mixture was allowed to stir for 14 hr. The pH of the reaction was adjusted to be slightly acidic. The reaction mixture was treated with treated with 15 ml of pre-washed Amberlite® CG-120 resin (Na$^+$ form) and the resulting reaction mixture was stirred for 20 minutes. The resin was filtered off and washed with deionized water. The combined filtrate was again treated with pre-15 ml of pre-washed Amberlite® CG-120 resin (Na$^+$ form) and the above procedure was followed. The Amberlite® resin treatment was repeated once more. The filtrate was diluted with water to form an aqueous solution containing <20% ethanol. The solution was spin-filtered using four PALL Macrosep® centrifugal devices 130 kDa molecular weight cutoff) for 15 minutes at a speed of 5000 rpm. The membrane was cleared each time by gently stroking a spatula over it and vigorously shaking the sealed device. The retentate was washed several times with deionized water (>200 ml). The resulting concentrates were combined and lyophilized yielding an off white solid with yield in the range of 50-75%. Degree of maleimide incorporation was estimated by 1NMR spectroscopy was found to be ~20 mole %.

Example 14

Determination of In Vivo Residence Time of the HA Hydrogel

The residence time of hydrogels in vivo in the subcutaneous space were investigated by magnetic resonance imaging (MRI) combined with CEST (Chemical Exchange Saturation Transfer) technique (Zihl et al Magn. Reson Med 2011, 65(4) 927-948. The intensity of water proton contrast inside the hydrogel was used to assess the hydrogels residence time in vivo. For this purpose, C57B mice were used in 2 groups of 4 animals. Animals were injected with either a solution (soluble) or suspension (divinyl sulfone cross-linked hydrogel) of the HA conjugated peptide Seq. ID NO: 5 with Aib-linker. The samples administered contain 1 to 3% weight of the drug substance HA derivative. The hydrogel was injected using a 31 G needle by following all approved animal care protocols.

The mice were serially imaged at least 7-9 times on a 7T-BRUKER scanner using a 72-mm volume coil over 77 days following hydrogel implantation. At each time-point, axial stacks of fat-suppressed T2W images were acquired using a spin-echo pulse sequence (RARE: TR/TE=3300/33 ms, NEX=2) with 0.17×0.17×1 mm$^3$ resolution and 10-15 slices to capture the entire hydrogel scaffold. Volumetric analysis was performed using Cheshire (V4.4.5, PAREXEL, Waltham, Mass., USA) and AMIRA V6.0.1 (FEI, Hillsboro, Oreg., USA) to calculate the hydrogel volumes. CEST sequence was performed on a sub-selection of animals from each group with the following parameters: 1-mm slice thickness, FOV=4.5×4.5 cm, matrix=128×96, RARE factor=16, TR/TE=3000/33 ms, MT module B1=10 μT/0.3 s (−6 to +6 ppm, 0.17 ppm steps). Prior to CEST, a localized spectroscopy scan was run around the hydrogel region for B0 shimming and evaluating the water-line width. Degree of asymmetry in the z-spectra was assessed using asymmetry plots (CEST_asym). Data processing was performed using ImageJ (NIH, Bethesda, Md., USA) and MS Excel. Histopathology was performed on representative samples at study termination (day 90) from each group.

The MRI imaging of the injection site was carried out daily for one week and subsequently measured once every week for 12. In one group, the divinyl crosslinked HA hydrogel was injected and in the other group, a suspension of containing 1:1 (w/w) mixture hydrogel and 2,500,000 Da soluble HA was used. In the case of animals treated with crosslinked HApure hydrogel, the gel was evident for more than until the end of the study (3 month) for with gradual but slow loss in intensity as a function of time (FIG. 1B). On the other hand, for the mixture high molecular weight containing soluble HA treated animals, the MR signal, which was intense on day 1, has significantly reduced by day 4 (FIG. 10). This observation suggests that to improve the residence time of the polymer carrier to provide long lasting therapeutic benefits, the HA polymer needs to be presented in its crosslinked form to achieve ultra high molecular weight.

FIG. 1A: In Vivo Degradation Profile and Kinetics of Degradation of High Molecular Wight (2.5 Million Da) Hyaluronan (HA).

The implanted HA was monitored by MRI technique. Representative MRI images obtained by both Standard (top) and CEST (bottom) imaging techniques.

FIG. 1B: In Vivo Degradation Profile and Kinetics of Degradation of Divinyl Sulfone Crosslinked Hyaluronan. Kinetics of degradation was determined by plotting peak magnitude at 1 ppm.

FIG. 1C: In Vivo Degradation Profile and Kinetics of Degradation of High Molecular Wight (2.5 Million Da) Hyaluronan (HA).

Kinetics of degradation was determined by plotting peak magnitude at 1 ppm.

Example 15

Release Kinetics In Vitro

An aliquot of GLP-1/Glucagon agonist Aib-linker hydrogel with peptide SEQ ID NO: 5 (0.5 mg GLP-1/Glucagon agonist) was transferred into a syringe equipped with a filter frit and washed 5 times with pH 7.4 phosphate buffer (60 mM, 3 mM EDTA, 0.01% Tween-20). The hydrogel was suspended in the same buffer and incubated at 37° C. At defined time points (after 1-7 days incubation time each) the supernatant was exchanged and liberated GLP-1/Glucagon agonist was quantified by RP-HPLC at 215 nm. UV-signals correlating to liberated GLP-1/Glucagon agonist were integrated and plotted against incubation time.

Curve-fitting software was applied to estimate the corresponding halftime of release.

FIG. 3 shows the in vitro release kinetics of Peptide with Seq. ID NO: 5 with Aib-linker from the HA hydrogel.

Example 16

Effects of SEQ ID NO: 5 after Subcutaneous Treatment on Blood Glucose In Fed, Male Diabetic db/db Mice Male diabetic, obese BKS.CG-m+/+Lepr(db)/J mice were ordered from Charles River and upon arrival housed in groups with wood chip bedding. At the study start mice were approximately 13-14 weeks old.

Mice were housed under vivarium conditions including a 12 h light/dark cycle (light phase 06:00 AM-6:00 PM), room temperatures between 23-26° C. and a relative humidity between 30-70%. All animals had free access to water and a rodent maintenance diet (Ssniff R/M–H).

Seven days prior to dosing body mass and HbA1c measurements were performed. Thereafter animals were assigned to treatment groups (n=8) and to new cages to match mean HbA1c and body masses between the db/db groups. On Day 1 of the dosing phase, animals were treated once with a s.c. injection (27G needle) of 25 nmol/kg SEQ ID NO: 5 with non-crosslinked HA. Dosing was initiated and completed between 08:30 and 09:30 AM. The applied volume was 5 ml/kg and the dose was adjusted to the most recent body mass recording of each individual.

Animals had unlimited access to water and feed during the experiment. On day 1 of the dosing phase blood glucose concentrations were measured prior to and 4 hours posttreatment. Thereafter blood glucose concentrations were assessed daily between 8:30 and 9:30 AM. For this purpose approximately 2 µL of blood were collected from the tail and blood glucose concentrations measured using a handheld device (Accu Chek).

Data are depicted as means±SEM in FIG. 4. Single s.c. treatment with 25 nmol/kg SEQ ID NO: 5 containing non-crosslinked HA resulted in a transient decrease in blood glucose concentrations and animals reached baseline concentrations approximately on day 7 post-dose.

Example 17

Effects after Subcutaneous Treatment on Blood Glucose, Body Mass, Whole Body Fat Content, and Feed Consumption In Female Diet-Induced Obese (DIO) C57BL/6 Mice Female C57BL/6NHsd mice were ordered group housed from Envigo RMS Inc., shipped group housed and remained group housed with shipped cage mates in disposable shoebox caging with wood chip bedding until day 38 of the pre-dose phase. At the study start mice were between 25-26 weeks old.

Mice were housed under vivarium conditions that included a 12 h light/dark cycle (light phase 04:00 AM-4:00 PM), room temperatures between 21-25° C. and a relative humidity between 30-70%. All animals had free access to water and diet (DIO: 75-TD97366, Lean: 10-Harlan2014) for 16 weeks prior to pharmacological intervention (dosing phase). Feed was replaced with fresh feed weekly until and for the last time on day 38 of the pre-dose phase. During the subsequent dosing phase, a portion of the remaining feed was removed, replaced with fresh feed, and pellets were mixed evenly once per week.

On pre-dose day 38, obese DIO mice were assigned to treatment groups (n=8) to match mean body masses between all DIO groups. An age-matched group with ad libitum access to a rodent maintenance diet was included in the study as a lean control group.

Mice were treated in the morning on day 1 and between 1:00 and 3:00 PM on days 8, 15, and 22—with a s.c. injection of cross-linked hyaluronic acid or 0.88 mg/kg*week SEQ ID NO: 5 using a 30 G needle. The applied volume was 300 µl per animal and alternate injection sites were used each week (1st injection left scapular, 2nd injection: right scapular, 3rd injection: left flank, 4th injection: right flank).

Body mass and feed consumption (estimated for groups of four mice housed in one cage) were measured daily between 01:00-03:00 PM throughout the 28 days of the dosing phase.

For statistical analyses a One-Way Analysis of Variance (ANOVA) was performed with Sigmaplot 12.5. The power of the performed test was alpha=0.050:0.999 and a comparison versus the DIO-Vehicle group was performed with Dunnett's Method. Lean-Vehicle group data were used as a reference dataset for the non-obese state.

The first dose of SEQ ID NO: 5 elicited a marked and sustained body mass-reducing effect that lasted until day 8 when the second dose was administered. The following three doses of SEQ ID NO: 5 maintain the low body mass (FIG. 5A left panel). By day 28 and after four doses, the mean body mass of SEQ ID NO: 5-treated mice was approximately 13.6 g and statistically significantly below the mean body mass of the DIO-Vehicle group (FIG. 5A right panel). The first steep decrease in body mass following administration of the first dose was associated with a pronounced feed consumption inhibition. Within 8 days SEQ ID NO: 5-treated mice normalized feed consumption and from then on displayed values comparable to the DIO-vehicle group (FIG. 5B).

Example 18

Pharmacokinetic in Female In Female C57BL/6 Mice 30 female C57BL/6 mice were used in this study. Animals had access to food and water ad libitum throughout the entire study period. The animals were dosed with 4.5 mg/kg kg of a suspension of HA-Aib-linker-Seq ID. No. 5. Plasma samples were taken at 2, 8, 24, 48, 72, 144, 192, 240, 312 and 336 h. Samples were analysed for the peptide. All quantitative results were determined by LC-MS/MS. For calculation of mean concentrations, values below the lower limit of quantification (LLOQ=1 ng/mL in plasma) were set to zero. The pharmacokinetic parameters were calculated by the program WinNonlin 6.4 using a non-compartmental model and linear trapezoidal interpolation calculation.

FIG. 6: Plasma concentrations and pharmacokinetic parameters of peptide of Seq. No. 5 after single subcutaneous administration of 4.5 mg/kg of HA-Aib-linker-conjugate to female C57BL/6 mice.

After subcutaneous administration, the half-life in plasma was very long around 7 days.

Example 19

Pharmakokinetic In Female Göttingen Minipigs 4 female diabetic Gottingen minipigs of average 35000 g weight were used in this study. Animals had access to food and water ad libitum throughout the entire study period. The animals were dosed with 0.623 mg/kg of a 16.05% suspension of HA-Aib-linker-Seq ID. No. 5. Plasma samples were taken at 0, 1, 4, 8, 24, 48 h and once a day on days 3 to 21 at the same time. Samples were analysed for the peptide. All quantitative results were determined by LC-MS/MS. For calculation of mean concentrations, values below the lower limit of quantification (LLOQ=1 ng/mL in plasma) were set to zero. The pharmacokinetic parameters were calculated by the program WinNonlin 6.4 using a non-compartmental model and linear trapezoidal interpolation calculation. FIG. 7 shows the plasma concentration values versus the time after one administration.

Mean Plasma pharmacokinetic parameters are:

TABLE 5

| $t_{max}$ (h) | $C_{max}$ (ng/mL) | $t_{last}$ (h) | $AUC_{last}$ (h * ng/mL) | $AUC_{inf}$ (h * ng/mL) | $AUC_{extr}$ (%) | $t_{1/2z}$ (h) | $AUC_{inf}$/Dose (dose normalized) |
|---|---|---|---|---|---|---|---|
| 192 | 28.7 | 504 | 7130 | 8670 | 14.3 | 139 | 13900 |

After subcutaneous administration, the half-life in plasma was very long around 139 h which are 5.8 days.

FIG. 7: Plasma concentrations and pharmacokinetic parameters of peptide of Seq. No. 5 after single subcutaneous administration of 0.623 mg/kg in suspension (16.05%) as HA-Aib-linker-conjugate to female Gottingen minipigs.

Example 20

Injectability Study

A suspension of 20 mg/mL HA-peptide conjugate (1) was prepared in a syringe by dispersing the appropriate amount of peptide conjugate in 20 mM acetate buffer at pH 4.5. In another syringe, a 20 mg/mL solution of native HA (2) was prepared by dissolving lyophilized HA in 20 mM acetate buffer at pH 4.5. (1) was mixed with (2) via a connector in a ratio of 4:1 and the resulting suspension (3) was stored at 2-8° C. overnight. (3) was allowed to adjust to room temperature and was then used for injectability experiments. For 1 mL BD plastic Luer-Lock syringes 27 G×½" or 29 G×½" needles were connected to the syringes. In case of the PFS experiments (3) was vacuum-filled into the syringes manually. The syringes containing (3) were loaded into the syringe holder of the LF Plus equipment. The injection speed was adjusted to 1 mL/10 s for the different syringes. The results for two different compounds (HA conjugated Seq. ID No. 5, Aib linker) are shown in table 6.

TABLE 6

| peptide content [wt %] | syringe | needle | maximum Load [N] | average Load [N] |
|---|---|---|---|---|
| 16.1 | 1 mL BD plastic Luer-Lock | 27G × ½" | 6.9 | 5.3 |
| 16.1 | 1 mL BD plastic Luer-Lock | 29G × ½" | 9.4 | 7.4 |
| 16.1 | HYPAK SCF, glass PFS | 27G × ½" | 15.5 ± 0.1 | 12.7 ± 1.0 |
| 16.1 | HYPAK SCF, glass PFS | 29G × ½" | 15.9 ± 0.1 | 13.2 ± 0.3 |
| 19.2 | HYPAK SCF, glass PFS | 27G × ½" | 14.5 ± 1.4 | 12.7 ± 1.1 |
| 19.2 | HYPAK SCF, glass PFS | 29G × ½" | 16.1 ± 0.9 | 13.2 ± 0.7 |

Example 21

Effects of SEQ ID NO: 5 After Subcutaneous Treatment On Blood Glucose In Fed, Male Diabetic db/db Mice—Comparison Pure Peptide SEQ ID NO: 5 with Crosslinked HA Conjugate of SEQ ID NO: 5 (Batch C)

Male diabetic, obese BKS.CG-m+/+Lepr(db)/J mice were ordered from Charles River and upon arrival housed in groups with wood chip bedding. At the study start mice were approximately 13-14 weeks old.

Mice were housed under vivarium conditions including a 12 h light/dark cycle (light phase 06:00 AM-6:00 PM), room temperatures between 23-26° C. and a relative humidity between 30-70%. All animals had free access to water and a rodent maintanence diet (Ssniff R/M–H).

Seven days prior to dosing body mass and HbA1c measurements were performed. Thereafter animals were assigned to treatment groups (n=8) and to new cages to match mean HbA1c and body masses between the db/db groups.

The dosing intervals were:

Peptide SEQ ID NO: 5: On Day 0 of the dosing phase animals were treated with a s.c. injection (27 G needle) of 1.7 nmol/kg. Dosing was initiated and completed between 08:30 and 09:30 AM and repeated on each day until day 13.

Crosslinked HA conjugate of SEQ ID NO: 5: On Day 0 of the dosing phase animals were treated once with a s.c. injection (27 G needle) of 50 nmol/kg.

Animals had unlimited access to water and feed during the experiment. On day 1 of the dosing phase blood glucose concentrations were measured prior to and 4 hours post-treatment. Thereafter blood glucose concentrations were assessed daily between 8:30 and 9:30 AM. For this purpose approximately 2 μL of blood were collected from the tail and blood glucose concentrations measured using a handheld device (Accu Chek).

Data are depicted as means±SEM in FIG. 8.

Single s.c. treatment with 50 nmol/kg crosslinked HA conjugate of SEQ ID NO: 5 resulted in a strong decrease in blood glucose concentrations for more than 8 days after then the concentrations rises.

Once daily s.c. treatment with 1.7 nmol/kg pure peptide of SEQ ID NO: 5 resulted in a strong decrease in blood glucose concentrations up to day 13 as long the animals were dosed.

The levels of blood glucose lowering for both treatments are comparable for more than 8 days.

The invention claimed is:

1. A conjugate comprising a crosslinked hyaluronic acid hydrogel, in which 0.001 to 20 mol % of the monomeric disaccharide units are crosslinked by a crosslinker and 0.2 to 20 mol % of the monomeric disaccharide units bear -$L^1$-$L^2$-L-Y—$R^{20}$ groups, wherein:

- $L^1$ is a $C_{1-20}$ alkyl chain comprising a terminal amino group, in which optionally one or more carbon atoms are replaced by a group selected from —O—, N($R^{5aa}$) and C(O)N($R^{5aa}$) and which is optionally substituted with one or more groups independently selected from OH and C(O)N($R^{5aa}R^{5aaa}$), wherein $R^{5aa}$ and $R^{5aaa}$ are independently selected from the group consisting of H and $C_{1-4}$ alkyl, and

- $L^1$ is attached to the hydrogel via the terminal amino group forming an amide bond with the carboxy group of the beta-1,3-D-glucuronic acid of the hyaluronic acid;

- $L^2$ is a single chemical bond or is a $C_{1-20}$ alkyl chain, in which optionally one or more carbon atoms are replaced by a group selected from —O— and C(O)N ($R^{3aa}$) and which is optionally substituted with one or more groups independently selected from OH and C(O)N($R^{3aa}R^{3aaa}$), wherein $R^{3aa}$ and $R^{3aaa}$ are independently selected from the group consisting of H and $C_{1-4}$ alkyl, and

- $L^2$ is attached to $L^1$ via a terminal group selected from the group consisting of

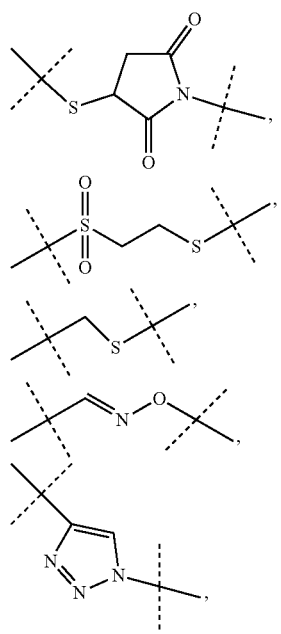

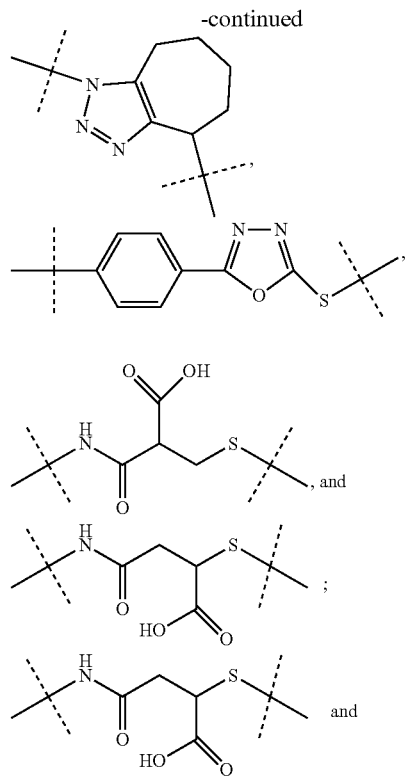

wherein $L^2$ is attached to one position indicated with the dashed line and $L^1$ is attached to the position indicated with the other dashed line;

L is a linker of formula (Ia),

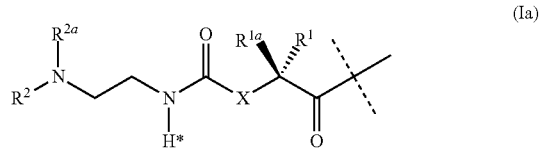

(Ia)

wherein the dashed line indicates the attachment to the N-Terminus of Y by forming an amide bond, X is C($R^4R^{4a}$) or N($R^4$), $R^1$, $R^{1a}$, are independently selected from the group consisting of H and $C_{1-4}$ alkyl, $R^2$, $R^{2a}$, are independently selected from the group consisting of H and $C_{1-4}$ alkyl, $R^4$, $R^{4a}$, are independently selected from the group consisting of H and $C_{1-4}$ alkyl, and wherein $L^2$ is attached to L in place of one of $R^2$, $R^{2a}$, $R^4$ or $R^{4a}$;

Y is a peptide moiety of formula (Ib)

```
His-D-Ser-Gln-Gly-Thr-Phe-Thr-Ser-Asp-Leu-Ser-Lys-
Gln-X14-Glu-Ser-Lys-Ala-Ala-Gln-Asp-Phe-Ile-Glu-
Trp-Leu-Lys-Ala-Gly-Gly-Pro-Ser-Ser-Gly-Ala-Pro-
Pro-Pro-Ser (Ib)
``` wherein X14 is Lys, wherein the —$NH_2$ side chain group is functionalized by (S)-4-carboxy-4-hexadecanoylamino-butyryl; or Y is a peptide moiety of formula (Ic)

```
His-dSer-Gln-Gly-Thr-Phe-Thr-Ser-Asp-Leu-Ser-Lys-
Gln-X14-Asp-Glu-Gln-Leu-Ala-Lys-Asp-Phe-Ile-Glu-
Trp-Leu-Lys-Ala-Gly-Gly-Pro-Ser-Ser-Gly-Ala-Pro-
Pro-Pro-Ser (Ic)
``` wherein X14 is Lys, wherein the —$NH_2$ side chain group is functionalized by (S)-4-carboxy-4-octadecanoylamino-butyryl; and $R^{20}$ is OH or $NH_2$;

or a salt or solvate thereof.

2. The conjugate of claim 1 comprising a crosslinked hyaluronic acid hydrogel, in which 0.001 to 20 mol % of the monomeric disaccharide units are crosslinked by a crosslinker, 0.2 to 20 mol % of the monomeric disaccharide units bear -$L^1$-$L^2$-L-Y—$R^{20}$ groups, and 0.2 to 30 mol % of the monomeric disaccharide units of the crosslinked hyaluronic acid hydrogel bear -$L^1$-Z—OH groups, wherein:

$L^1$ is a $C_{1-20}$ alkyl chain comprising a terminal amino group, in which optionally one or more carbon atoms are replaced by a group selected from —O—, N($R^{5aa}$) and C(O)N($R^{5aa}$) and which is optionally substituted with one or more groups independently selected from OH and C(O)N($R^{5aa}R^{5aaa}$), wherein $R^{5aa}$ and $R^{5aaa}$ are independently selected from the group consisting of H and $C_{1-4}$ alkyl, and $L^1$ is attached to the hydrogel via the terminal amino group forming an amide bond with the carboxy group of the beta-1,3-D-glucuronic acid of the hyaluronic acid;

$L^2$ is a single chemical bond or is a $C_{1-20}$ alkyl chain, in which optionally one or more carbon atoms are replaced by a group selected from —O— and C(O)N($R^{3aa}$) and which is optionally substituted with one or more groups independently selected from OH and C(O)N($R^{3aa}R^{3aaa}$), wherein $R^{3aa}$ and $R^{3aaa}$ are independently selected from the group consisting of H and $C_{1-4}$ alkyl, and $L^2$ is attached to $L^1$ via a terminal group selected from the group consisting of

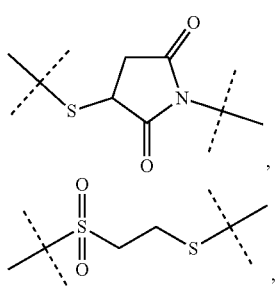

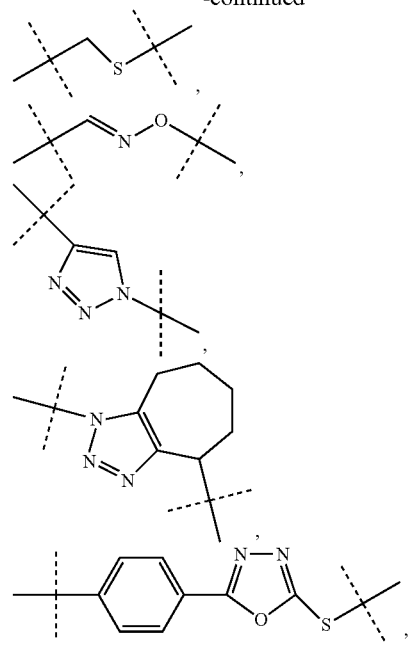

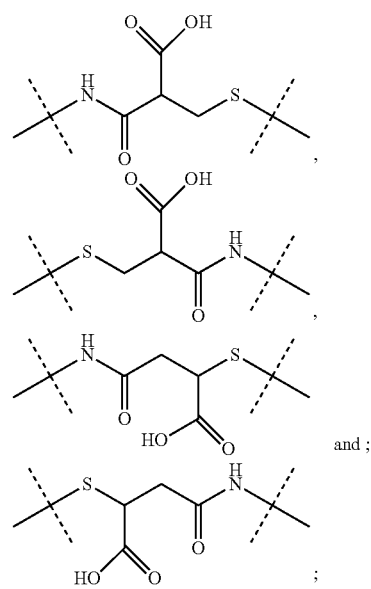

wherein $L^2$ is attached to one position indicated with the dashed line and $L^1$ is attached to the position indicated with the other dashed line;

Z is a $C_{1-16}$ alkyl chain, in which optionally one or more carbon atoms are replaced by a group selected from —O— and C(O)N($R^{6aa}$); wherein $R^{6aa}$ is hydrogen or $C_{1-4}$ alkyl; or and Z is

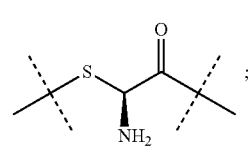

Z is attached to L¹ via a terminal group selected from the group consisting of

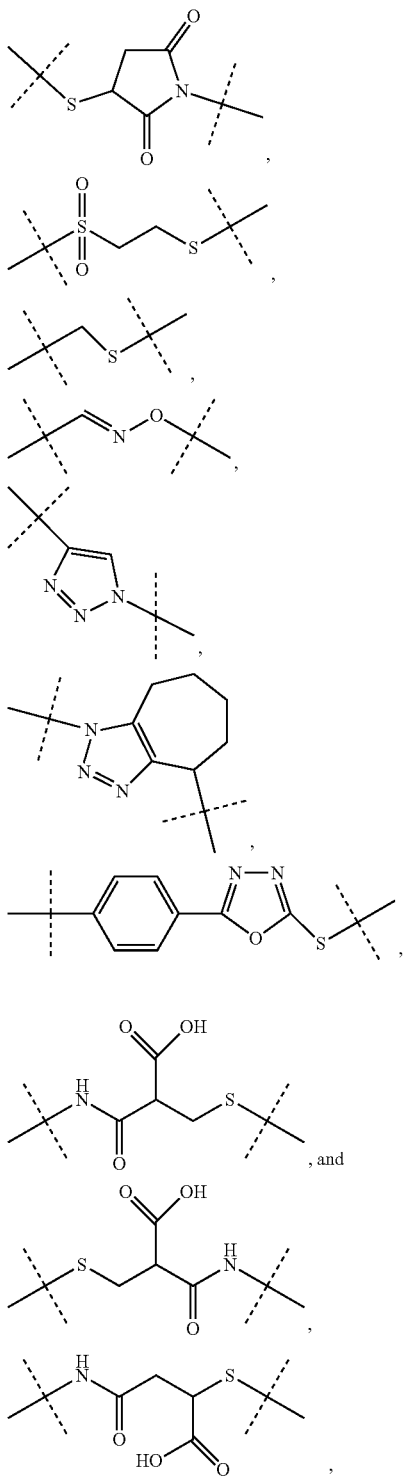

, and wherein Z is attached to one position indicated with the dashed line and L¹ is attached to the position indicated with the other dashed line;

L is a linker of formula (Ia),

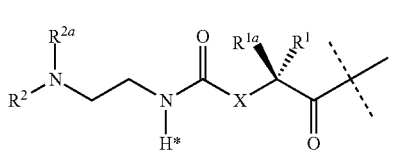

(Ia)

wherein the dashed line indicates the attachment to the N-Terminus of Y by forming an amide bond, X is $C(R^4R^{4a})$ or $N(R^4)$, $R^1$, $R^{1a}$, are independently selected from the group consisting of H and $C_{1-4}$ alkyl, $R^2$, $R^{2a}$, are independently selected from the group consisting of H and $C_{1-4}$ alkyl, $R^4$, $R^{4a}$, are independently selected from the group consisting of H and $C_{1-4}$ alkyl, wherein $L^2$ is attached to L in place of one of $R^2$, $R^{2a}$, $R^4$ or $R^{4a}$;

Y is a peptide moiety of formula (Ib)

```
His-D-Ser-Gln-Gly-Thr-Phe-Thr-Ser-Asp-Leu-Ser-Lys-
Gln-X14-Glu-Ser-Lys-Ala-Ala-Gln-Asp-Phe-Ile-Glu-
Trp-Leu-Lys-Ala-Gly-Gly-Pro-Ser-Ser-Gly-Ala-Pro-
Pro-Pro-Ser   (Ib)
``` wherein X14 is Lys, wherein the —NH₂ side chain group is functionalized by (S)-4-carboxy-4-hexadecanoylamino-butyryl; or Y is a peptide moiety of formula (Ic)

```
His-dSer-Gln-Gly-Thr-Phe-Thr-Ser-Asp-Leu-Ser-Lys-
Gln-X14-Asp-Glu-Gln-Leu-Ala-Lys-Asp-Phe-Ile-Glu-
Trp-Leu-Lys-Ala-Gly-Gly-Pro-Ser-Ser-Gly-Ala-Pro-
Pro-Pro-Ser   (Ic)
``` wherein X14 is Lys, wherein the —NH₂ side chain group is functionalized by (S)-4-carboxy-4-octadecanoylamino-butyryl; and $R^{20}$ is OH or NH₂;

or a salt or solvate thereof.

3. The conjugate of claim 1, wherein:
-L¹-L²-L- is a linker moiety of formula (IIa),

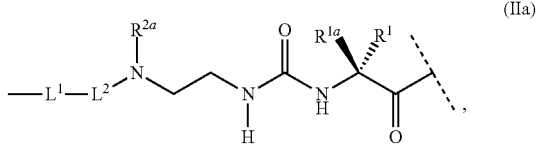

(IIa)

wherein the dashed line indicates attachment to Y by forming an amide bond;

$R^1$ is CH₃;

$R^{1a}$ is CH₃; and $R^{2a}$ is H;

or a salt or solvate thereof.

4. The conjugate of claim 2, wherein:
-L¹-L²-L- is a linker moiety of formula (IIa),

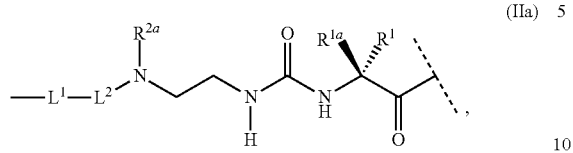

wherein the dashed line indicates attachment to Y by forming an amide bond;
R¹ is CH₃;
R¹ᵃ is CH₃; and
R²ᵃ is H;
or a salt or solvate thereof.

5. The conjugate of claim 1, wherein:
L² is a $C_{1-6}$ alkyl chain, in which optionally one carbon atom is replaced by a group selected from —O— and C(O)N(R³ᵃᵃ),
wherein R³ᵃᵃ is independently selected from the group consisting of H and $C_{1-4}$ alkyl; and
L² is attached to L¹ via a terminal group selected from the group consisting of

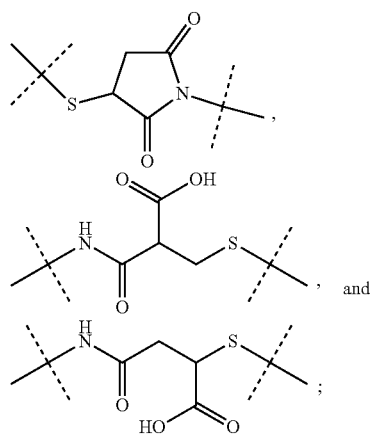

wherein L² is attached to one position indicated with the dashed line and L¹ is attached to the position indicated with the other dashed line;
or a salt or solvate thereof.

6. The conjugate of claim 1, or a salt or solvate thereof, wherein the crosslinker is divinylsulfone.

7. The conjugate of claim 2, wherein:
Z is —CH₂—CH₂—; or
Z is

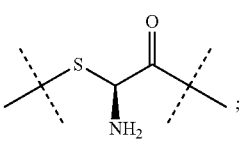

and
Z is attached to L¹ via a terminal group selected from the group consisting of

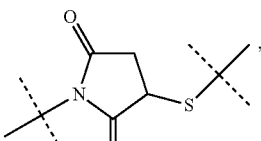

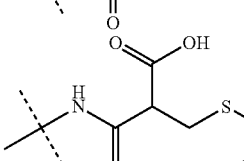

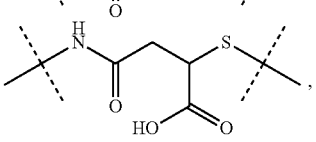

wherein Z is attached to one position indicated with the dashed line and L¹ is attached to the position indicated with the other dashed line;
or a salt or solvate thereof.

8. The conjugate of claim 2, wherein:
Z is —CH₂—CH₂—; and
Z is attached to L¹ via a terminal group

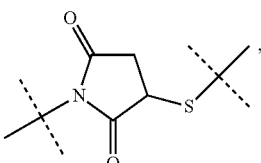

wherein Z is attached to one position indicated with the dashed line and L¹ is attached to the position indicated with the other dashed line;
or a salt or solvate thereof.

9. The conjugate of claim 1, wherein:
-L¹-L²-L-Y is a moiety of formula (IIIb),

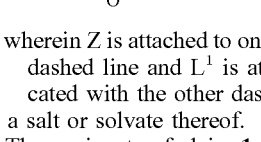

or a salt or solvate thereof.

10. The conjugate of claim 1, wherein:
-L¹-L²-L-Y is a moiety of formula (IIIa),

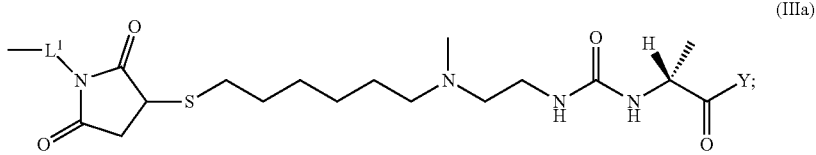

or a salt or solvate thereof.

11. The conjugate of claim 1, wherein:
-L¹-L²-L-Y is a moiety of formula (IIIc),

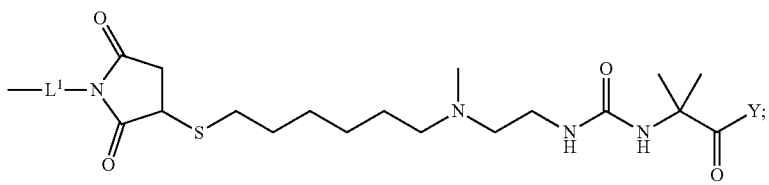

or a salt or solvate thereof.

12. The conjugate of claim 1, or a salt or solvate thereof, wherein Y is the GLP-1/Glucagon agonist of SEQ ID NO: 5.

13. The conjugate of claim 1, or a salt or solvate thereof, wherein Y is the GLP-1/Glucagon agonist of SEQ ID NO: 6.

14. The conjugate of claim 1 comprising a crosslinked hyaluronic acid hydrogel, in which 0.001 to 20 mol % of the monomeric disaccharide units are crosslinked by divinylsulfone, and 0.5 to 5 mol % of the monomeric disaccharide units bear -L¹-L²-L-Y—R²⁰ groups, wherein:
the -L¹-L²-L-Y group is of formula (IIIb)

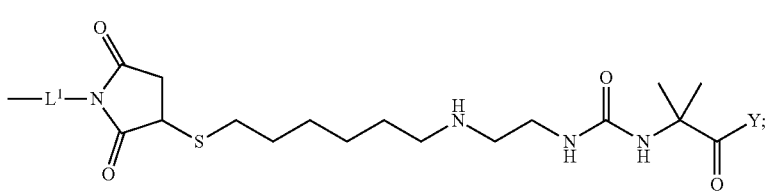

wherein
L¹ is —NH—CH₂—CH₂—CH₂—NH—CO—CH₂—CH₂—, and
L¹ is attached to the hydrogel via the terminal amino group forming an amide bond with the carboxy group of the beta-1,3-D-glucuronic acid of the hyaluronic acid; and 0.2 to 30 mol % of the monomeric disaccharide units of the crosslinked hyaluronic acid hydrogel bear -L¹-Z—OH groups, wherein
Z is —CH₂—CH₂—,
Z is attached to L¹ via a terminal group,

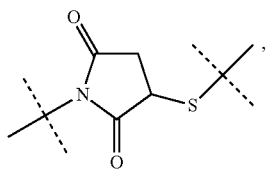

and
wherein Z is attached to one position indicated with the dashed line and L¹ is attached to the position indicated with the other dashed line; and Y is a peptide of SEQ ID NO: 5;
or a salt or solvate thereof.

15. A pharmaceutical composition comprising a conjugate of claim 1, or a salt or solvate thereof, and at least one pharmaceutically acceptable excipient.

16. The pharmaceutical composition of claim 15, further comprising a viscosity modifier.

17. The pharmaceutical composition of claim 16, wherein the viscosity modifier is hyaluronic acid.

18. The pharmaceutical composition of claim 17, wherein the viscosity modifier is hyaluronic acid in a concentration of 5 to 30 weight/volume percent.

19. The pharmaceutical composition of claim 15, in the form of an injectable formulation.

20. The pharmaceutical composition of claim 19, which can be administered by injection through a needle smaller than 0.26 mm inner diameter (26 Gauge).

21. The pharmaceutical composition of claim 19, wherein a volume of 1 mL can be extruded at room temperature within 10 seconds by applying a force of equal/less than 20 Newtons through a needle of 26 gauge.

22. The pharmaceutical composition of claim 15, in the form of a suspension.

23. The pharmaceutical composition of claim 15, wherein the conjugate or salt or solvate thereof has a concentration of 0.5 to 8 weight/volume percent.

24. The pharmaceutical composition of claim 15, wherein the conjugate or salt or solvate thereof has a concentration of 1.5 to 3 weight/volume percent.

25. The pharmaceutical composition of claim 15, wherein the conjugate or salt or solvate thereof is sufficiently dosed in the pharmaceutical composition to provide a therapeutically effective amount of GLP 1/Glucagon agonist for at least 6 days in one application.

26. The pharmaceutical composition of claim 15, wherein the pharmaceutical composition is a single dose composition.

27. A method of treating or preventing diseases or disorders which can be treated by a GLP-1/Glucagon agonist, the method comprising administering the conjugate or the salt or solvate thereof of claim 1.

28. The method of claim 27 wherein the disease or disorder is diabetes.

29. The method of claim 27 wherein the disease or disorder is obesity.

30. The method of claim 27 wherein the disease or disorder is dyslipidemia.

31. The method of claim 27 wherein the disease or disorder is metabolic syndrome.

32. The method of claim 27 wherein the disease or disorder is hepatosteatosis.

33. A method of treating Type 1 diabetes, Type 2 diabetes, obesity, or hyperglycemia in a patient, the method comprising administering the conjugate of claim 1, or a salt or solvate thereof, via an injection device comprising a tube having a needle gauge of 26 or greater and wherein the conjugate, or salt or solvate thereof, is administered once weekly.

34. An injection device comprising a tube having a gauge of 28 or greater and a conjugate of claim 1, or a salt or solvate thereof.

35. A method of treating Type 1 diabetes, Type 2 diabetes, obesity, or hyperglycemia in a patient, the method comprising treating the patient with the injection device of claim 34.

36. The method of claim 35, wherein the conjugate, or a salt or solvate thereof is administered once weekly.

\* \* \* \* \*